United States Patent
Masukawa

(10) Patent No.: US 8,372,306 B2
(45) Date of Patent: *Feb. 12, 2013

(54) LIQUID CRYSTAL COMPOUND HAVING NEGATIVE DIELECTRIC ANISOTROPY, LIQUID CRYSTAL COMPOSITION, AND LIQUID CRYSTAL DISPLAY DEVICE

(75) Inventor: Tokifumi Masukawa, Chiba (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 445 days.

This patent is subject to a terminal disclaimer.

(21) Appl. No.: 12/482,116

(22) Filed: Jun. 10, 2009

(65) Prior Publication Data

US 2009/0324854 A1    Dec. 31, 2009

(30) Foreign Application Priority Data

Jun. 27, 2008  (JP) ................. 2008-169161

(51) Int. Cl.
- *C09K 19/06* (2006.01)
- *C09K 19/32* (2006.01)
- *C09K 19/00* (2006.01)
- *C09K 19/52* (2006.01)
- *C07D 315/00* (2006.01)

(52) U.S. Cl. .......... 252/299.61; 252/299.01; 252/299.6; 252/299.63; 252/299.64; 252/299.65; 428/1.1; 428/1.3; 549/416; 549/417; 549/427; 549/428

(58) Field of Classification Search .............. 428/1.1, 428/1.3; 252/299.01, 299.6, 299.61, 299.63, 252/299.64, 299.65; 549/416, 417, 427, 549/428

See application file for complete search history.

(56) References Cited

U.S. PATENT DOCUMENTS

| 5,279,764 | A | 1/1994 | Reiffenrath et al. | |
|---|---|---|---|---|
| 6,558,758 | B1 | 5/2003 | Yanai et al. | |
| 7,767,278 | B2 * | 8/2010 | Kibe et al. | 428/1.1 |
| 7,767,279 | B2 * | 8/2010 | Hattori et al. | 428/1.1 |
| 7,914,862 | B2 * | 3/2011 | Masukawa | 428/1.1 |
| 2004/0065866 | A1 | 4/2004 | Kato et al. | |
| 2008/0063814 | A1 | 3/2008 | Shimada | |
| 2008/0230746 | A1 | 9/2008 | Kibe et al. | |

FOREIGN PATENT DOCUMENTS

| EP | 0967261 | 12/1999 |
|---|---|---|
| JP | 2008-285570 | 11/2008 |
| WO | 89/08633 | 9/1989 |

OTHER PUBLICATIONS

Article Titled "Distortion of Twisted Orientation Patterns in Liquid Crystals by Magnetic Fields" authored by F.M. Leslie in Mol. Cryst. Liq. Cryst., 1970, vol. 12, pp. 57-72.

"International Search Report of corresponding PCT application", issued on Jul. 8, 2009, p. 1-4.

* cited by examiner

*Primary Examiner* — Geraldina Visconti

(74) *Attorney, Agent, or Firm* — J.C. Patents

(57) ABSTRACT

A liquid crystal compound is provided that has excellent characteristics, such as a negatively large dielectric anisotropy. A liquid crystal composition containing the compound, and a liquid crystal display device containing the composition are also provided. A compound having the three factors, i.e., (1) a tetrahydropyran ring, (2) terminal alkenyl chain and (3)

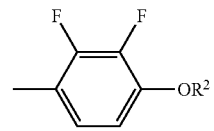

exhibits excellent characteristics including a negatively large dielectric anisotropy ($\Delta\epsilon$). The use of the compound having the characteristics provides an excellent liquid crystal composition and an excellent liquid crystal display device.

16 Claims, No Drawings

LIQUID CRYSTAL COMPOUND HAVING NEGATIVE DIELECTRIC ANISOTROPY, LIQUID CRYSTAL COMPOSITION, AND LIQUID CRYSTAL DISPLAY DEVICE

BACKGROUND OF THE INVENTION

1. Field of the Invention

The present invention relates to a novel liquid crystal compound and a liquid crystal composition. More specifically, it relates to a liquid crystal compound having a negative dielectric anisotropy ($\Delta\epsilon$), a liquid crystal composition containing the compound, and a liquid crystal display device containing the liquid crystal composition.

2. Related Art

A liquid crystal display device is classified, depending on the display mode thereof, into such modes as DS (dynamic scattering), TN (twisted nematic), GH (guest host), STN (super twisted nematic), IPS (in-plane switching), VA (vertical alignment), OCB (optically compensated bend) and PSA (polymer sustained alignment). A liquid crystal composition contained in the liquid crystal display devices desirably has some or all of the following common characteristics in all the display modes.

(1) The composition is stable to external environmental factors, such as water, air, heat and light.
(2) The composition exhibits a liquid crystal phase in a wide temperature range centering around room temperature.
(3) The composition has a small viscosity.
(4) The composition can decrease a driving voltage upon driving the display device.
(5) The composition has an optimum dielectric anisotropy ($\Delta\epsilon$).
(6) The composition has an optimum refractive index anisotropy ($\Delta n$).

However, such a liquid crystal compound has not yet been found that satisfies all of characteristics (1) to (6) by a sole compound. Therefore, a liquid crystal composition is often obtained by mixing several kinds or a couple dozen kinds of liquid crystal compounds Accordingly, the liquid crystal compounds used as components of the composition necessarily have good compatibility with each other. A liquid crystal display device capable of being used in various environments, such as a very low temperature, has been demanded in recent years, and liquid crystal compounds exhibiting good compatibility at a very low temperature are thus also demanded.

In recent years, among the aforementioned display modes, such modes as IPS, VA, OCB and PSA are receiving attention as a display mode capable of overcoming a narrow viewing angle of a liquid crystal display device, which is the biggest problem of a liquid crystal display device. In particular, a liquid crystal display device of the VA mode, the IPS mode and the PSA mode among these modes is being developed earnestly since it has excellent responsivity in addition to the wide viewing angle, and is capable of providing high-contrast display. The characteristics of the liquid crystal composition used in the liquid crystal display device of these modes reside in a negative dielectric anisotropy ($\Delta\epsilon$). It has been known that a liquid crystal composition having a negatively large dielectric anisotropy ($\Delta\epsilon$) can decrease the driving voltage of a liquid crystal display device containing the liquid crystal composition (as described in M. F. Leslie, Mol. Cryst. Liq. Cryst., vol. 12, p. 57 (1970)). Accordingly, liquid crystal compounds as the constitutional components of the liquid crystal composition are also demanded to have a negatively larger dielectric anisotropy ($\Delta\epsilon$).

As a component of a liquid crystal composition having a negative dielectric anisotropy ($\Delta\epsilon$), various liquid crystal compounds where hydrogen at a lateral position of a benzene ring is replaced by fluorine have been investigated (as described, for example, in Japanese Patent No. 2,811,342 and JP H2-4725 A/1990). The following compound (a) has been reported, for example. However, the compound (a) has a negative dielectric anisotropy ($\Delta\epsilon$), but the extent thereof is not necessarily large in some cases, and therefore, the compound is not sufficient in some cases for decreasing the driving voltage of a liquid crystal display device of the VA mode and the IPS mode.

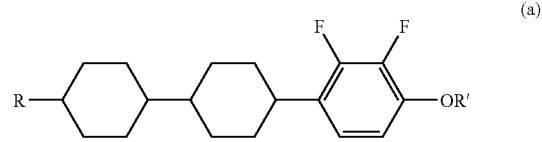

wherein R and R' each are alkyl.

Under the circumstances, there have been made attempts to increase the absolute value of the negative dielectric anisotropy ($\Delta\epsilon$) of the compound having a 2,3-difluorophenylene skeleton. For example, such a compound has been reported that is obtained by introducing a tetrahydropyran-2,5-diyl skeleton to the compound having a 2,3-difluorophenylene skeleton (as described, for example, in JP 2000-8040 A/2000 and JP 2001-115161 A/2001). The compound (b) has a negatively larger dielectric anisotropy ($\Delta\epsilon$) than the compound (a).

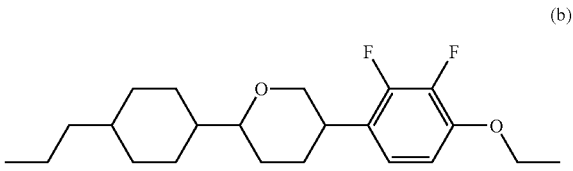 [SMILES: CCCC1CCC(C2CCC(c3ccc(OCC)c(F)c3F)CO2)CC1]

However, for decreasing the driving voltage of a liquid crystal display device of the VA mode and the IPS mode, a liquid crystal compound that has a negatively larger dielectric anisotropy ($\Delta\epsilon$), a liquid crystal composition containing the compound, and a liquid crystal display device containing the composition have been demanded.

SUMMARY OF THE INVENTION

The invention relates to a compound represented by formula (1-1) or (1-2):

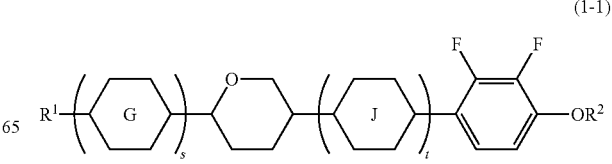

(1-2)

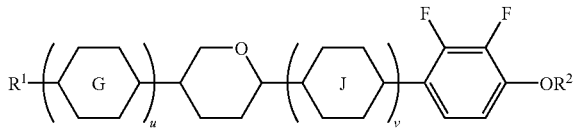

wherein

R¹ is alkenyl having 2 to 10 carbons, in the alkenyl arbitrary —CH₂— may be replaced by —O—, —S—, —CO— or —SiH₂—, provided that plural —CH₂— adjacent to each other are not replaced simultaneously;

R² is alkyl having 1 to 10 carbons, in the alkyl having 2 to 10 carbons arbitrary —CH₂— may be replaced by —O—, —S—, —CO— or —SiH₂—, provided that plural —CH₂— adjacent to each other are not replaced simultaneously, and arbitrary —(CH₂)₂— may be replaced by —CH═CH— or —C≡C—;

ring G and ring J are each independently 1,4-cyclohexylene or 1,4-phenylene, in the 1,4-cyclohexylene arbitrary —CH₂— may be replaced by —O—, —S—, —CO— or —SiH₂—, and arbitrary —(CH₂)₂— may be replaced by —CH═CH—, and in the 1,4-phenylene arbitrary —CH═ may be replaced by —N═;

s and t are each independently 0, 1, 2 or 3, provided that the sum of s and t is 1, 2 or 3; and u is 0, 1 or 2, and v is 1, 2, or 3, provided that the sum of u and v is 1, 2, or 3, provided that in formula (1-1), when s=1 and t=0, ring G is 1,4-phenylene, in which arbitrary —CH═ may be replaced by —N═, and in formula (1-2), when u=0 and v=1, ring J is 1,4-cyclohexylene, in which arbitrary —CH₂— may be replaced by —O—, —S—, —CO— or —SiH₂—, and arbitrary —(CH₂)₂— may be replaced by —CH═CH—.

The invention also relates to a liquid crystal composition that contains the liquid crystal compound, a liquid crystal display device containing the liquid crystal composition, and so forth.

DETAILED DESCRIPTION OF THE INVENTION

One of the advantages of the invention is to provide such a liquid crystal compound that not only has a negatively large dielectric anisotropy (Δε), but also has at least one of characteristics including a stability to heat, light and so forth, a high clear point, a suitable refractive index anisotropy (Δn) and a good compatibility with other liquid crystal compounds.

Another one of the advantages of the invention is to provide such a liquid crystal composition containing the compound that has a low viscosity, a suitable refractive index anisotropy (Δn), a suitable negative dielectric anisotropy (Δε) and a low threshold voltage, and also has at least one of characteristics including a high maximum temperature of a nematic phase (a high phase transition temperature from a nematic phase to an isotropic phase) and a low minimum temperature of a nematic phase, or has good balance among at least two of the characteristics.

Still another one of the advantages of the invention is to provide such a liquid crystal display device containing the composition that has at least one of characteristics including a short response time, a small electric power consumption, a small driving voltage and a large contrast, and capability of being used in a wide temperature range, or has good balance among at least two of the characteristics.

As a result of earnest investigations made by the inventors, it has been found that an advantage that the dielectric anisotropy (Δε) becomes negatively large is obtained by synergistic effect of the following three factors present in the compound, and thus the invention has been completed.

The invention includes features of the following items (1) to (17):

(1) A compound represented by formula (1-1) or (1-2):

(1-1)

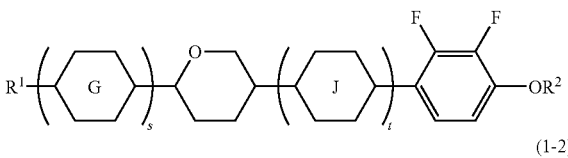

(1-2)

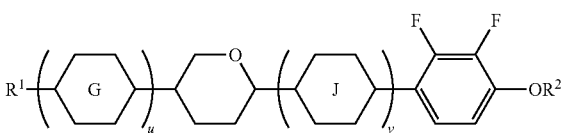

wherein

R¹ is alkenyl having 2 to 10 carbons, in the alkenyl arbitrary —CH₂— may be replaced by —O—, —S—, —CO— or —SiH₂—, provided that plural —CH₂— adjacent to each other are not replaced simultaneously;

R² is alkyl having 1 to 10 carbons, in the alkyl having 2 to 10 carbons arbitrary —CH₂— may be replaced by —O—, —S—, —CO— or —SiH₂—, provided that plural —CH₂— adjacent to each other are not replaced simultaneously, and arbitrary —(CH₂)₂—may be replaced by —CH═CH— or —C≡C—;

ring G and ring J are each independently 1,4-cyclohexylene or 1,4-phenylene, in the 1,4-cyclohexylene arbitrary —CH₂— may be replaced by —O—, —S—, —CO— or —SiH₂—, and arbitrary —(CH₂)₂— may be replaced by —CH═CH—, and in the 1,4-phenylene arbitrary —CH═ may be replaced by —N═;

s and t are each independently 0, 1, 2 or 3, provided that the sum of s and t is 1, 2 or 3; and u is 0, 1 or 2, and v is 1, 2, or 3, provided that the sum of u and v is 1, 2, or 3, provided that in formula (1-1), when s=1 and t=0, ring G is 1,4-phenylene, in which arbitrary —CH═ may be replaced by —N═, and in formula (1-2), when u=0 and v=1, ring J is 1,4-cyclohexylene, in which arbitrary —CH₂— may be replaced by —O—, —S—, —CO— or —SiH₂—, and arbitrary —(CH₂)₂— may be replaced by —CH═CH—.

(2) The compound according to item 1, wherein in formulae (1-1) and (1-2), R¹ is alkenyl having 2 to 10 carbons; R² is alkyl having 1 to 10 carbons; and ring G and ring J are each independently 1,4-cyclohexylene or 1,4-phenylene.

(3) The compound according to items 1 or 2, wherein in formulae (1-1) and (1-2), the sum of s and t is 1; u is 0; and v is 1.

(4) A compound represented by formula (1-1-1):

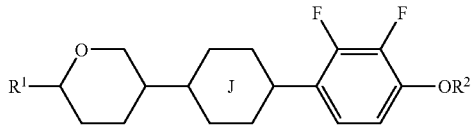
(1-1-1)

wherein $R^1$ is alkenyl having 2 to 10 carbons, $R^2$ is alkyl having 1 to 10 carbons; and ring J is 1,4-cyclohexylene or 1,4-phenylene.

(5) A compound represented by formula (1-2-1):

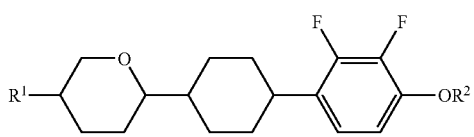
(1-2-1)

wherein $R^1$ is alkenyl having 2 to 10 carbons; and $R^2$ is alkyl having 1 to 10 carbons.

(6) A liquid crystal composition comprising, as a component A, at least one of the compound according to any one of items 1 to 5.

(7) The liquid crystal composition according to item 6, wherein the liquid crystal composition further comprises, as a component B, at least one compound selected from the group consisting of compounds represented by formulae (2), (3) and (4):

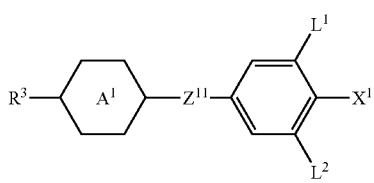
(2)

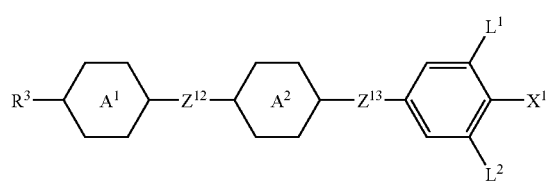
(3)

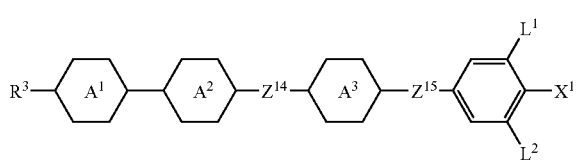
(4)

wherein $R^3$ is alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;

$X^1$ is fluorine, chlorine, —$OCF_3$, —$OCHF_2$, —$CF_3$, —$CHF_3$, —$CH_2F$, —$OCF_2CHF_2$ or —$OCF_2CHFCF_3$;

ring $A^1$, ring $A^2$ and ring $A^3$ are each independently 1,4-cyclohexylene, 1,3-dioxan-2,5-diyl, pyrimidin-2,5-diyl, 1-tetrahydropyran-2,5-diyl or 1,4-phenylene, in which arbitrary hydrogen may be replaced by fluorine;

$Z^{11}$, $Z^{12}$, $Z^{13}$, $Z^{14}$ and $Z^{15}$ are each independently —$(CH_2)_2$—, —$(CH_2)_4$—, —COO—, —$CF_2O$—, —$OCF_2$—, —CH=CH—, —C≡C—, —$CH_2O$— or a single bond; and $L^1$ and $L^2$ are each independently hydrogen or fluorine.

(8) The liquid crystal composition according to item 6, wherein the liquid crystal composition further comprises, as a component C, at least one compound selected from the group consisting of compounds represented by formula (5):

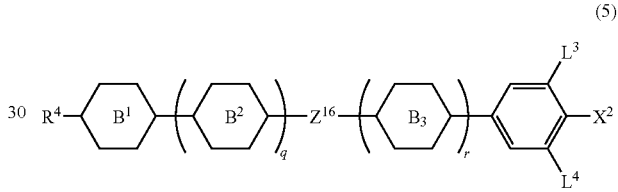
(5)

wherein $R^4$ is alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;

$X^2$ is —C≡N or —C≡C—CN;

ring $B^1$, ring $B^2$ and ring $B^3$ are each independently 1,4-cyclohexylene, 1,4-phenylene, in which arbitrary hydrogen may be replaced by fluorine, 1,3-dioxan-2,5-diyl, 1-tetrahydropyran-2,5-diyl or pyrimidin-2,5-diyl;

$Z^{16}$ is —$(CH_2)_2$—, —COO—, —$CF_2O$—, —$OCF_2$—, —C≡C—, —$CH_2O$— or a single bond;

$L^3$ and $L^4$ are each independently hydrogen or fluorine;

q is 0, 1 or 2; and r is 0 or 1.

(9) The liquid crystal composition according to item 6, wherein the liquid crystal composition further comprises, as a component D, at least one compound selected from the group consisting of compounds represented by formulae (6), (7), (8), (9) and (10):

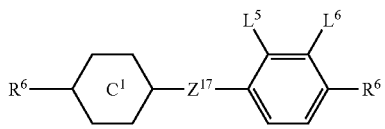
(6)

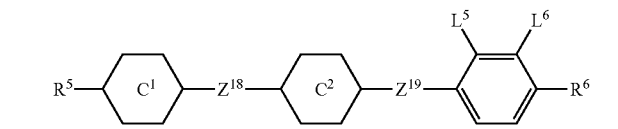
(7)

(8)
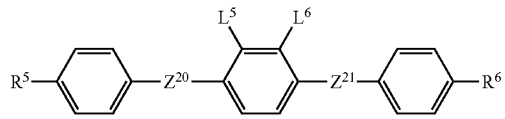

(9)
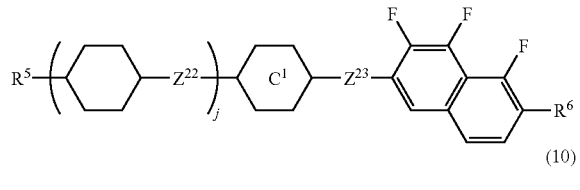

(10)
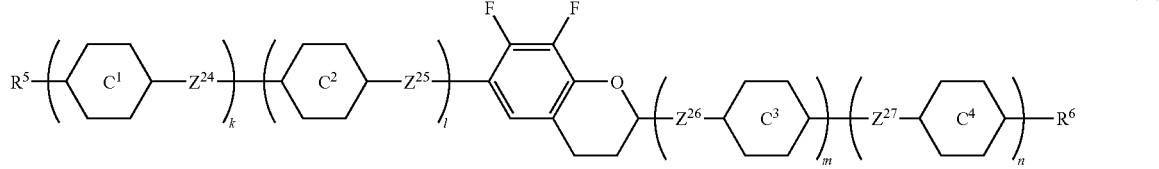

wherein
$R^5$ and $R^6$ are each independently alkyl having 1 to 10 carbons or alkenyl having 2 to 10 carbons, provided that in the alkyl and the alkenyl, arbitrary hydrogen may be replaced by fluorine, and arbitrary —CH$_2$— may be replaced by —O—;

ring $C^1$, ring $C^2$, ring $C^3$ and ring $C^4$ are each independently 1,4-cyclohexylene, 1,4-cyclohexenylene, 1,4-phenylene, in which arbitrary hydrogen may be replaced by fluorine, 6-tetrahydropyran-2,5-diyl or decahydro-2,6-naphthalene;

$Z^{17}$, $Z^{18}$, $Z^{19}$, $Z^{20}$, $Z^{21}$, $Z^{22}$, $Z^{23}$, $Z^{24}$, $Z^{25}$, $Z^{26}$ and $Z^{27}$ are each independently —(CH$_2$)$_2$—, —COO—, —CH$_2$O—, —OCF$_2$—, —OCF$_2$(CH$_2$)$_2$— or a single bond;

$L^5$ and $L^6$ are each independently chlorine or fluorine; and
j, k, l, m and n are each independently 0 or 1, provided that the sum of k, l, m and n is 1 or 2.

(10) The liquid crystal composition according to item 6, wherein the liquid crystal composition further comprises, as a component E, at least one compound selected from the group consisting of compounds represented by formulae (11), (12) and (13):

(11)
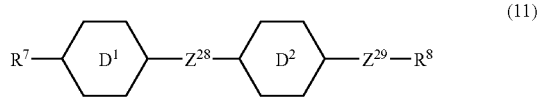

(12)
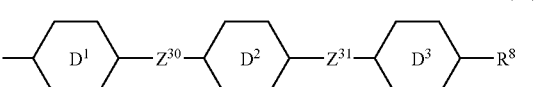

(13)
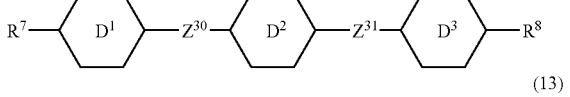

wherein
$R^7$ and $R^8$ are each independently alkyl having 1 to 10 carbons or alkenyl having 2 to 10 carbons, provided that in the alkyl having 2 to 10 carbons and the alkenyl, arbitrary hydrogen may be replaced by fluorine, and arbitrary —CH$_2$— may be replaced by —O—;

ring $D^1$, ring $D^2$ and ring $D^3$ are each independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and $Z^{28}$, $Z^{29}$, $Z^{30}$, $Z^{31}$ and $Z^{32}$ are each independently —C≡C—, —COO—, —(CH$_2$)$_2$—, —CH═CH— or a single bond.

(11) The liquid crystal composition according to item 7, wherein the liquid crystal composition further comprises at least one compound selected from the group consisting of compounds represented by formula (5) in item 8.

(12) The liquid crystal composition according to item 7, wherein the liquid crystal composition further comprises at least one compound selected from the group consisting of compounds represented by formulae (11), (12) and (13) in item 10.

(13) The liquid crystal composition according to item 8, wherein the liquid crystal composition further comprises at least one compound selected from the group consisting of compounds represented by formulae (11), (12) and (13) in item 10.

(14) The liquid crystal composition according to item 9, wherein the liquid crystal composition further comprises at least one compound selected from the group consisting of compounds represented by formulae (11), (12) and (13) in item 10.

(15) The liquid crystal composition according to any one of items 6 to 14, wherein the liquid crystal composition further comprises at least one optically active compound.

(16) The liquid crystal composition according to any one of items 6 to 15, wherein the liquid crystal composition further comprises at least one compound selected from an antioxidant and an ultraviolet absorbent.

(17) A liquid crystal display device comprising at least one of the liquid crystal composition according to any one of items 6 to 16.

According to the invention, such a liquid crystal compound is provided that not only has a negatively large dielectric anisotropy (Δε), but also has at least one of characteristics including a stability to heat, light and so forth, a high clear point, a suitable refractive index anisotropy (Δn) and a good compatibility with other liquid crystal compounds According to the invention, such a liquid crystal composition is provided that has a low viscosity, a suitable refractive index anisotropy (Δn), a suitable negative dielectric anisotropy (Δε) and a low threshold voltage, and also has at least one of characteristics including a high maximum temperature of a nematic phase and a low minimum temperature of a nematic phase. According to the invention, such a liquid crystal display device is provided that has at least one of characteristics including a short response time, a small electric power consumption, a small driving voltage and a large contrast, and capability of being used in a wide temperature range.

The invention will be described in detail below.

The liquid crystal compound of the invention is represented by formula (1-1) or (1-2):

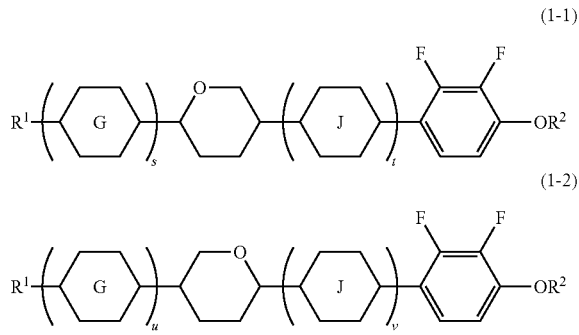

In formulae (1-1) and (1-2), $R^1$ is alkenyl having 2 to 10 carbons. In the alkenyl, arbitrary —$CH_2$— may be replaced by —O—, —S—, —CO— or —$SiH_2$—, provided that plural —$CH_2$— adjacent to each other are not replaced simultaneously. In consideration of stability of the compound, it is not preferred that two oxygen atoms are adjacent to each other.

Examples of $R^1$ include alkenyl having 2 to 10 carbons, alkenyloxy having 2 to 9 carbons, alkenyloxyalkyl having 3 to 9 carbons and alkoxyalkenyl having 3 to 9 carbons. The alkyl chain in these groups is preferably a linear chain. In the case where the alkyl chain is a linear chain, the temperature range of a liquid crystal phase of the compound can be enhanced, and the viscosity of the compound can be decreased. The alkenyl preferably has the double bond at an odd number position thereof, and preferably has a trans configuration. In the case where the alkenyl has plural double bonds, they are preferably not conjugated.

Examples of the alkenyl include —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —CH=CH$(CH_2)_2$CH=$CH_2$ and —$(CH_2)_2$CH=CH$(CH_2)_2$CH=$CH_2$.

Examples of the alkenyloxy include —$OCH_2$CH=$CH_2$, —$OCH_2$CH=$CHCH_3$ and —$OCH_2$CH=$CHC_2H_5$.

Examples of alkenyloxyalkyl include —$CH_2OCH_2$CH=$CH_2$, —$CH_2OCH_2$CH=$CHCH_3$ and —$(CH_2)_2O(CH_2)_2$CH=$CH_3$.

Examples of the alkoxyalkenyl include —CH=$CHCH_2OCH_3$, —CH=$CHCH_2OC_2H_5$ and —$CH_2$CH=$CHCH_2OCH_3$.

Preferred examples of $R^1$ among these include —CH=$CH_2$, —CH=$CHCH_3$, —CH=$CHC_2H_5$, —$(CH_2)_2$CH=$CH_2$, —CH=$CHC_3H_7$, —$(CH_2)_2$CH=$CHCH_3$, —CH=CH$(CH_2)_2$CH=$CH_2$, and —$(CH_2)_2$CH=CH$(CH_2)_2$CH=$CH_2$.

More preferred examples of $R^1$ include —CH=$CH_2$, —CH=$CHCH_3$, —CH=$CHC_2H_5$, —$(CH_2)_2$CH=$CH_2$, —CH=$CHC_3H_7$ and —$(CH_2)_2$CH=$CHCH_3$.

$R^2$ is alkyl having 1 to 10 carbons. In the alkyl having 2 to 10 carbons, arbitrary —$CH_2$— may be replaced by —O—, —S—, —CO— or —$SiH_2$—, provided that plural —$CH_2$— adjacent to each other are not replaced simultaneously, and arbitrary —$(CH_2)_2$— may be replaced by —CH=CH— or —C≡C—. In consideration of stability of the compound, it is not preferred that two oxygen atoms are adjacent to each other.

Examples of $R^2$ include alkyl having 1 to 10 carbons, alkoxyalkyl having 2 to 9 carbons, alkenyl having 2 to 10 carbons, alkenyloxyalkyl having 3 to 9 carbons and alkoxyalkenyl having 3 to 9 carbons. The alkyl chain in these groups is preferably a linear chain. In the case where the alkyl chain is a linear chain, the temperature range of a liquid crystal phase of the compound can be enhanced, and the viscosity of the compound can be decreased. In the case where the alkenyl has the double bond at an odd number position thereof, the alkenyl preferably has a cis configuration. In the case where the alkenyl has the double bond at an even number position thereof, the alkenyl preferably has a trans configuration. In the case where the alkenyl has plural double bonds, they are preferably not conjugated. $R^2$ is preferably not alkoxy from the point of stability of the compound since oxygen atoms are adjacent to each other.

Examples of the alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$C_{10}H_{21}$.

Examples of the alkoxyalkyl include —$CH_2OCH_3$, —$CH_2OC_2H_5$, —$(CH_2)_2OCH_3$ and —$(CH_2)_2OC_2H_5$.

Examples of the alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$CH=$CH_2$, —CH=$CHC_3H_7$, —$CH_2$CH=$CHC_2H_5$, —$(CH_2)_2$CH=$CHCH_3$, —$(CH_2)_3$CH=$CH_2$.

Examples of alkenyloxyalkyl include —$CH_2OCH_2$CH=$CH_2$, —$CH_2OCH_2$CH=$CHCH_3$, and —$(CH_2)_2O(CH_2)_2$CH=$CH_3$.

Examples of the alkoxyalkenyl include —CH=$CHCH_2OCH_3$, —CH=$CHCH_2OC_2H_5$ and —$CH_2$CH=$CHCH_2OCH_3$.

Preferred examples of $R^2$ among these include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —CH=$CH_2$, —$CH_2$CH=$CHCH_3$, —$(CH_2)_2$CH=$CH_2$, —$CH_2$CH=$CHC_2H_5$, —$(CH_2)_2$CH=$CHCH_3$ and —$(CH_2)_3$CH=$CH_2$.

More preferred examples of $R^2$ include —$CH_3$, —$C_2H_5$, —$C_3H_7$, —$C_4H_9$, —$C_5H_{11}$ and —$C_6H_{13}$.

In formulae (1-1) and (1-2), ring G and ring J are each independently 1,4-cyclohexylene or 1,4-phenylene. In the rings, arbitrary —$CH_2$— may be replaced by —O—, —S—, —CO— or —$SiH_2$—, and arbitrary —$(CH_2)_2$— may be replaced by —CH=CH—. In the 1,4-phenylene, arbitrary —CH= may be replaced by —N=.

In the case where these rings are each 1,4-cyclohexylene, the refractive index anisotropy (Δn) of the compound can be decreased, the viscosity of the compound can be decreased, and the maximum temperature of a nematic phase of a liquid crystal composition, to which the compound is added, can be increased.

In the case where these rings are each 1,4-phenylene, the refractive index anisotropy (Δn) of the compound can be relatively increased, and the orientation order parameter can be increased.

Preferred examples of ring G and ring J among these include 1,4-cyclohexylene, 1,4-cyclohexenylene, 1,3-dioxan-2,5-diyl, 1,4-phenylene and 1,3-pyrimidin-2,5-yl, and more preferred examples thereof include 1,4-cyclohexylene and 1,4-phenylene.

In formulae (1-1) and (1-2), s and t are each independently 0, 1, 2 or 3, provided that the sum of s and t is 1, 2 or 3. The sum of s and t is preferably 1 or 2 since the compatibility with other liquid crystal compounds is enhanced when the number of the rings is decreased.

In formulae (1-1) and (1-2), u is 0, 1 or 2, and v is 1, 2, or 3, provided that the sum of u and v is 1, 2, or 3. v is preferably 1, 2 or 3 since the compound represented by formula (1-2), wherein v=0, has a small absolute value of a dielectric anisotropy (Δε). The sum of u and v is preferably 1 or 2 since the compatibility with other liquid crystal compounds is enhanced when the number of the rings is decreased.

In the case where s is 2 or 3, and u is 2, plural rings represented by ring G may be the same as or different from each other. In the case where t and v are each 2 or 3, plural rings represented by ring J may be the same as or different from each other.

When v is 0 in formula (1-2), the absolute value of the dielectric anisotropy (Δε) is decreased. This is because in the structure represented by formula (A), the oxygen of the tetrahydropyran ring and fluorines of 2,3-difluoro-1,4-phenylene are directed directions opposite to each other, respectively, in the stable conformation, whereby the dipole moments are balanced out each other to decrease the dielectric anisotropy (Δε). In view of the factors, v is preferably 1, 2 or 3.

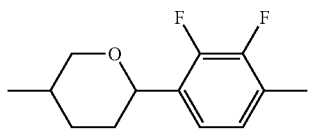

(A)

In the liquid crystal compound represented by formula (1-1) or (1-2), the terminal groups $R^1$ and $R^2$ and the rings G and J may be appropriately selected from the aforementioned ranges, thereby controlling suitably the characteristics including the refractive index anisotropy (Δn) and the dielectric anisotropy (Δε).

The liquid crystal compound represented by formula (1-1) or (1-2) of the invention can be obtained by introducing appropriate groups for $R^1$, $R^2$, ring G and ring J, and the groups can be introduced according to known ordinary organic synthesis methods. Representative examples of the synthesis methods include the methods described in Shin Jikken Kagaku Kouza (New Experimental Chemistry Course), vol. 14, Synthesis and Reaction of Organic Compounds (Maruzen, Inc. (1978), or the fourth edition Jikken Kagaku Kouza (Experimental Chemistry Course), vols. 19 to 26, Organic Synthesis I to VIII (Maruzen, Inc. (1991)) and so forth.

An example of a method for bonding the ring will be described by schemes, and the schemes will be then described. In the scheme, $MSG^1$ and $MSG^2$ are each a monovalent organic group having at least one ring. Plural groups represented by $MSG^1$ (or $MSG^2$) used in the scheme may be the same as or different from each other. The compound (1A) in the scheme corresponds to the liquid crystal compound represented by formula (1-1) or (1-2).

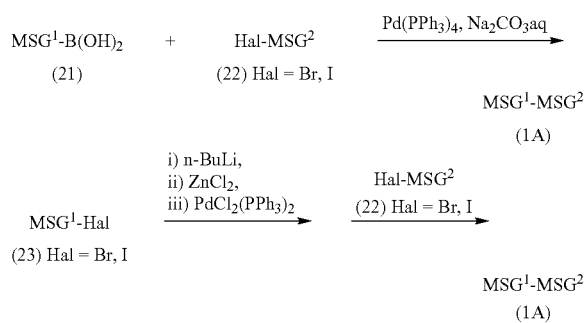

Aryl borate (21) and a compound (22) synthesized by a known method are reacted with each other in the presence of a carbonate salt aqueous solution and a catalyst, such as tetrakis(triphenylphosphine)palladium, to synthesize a compound (1A) The compound (1A) can be also synthesized by reacting a compound (23) synthesized by a known method with n-butyl lithium and then with zinc chloride, and then reacted with the compound (22) in the presence of a catalyst, such as dichlorobis(triphenylphosphine)palladium.

An example of a method for synthesizing the tetrahydropyran compound represented by formula (1-1) will be described by schemes. A scheme for synthesizing a synthetic intermediate (27) having alactone skeleton will be described, and then an example of a method for synthesizing a tetrahydropyran compound (30) by using the synthetic intermediate (27) as a starting material will be described.

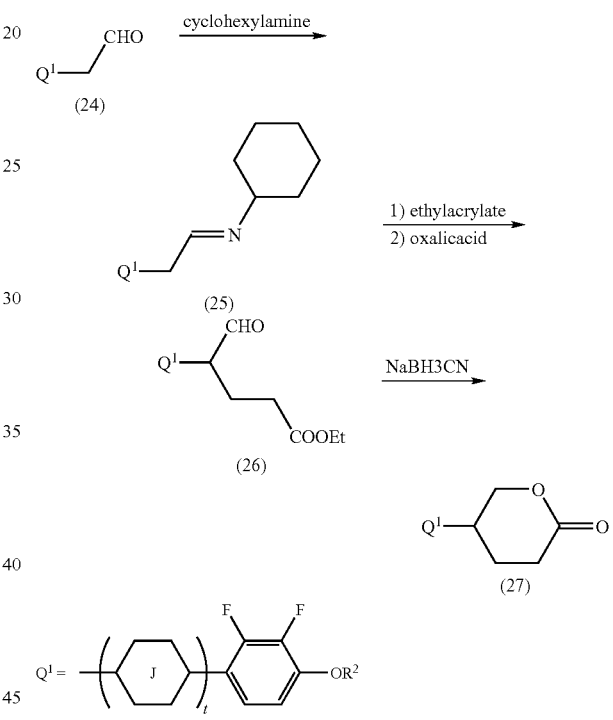

In the compounds (24) to (27), $Q^1$ is a structural unit of formula (1-1). The structural unit is shown in the scheme. In the compounds, symbols $R^2$, J and t have the same meanings as in formula (1-1) or (1-2).

Specifically, the compound (25) is synthesized by reaction between the compound (24) and cyclohexylamine. The reaction is preferably performed in a solvent, such as diethyl ether, in the presence of a base, such as potassium carbonate at a temperature in a range of from room temperature to the boiling point of the solvent. The compound (26) is synthesized by adding ethyl acrylate to the compound (25) and then deprotecting the compound. In the reaction, ethyl acrylate itself is preferably used as a solvent, and a solvent, such as toluene, that is not reacted with the compound (25) and ethyl acrylate may be used. For preventing ethyl acrylate from being polymerized, a polymerization inhibitor, such as hydroquinone, is preferably added. The reaction is performed at a temperature of from room temperature to the boiling point of the solvent upon using an ordinary glass reactor, and the reaction may be performed at a temperature higher than the boiling point of the solvent by using a pressure-proof reactor, such as a stainless steel autoclave. After performing the addition reaction sufficiently, an acid, such as oxalic acid, is added to the reaction system to eliminate cyclohexylamine, thereby providing the compound (26). The compound (27) is synthesized by subjecting the compound (26) to ring-opening reaction. The reaction is generally performed in a solvent, such as isopropanol, in the presence of sodium cyanoborohydride at a temperature around room temperature. An acid, such as hydrochloric acid, may be added for accelerating the reaction.

The compound (24) as a starting material can be easily synthesized by a known organic chemical synthesis method.

An example of a synthesis method of a compound (30) will be described.

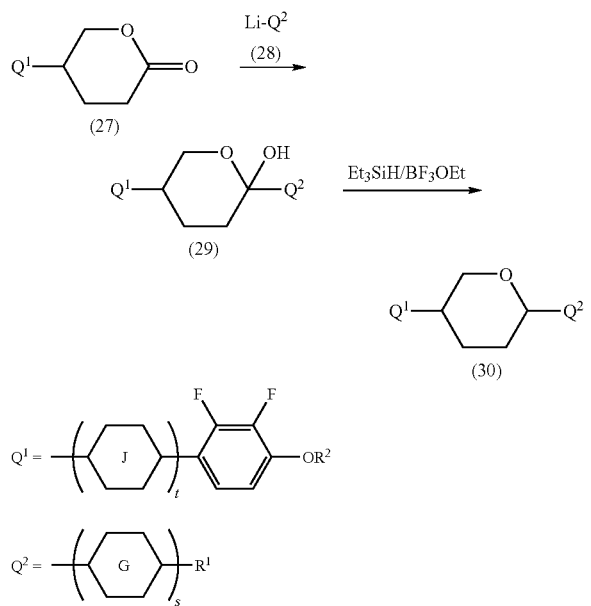

In the compounds (27) to (30), $Q^1$ and $Q^2$ are each a structural unit of formula (1-1). The structural unit is shown in the scheme. In the compounds, symbols $R^1$, $R^2$, G, J, s and t have the same meanings as in formula (1-1) or (1-2).

Specifically, the compound (29) is synthesized by reaction between the compounds (27) and (28). The reaction is preferably performed in a solvent, such as tetrahydrofuran, at a temperature of −30° C. The compound (30) is synthesized by reacting the compound (29) in a solvent, such as dichloromethane, in the presence of triethylsilane and boron trifluoride diethyl ether at a temperature of −50° C.

The compound (28) as a starting material can be easily synthesized by a known organic chemical synthesis method.

The tetrahydropyran compound represented by formula (1-2) can be synthesized by the similar method as above.

The liquid crystal composition of the invention necessarily contains the compound represented by formula (1-1) or (1-2) of the invention as a component A. The liquid crystal composition of the invention may be a composition containing only the component A or may contain the component A and another component that is not specifically shown herein. The liquid crystal composition of the invention can exhibit various characteristics by adding thereto a component B containing at least one compound selected from the group consisting of the compounds represented by formulae (2), (3) and (4), a component C containing at least one compound selected from the group consisting of the compounds represented by formula (5), a component D containing at least one compound selected from the group consisting of the compounds represented by formulae (6), (7), (8), (9) and (10), and a component E containing at least one compound selected from the group consisting of the compounds represented by formulae (11), (12) and (13).

The components may be arbitrarily combined depending on the characteristics and purposes of the target composition, and preferred examples of the combination of the components include a combination of the components A and B, a combination of the components A and C, a combination of the components A and D, a combination of the components A, B and E, a combination of the components A, C and E, and a combination of the components A, D and E.

The components of the liquid crystal composition of the invention may be analogues thereof containing isotopes of the elements constituting the components since there is no large physical difference among them.

In the component B, preferred examples of the compound represented by formula (2) include compounds represented by formulae (2-1) to (2-16), preferred examples of the compound represented by formula (3) include compounds represented by formulae (3-1) to (3-112), and preferred examples of the compound represented by formula (4) include compounds represented by formulae (4-1) to (4-52).

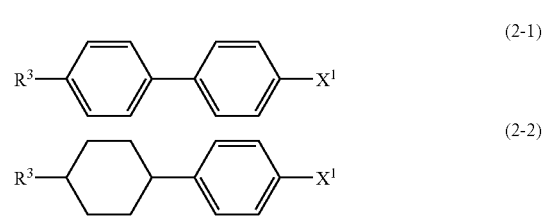

(2-1)

(2-2)

(2-3)

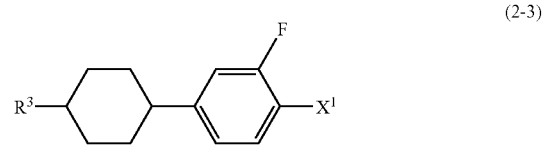

(2-4)

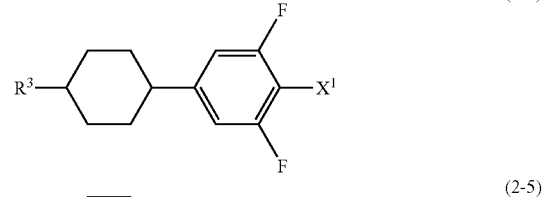

(2-5)

(2-6)

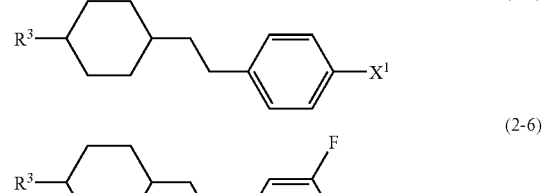

(2-7)

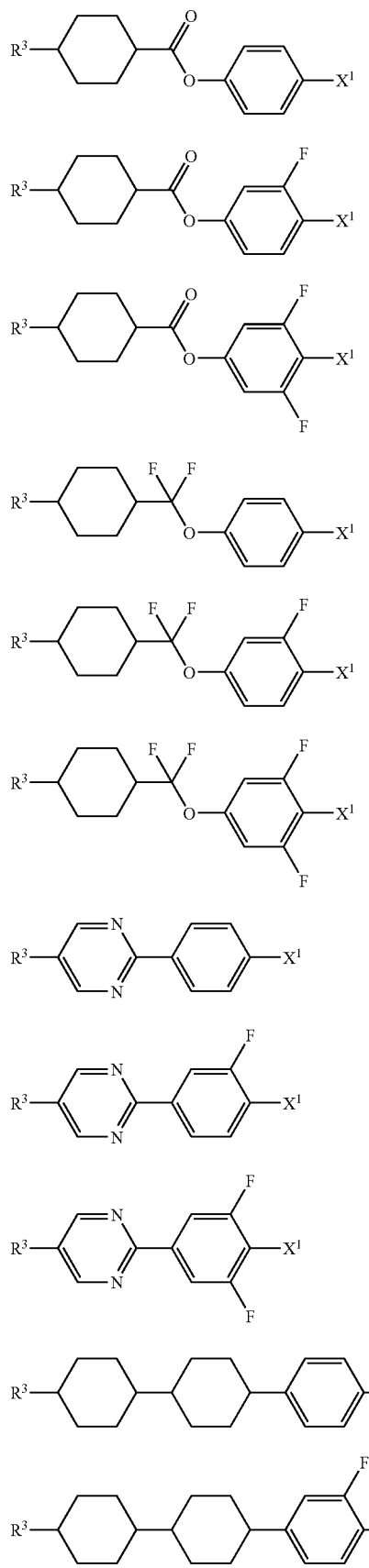
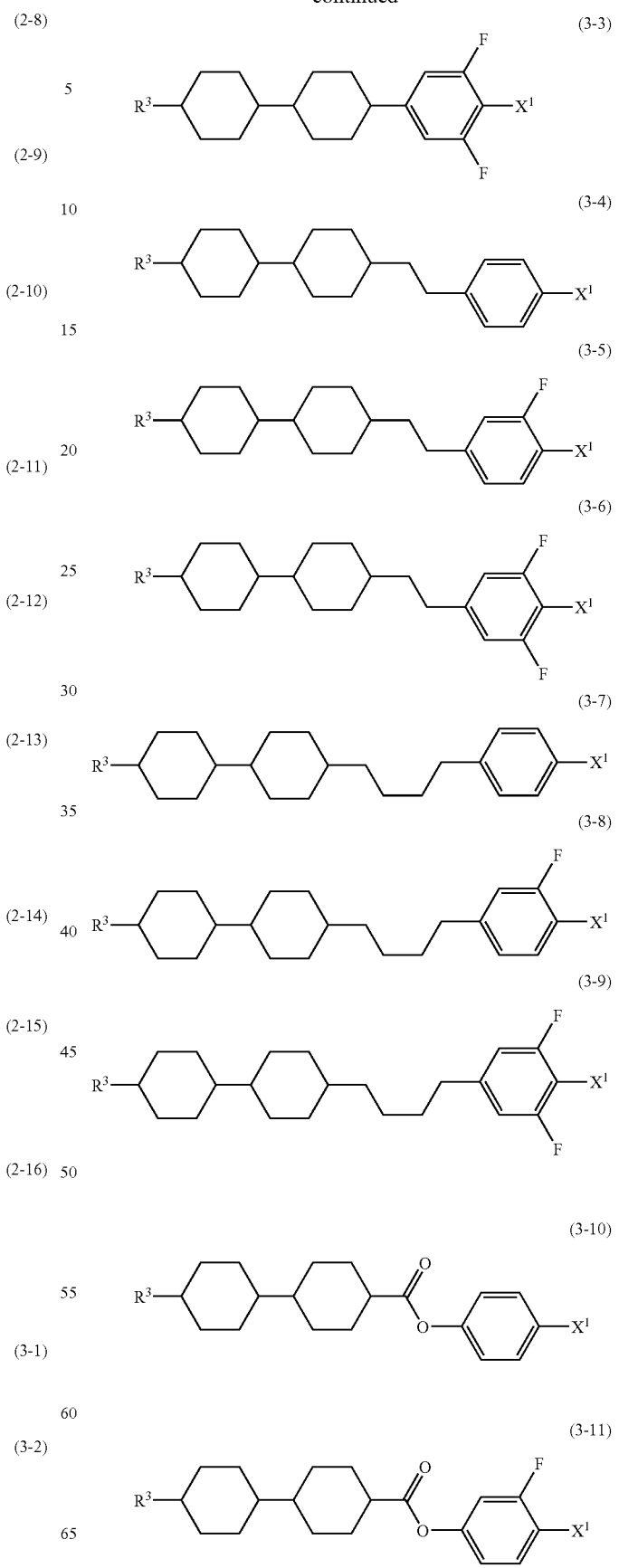

(3-12)
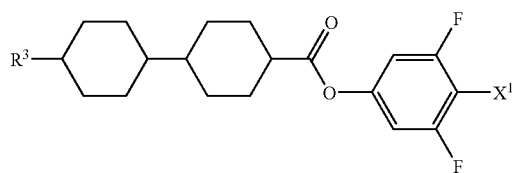
(3-13)
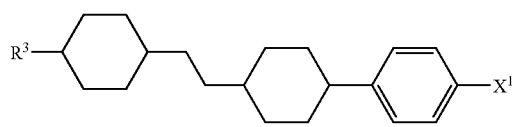
(3-14)
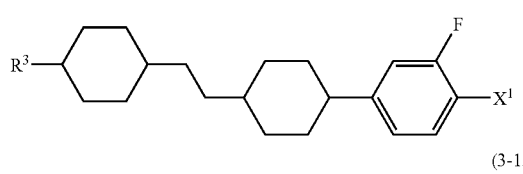
(3-15)
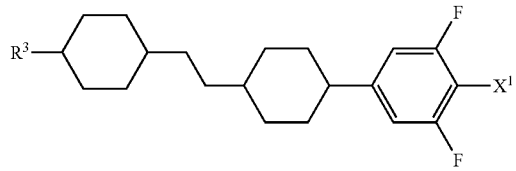
(3-16)
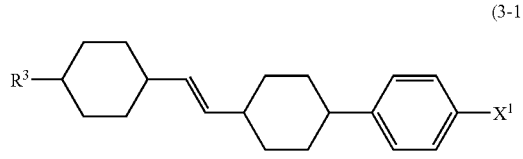
(3-17)
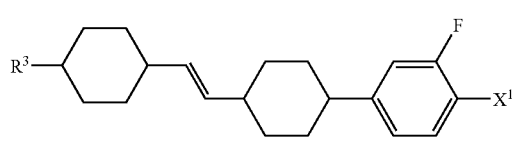
(3-18)
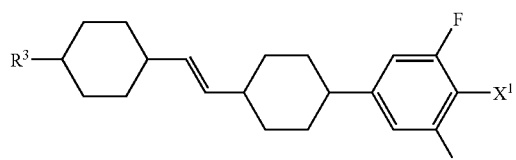
(3-19)
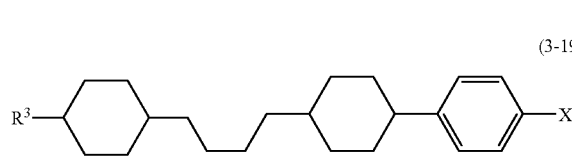
(3-20)
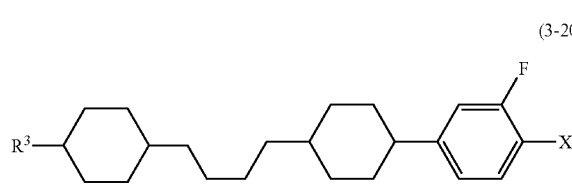
(3-21)
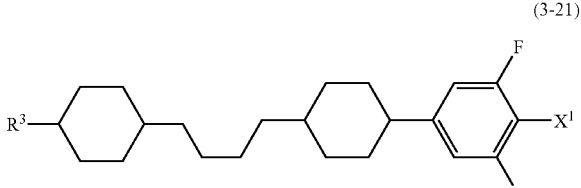
(3-22)
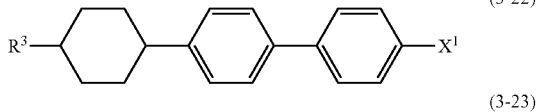
(3-23)
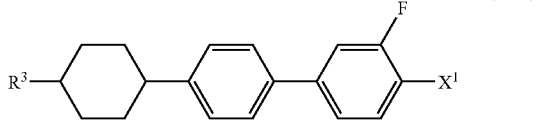
(3-24)
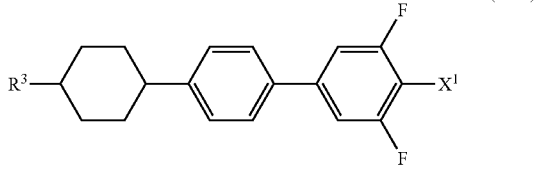
(3-25)
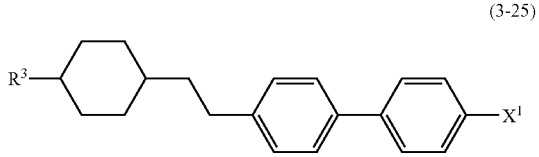
(3-26)
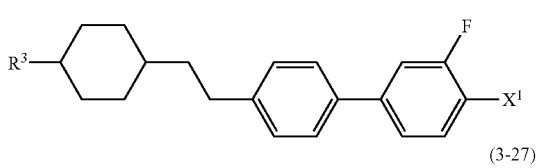
(3-27)
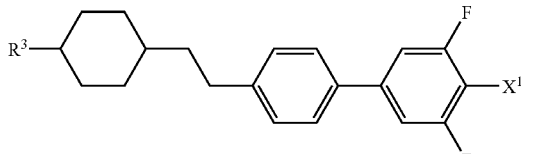
(3-28)
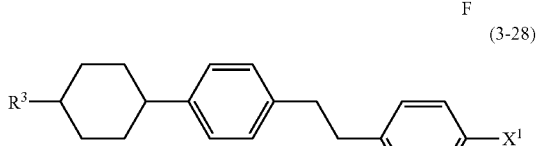
(3-29)
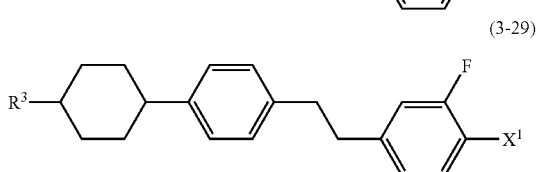
(3-30)
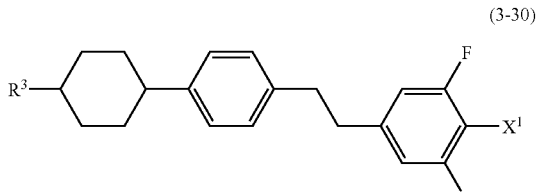

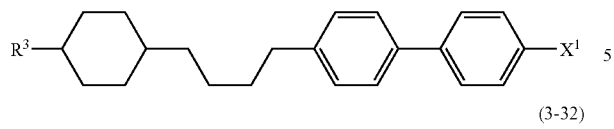
(3-31)
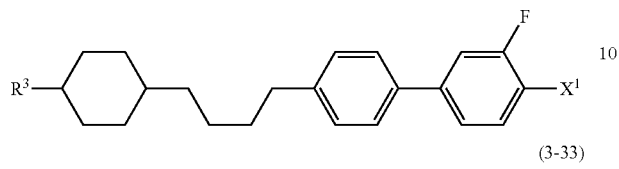
(3-32)
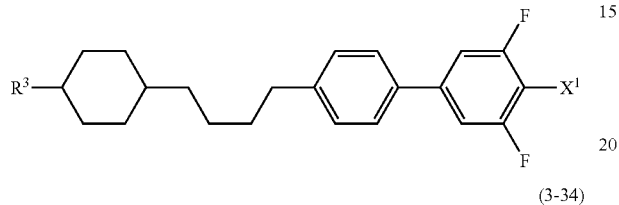
(3-33)
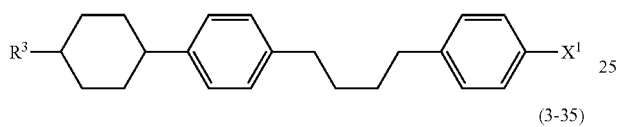
(3-34)
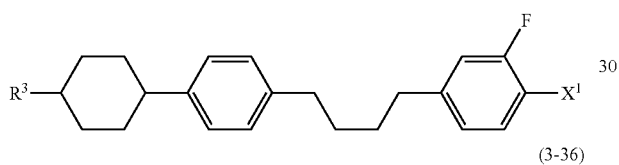
(3-35)
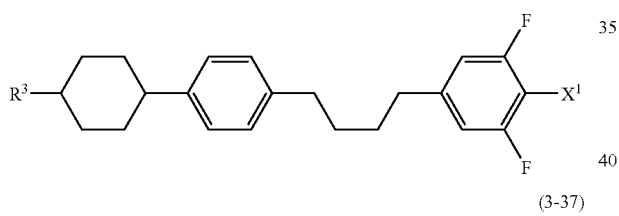
(3-36)
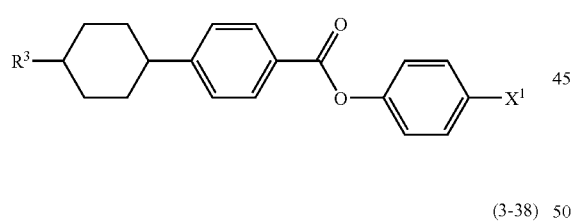
(3-37)
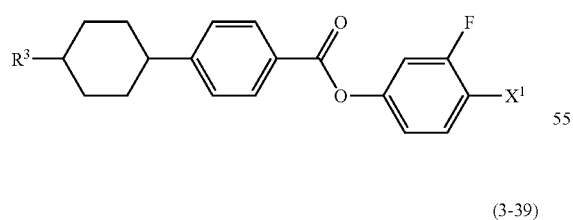
(3-38)
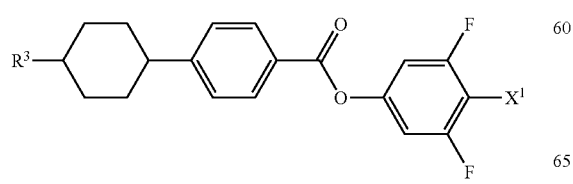
(3-39)
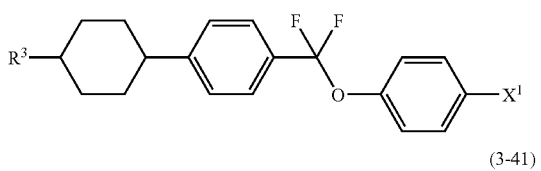
(3-40)
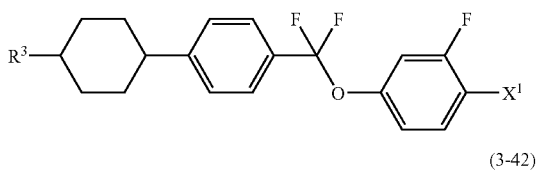
(3-41)
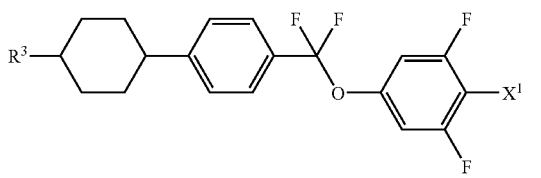
(3-42)
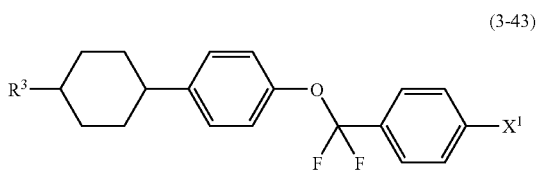
(3-43)
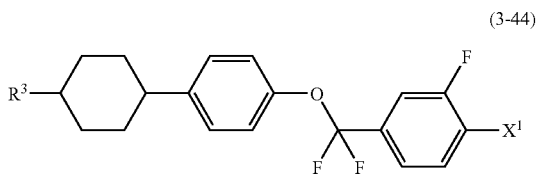
(3-44)
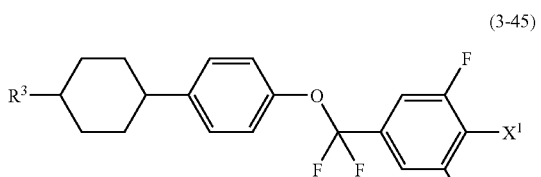
(3-45)
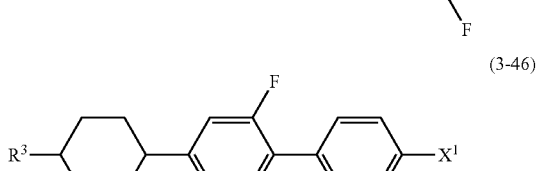
(3-46)
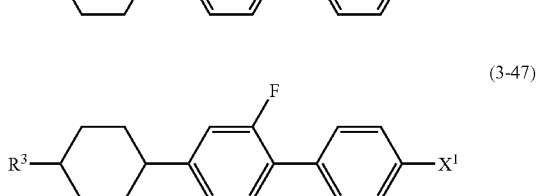
(3-47)
(3-48)

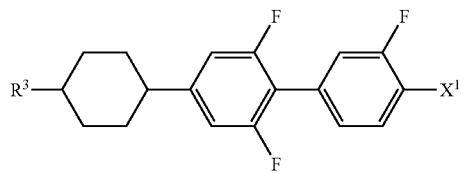
(3-49)
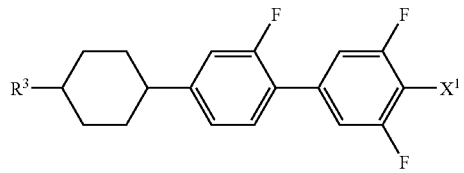
(3-50)
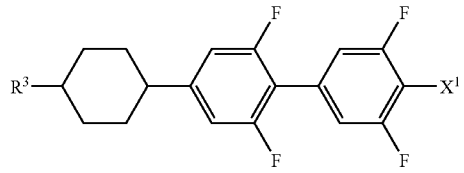
(3-51)
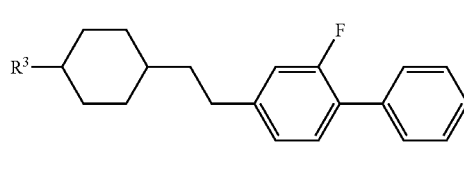
(3-52)
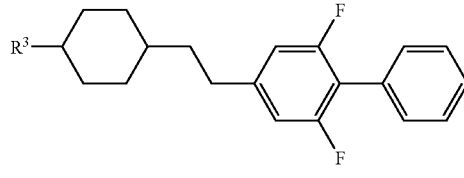
(3-53)
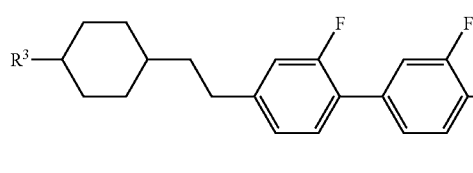
(3-54)
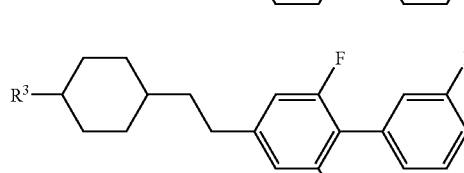
(3-55)
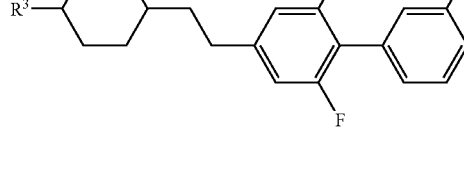
(3-56)
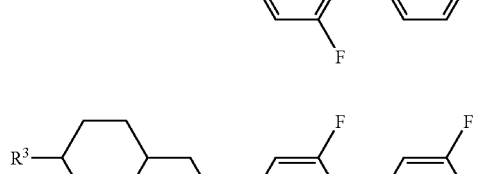
(3-57)
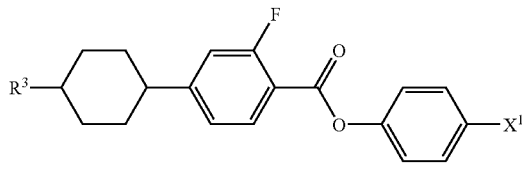
(3-58)
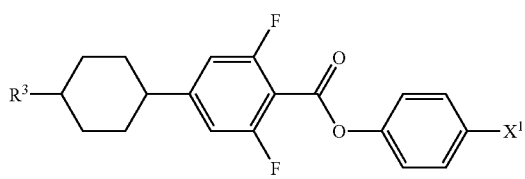
(3-59)
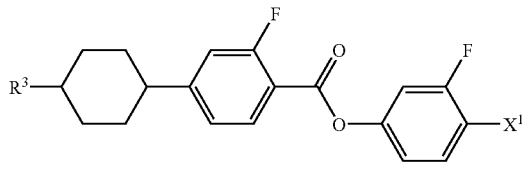
(3-60)
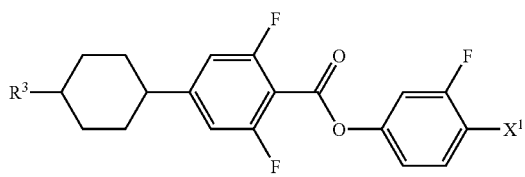
(3-61)
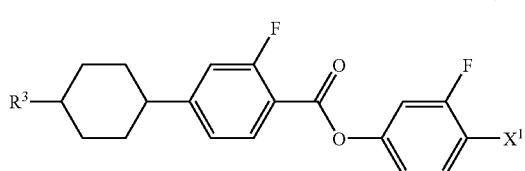
(3-62)
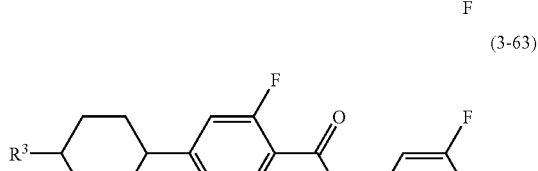
(3-63)
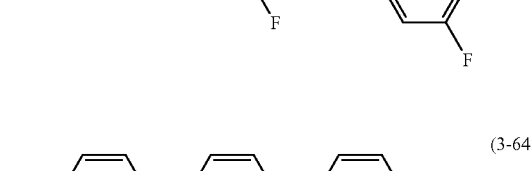
(3-64)
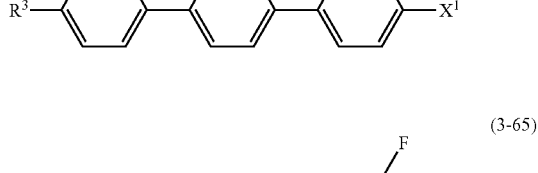
(3-65)

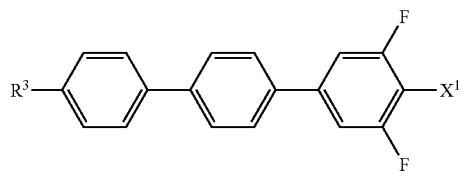
(3-66)
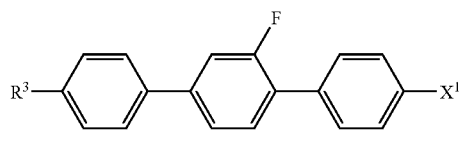
(3-67)
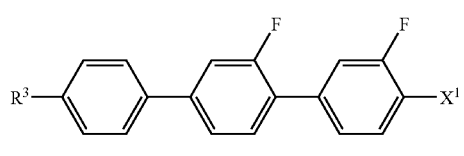
(3-68)
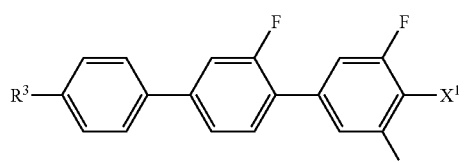
(3-69)
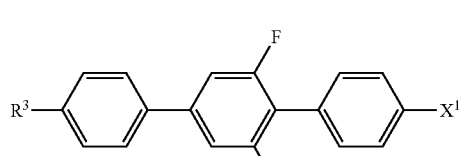
(3-70)
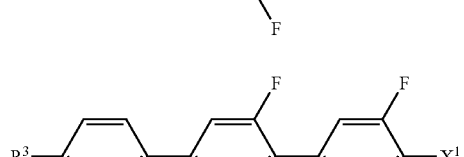
(3-71)
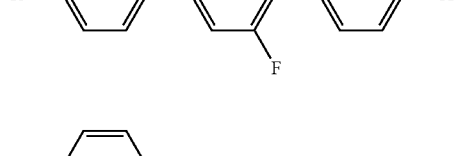
(3-72)
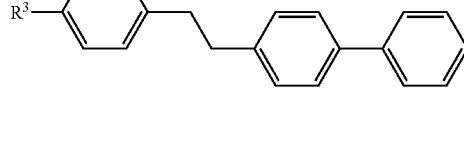
(3-73)
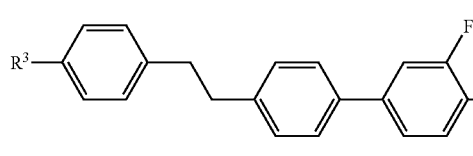
(3-74)
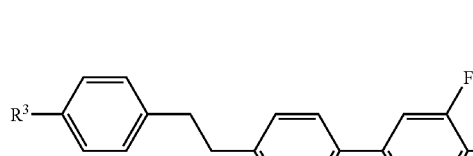
(3-75)
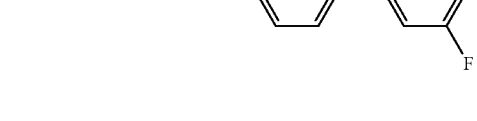
(3-76)
(3-77)
(3-78)
(3-79)
(3-80)
(3-81)
(3-82)
(3-83)

(3-84)
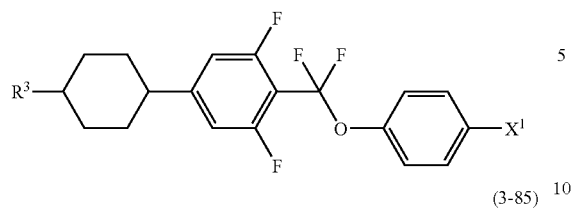
(3-85)
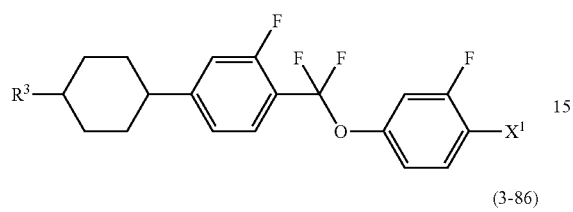
(3-86)
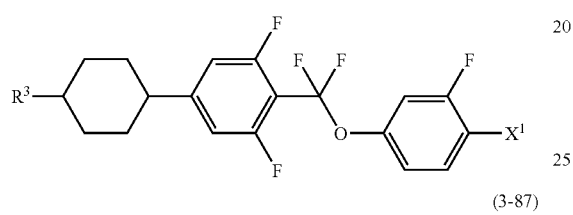
(3-87)
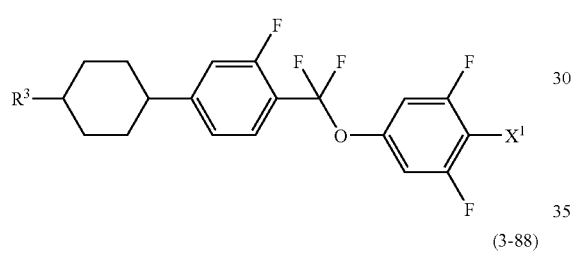
(3-88)
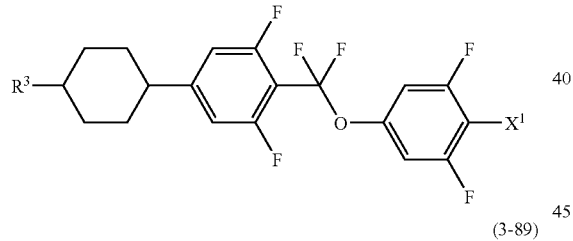
(3-89)
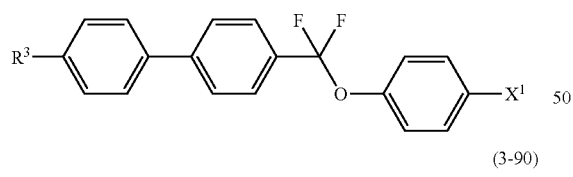
(3-90)
(3-91)
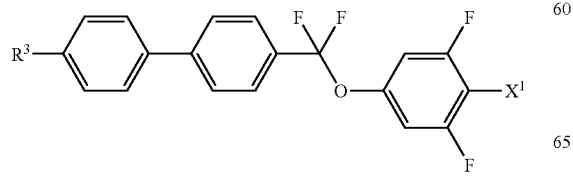
(3-92)
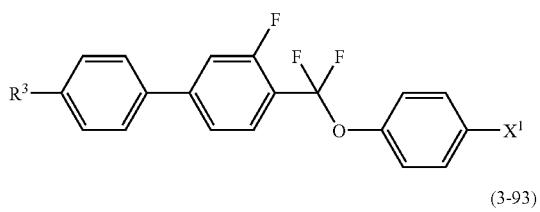
(3-93)
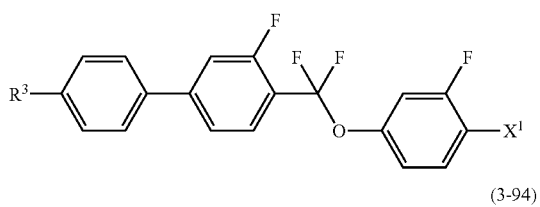
(3-94)
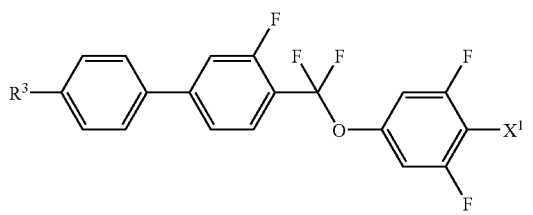
(3-95)
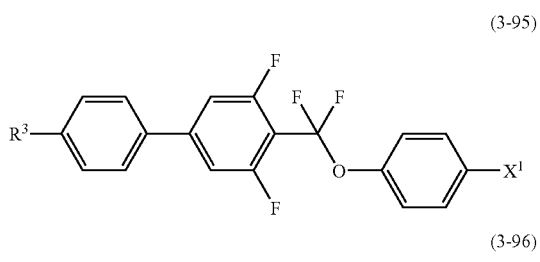
(3-96)
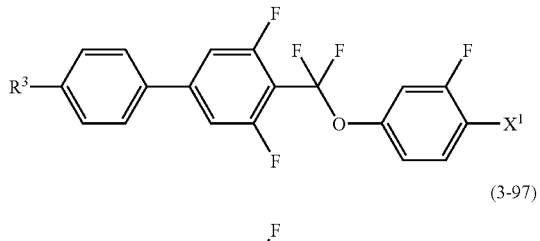
(3-97)
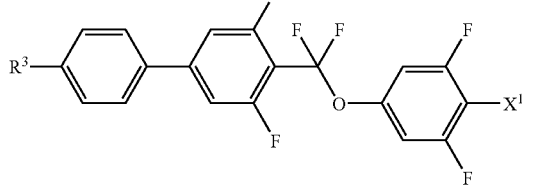
(3-98)
(3-99)
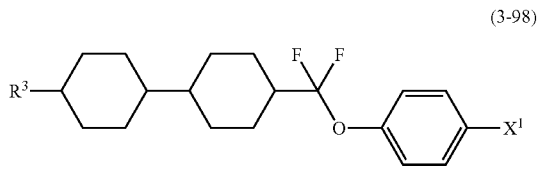

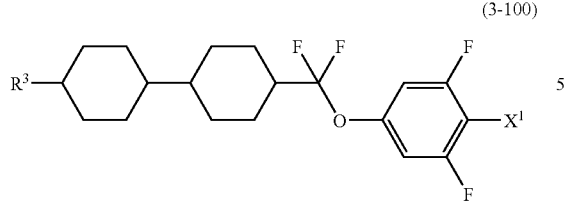 (3-100)
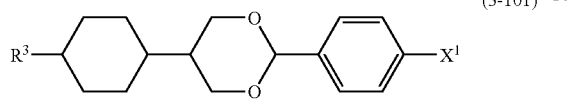 (3-101)
 (3-102)
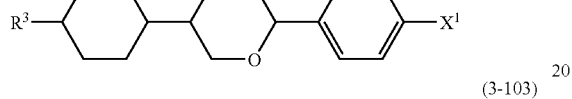 (3-103)
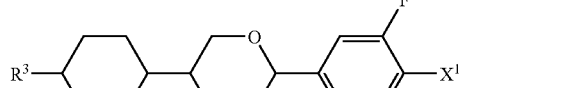 (3-104)
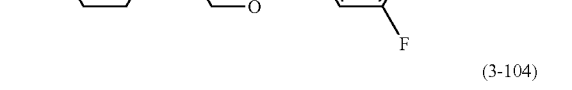 (3-105)
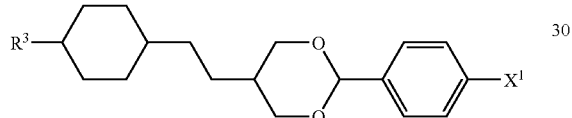 (3-106)
 (3-107)
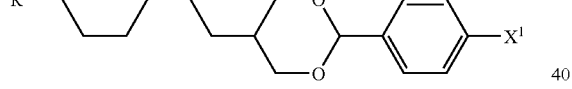 (3-108)
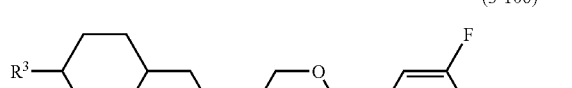 (3-109)
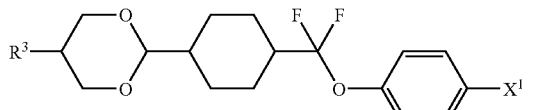 (3-110)
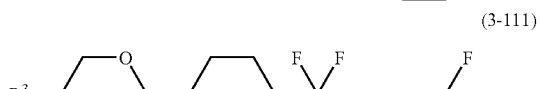 (3-111)
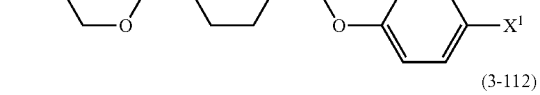 (3-112)
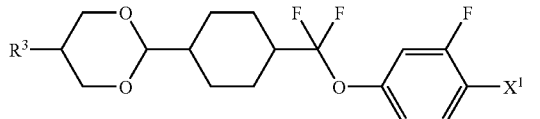 (4-1)
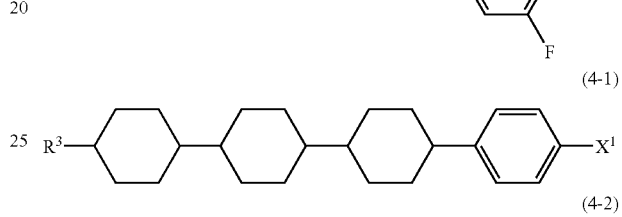 (4-2)
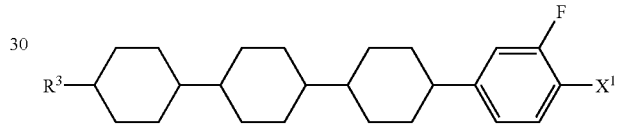 (4-3)
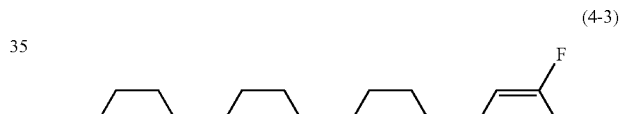 (4-4)
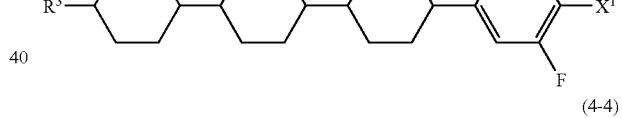 (4-5)
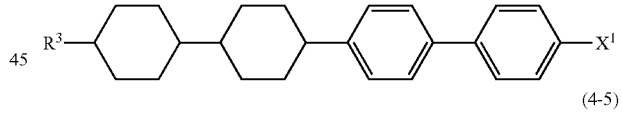 (4-6)
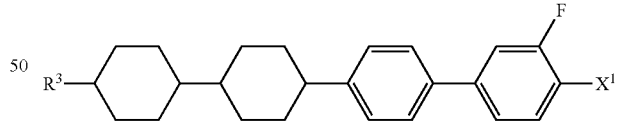 (4-7)

(4-8) 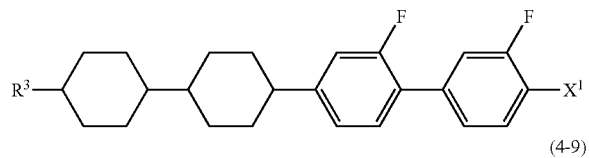
(4-9) 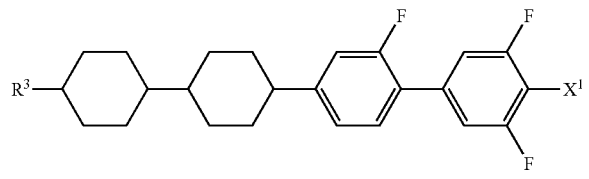
(4-10) 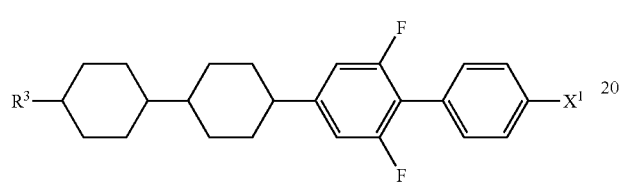
(4-11) 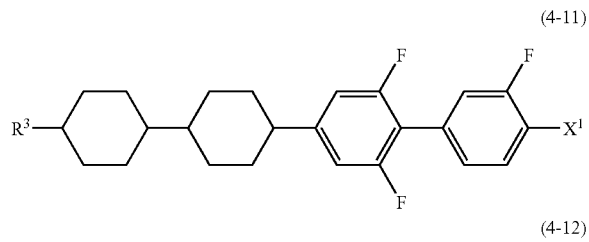
(4-12) 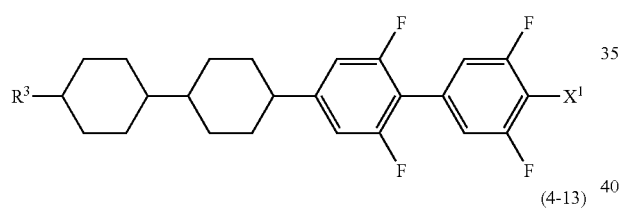
(4-13) 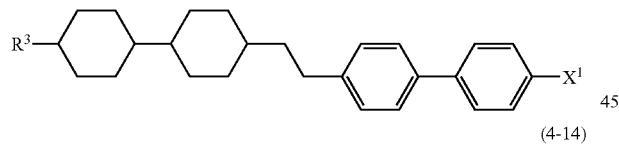
(4-14) 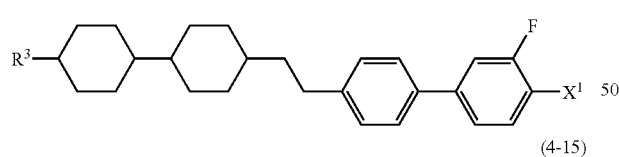
(4-15) 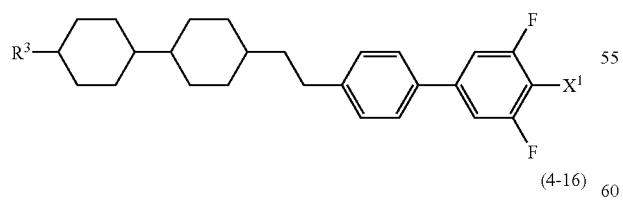
(4-16) 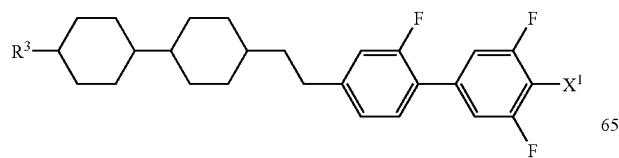
(4-17) 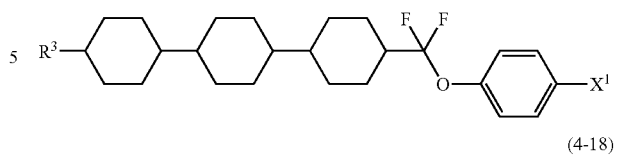
(4-18) 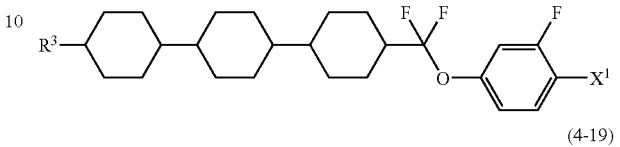
(4-19) 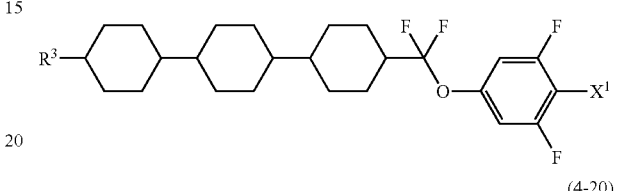
(4-20) 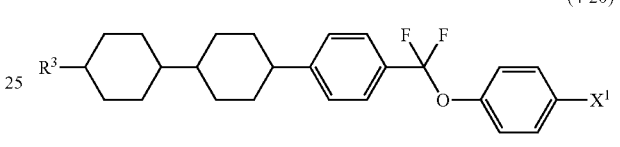
(4-21) 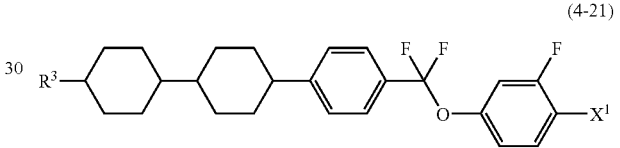
(4-22) 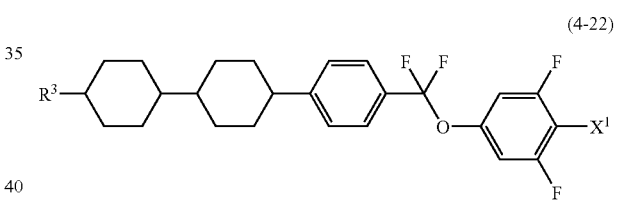
(4-23) 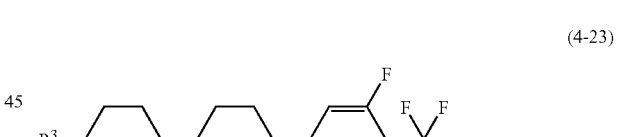
(4-24) 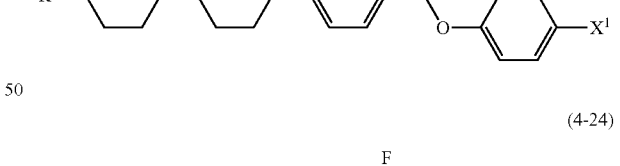
(4-25)

(4-26) 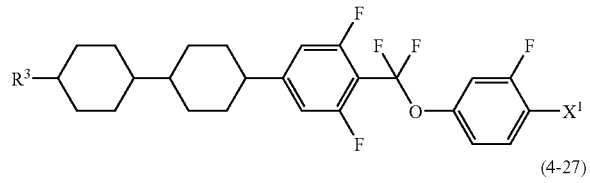
(4-27) 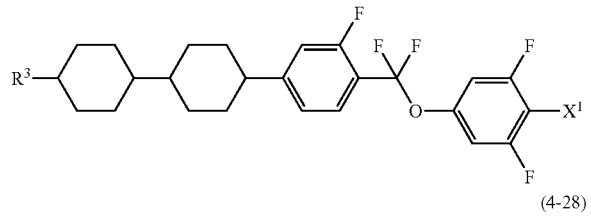
(4-28) 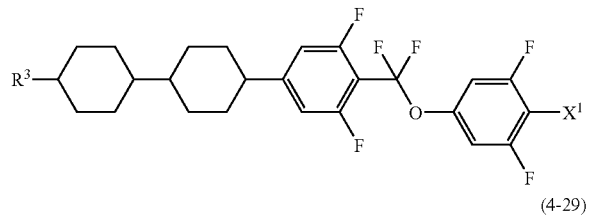
(4-29) 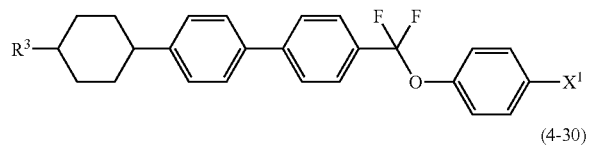
(4-30) 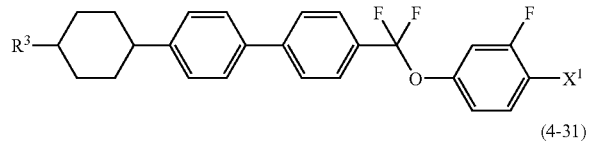
(4-31) 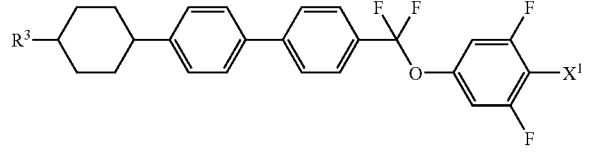
(4-32) 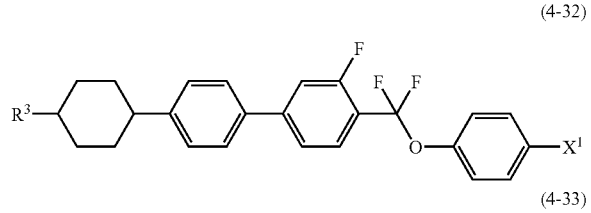
(4-33) 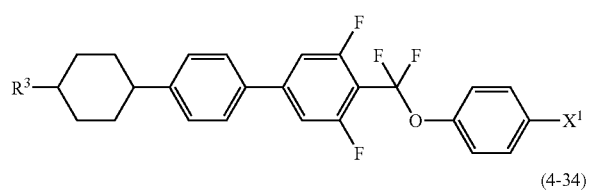
(4-34) 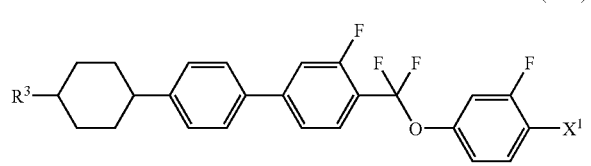
(4-35) 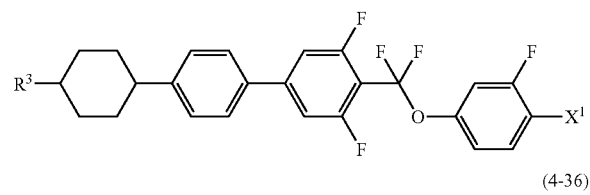
(4-36) 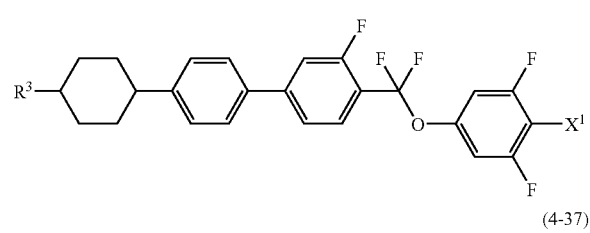
(4-37) 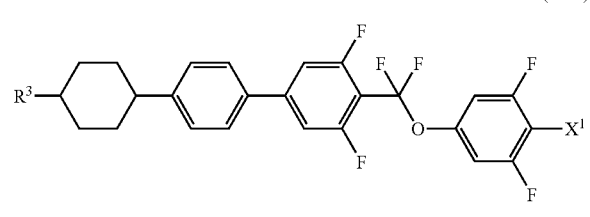
(4-38) 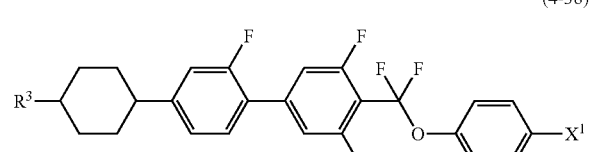
(4-39) 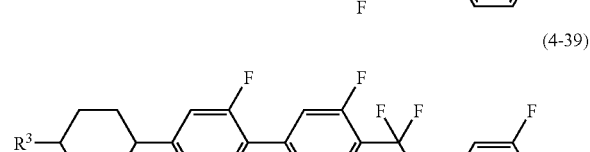
(4-40) 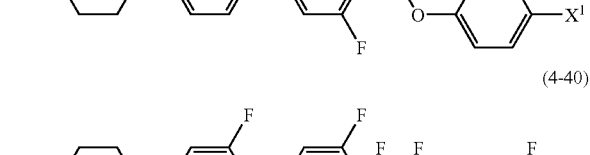
(4-41) 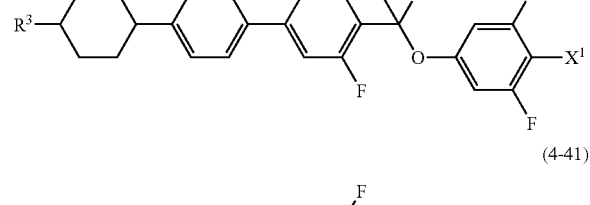
(4-42) 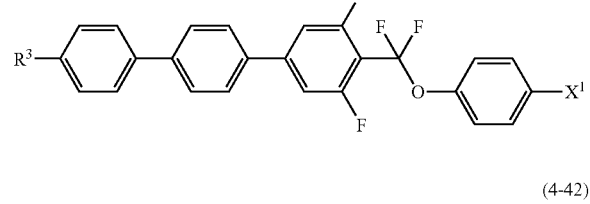
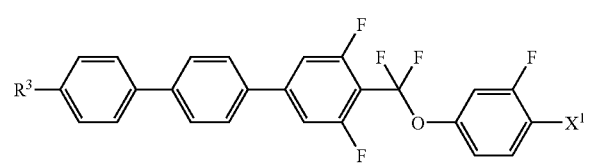

(4-43)
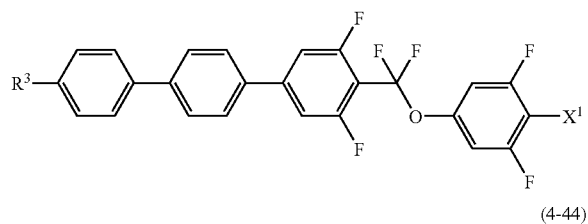

(4-44)
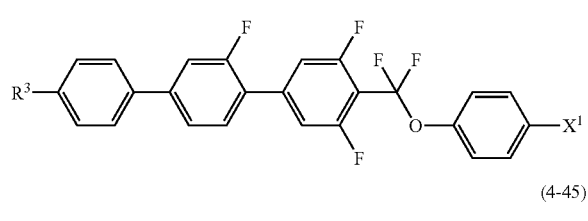

(4-45)
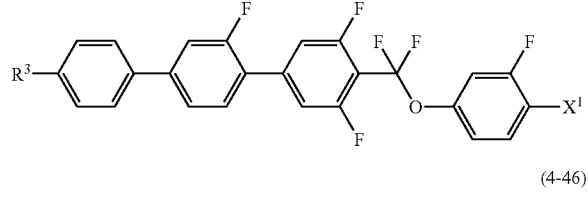

(4-46)
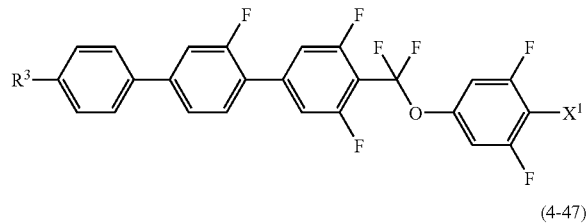

(4-47)
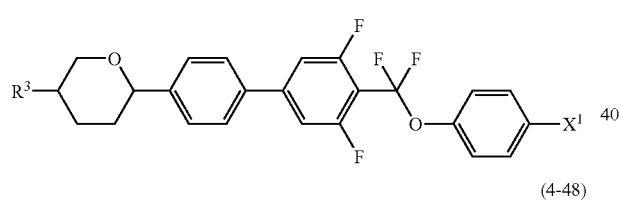

(4-48)
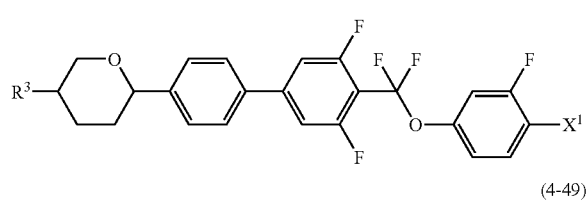

(4-49)
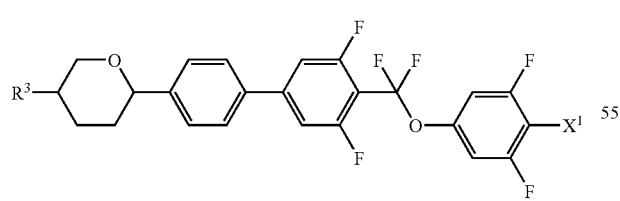

(4-50)
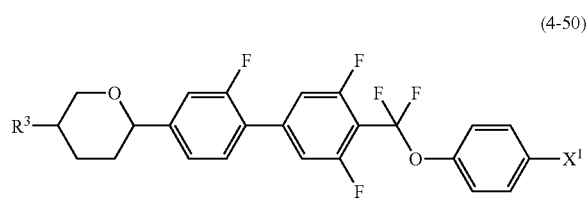

(4-51)
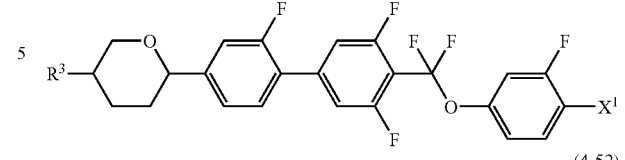

(4-52)
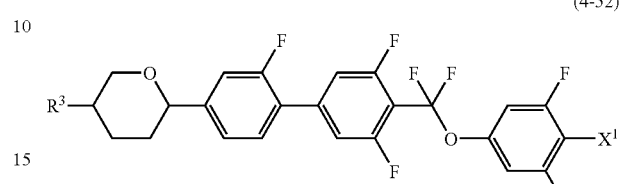

In the formulae (2-1) to (2-16), (3-1) to (3-112), and (4-1) to (4-52), $R^3$ and $X^1$ have the same meanings as described above.

The compound represented by formulae (2) to (4), i.e., the component B, has a positive dielectric anisotropy ($\Delta\epsilon$) and is significantly excellent in heat stability and chemical stability, and thus the compound is used for preparing a liquid crystal composition for a TFT mode device. The content of the component B in the liquid crystal composition of the invention is suitably from approximately 1% to approximately 99% by weight, preferably approximately 10% to approximately 97% by weight, and more preferably from approximately 40% to approximately 95% by weight, based on the total weight of the liquid crystal composition of the invention The viscosity of the composition can be controlled by further adding the compound represented by formulae (11) to (13) (component E).

Preferred examples of the compound represented by formula (5), i.e., the component C, include compounds represented by formulae (5-1) to (5-64).

(5-1)
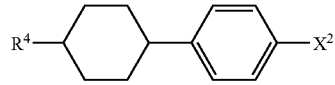

(5-2)

(5-3)
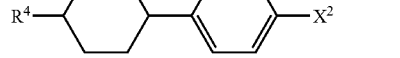

(5-4)
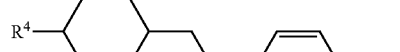

(5-5)

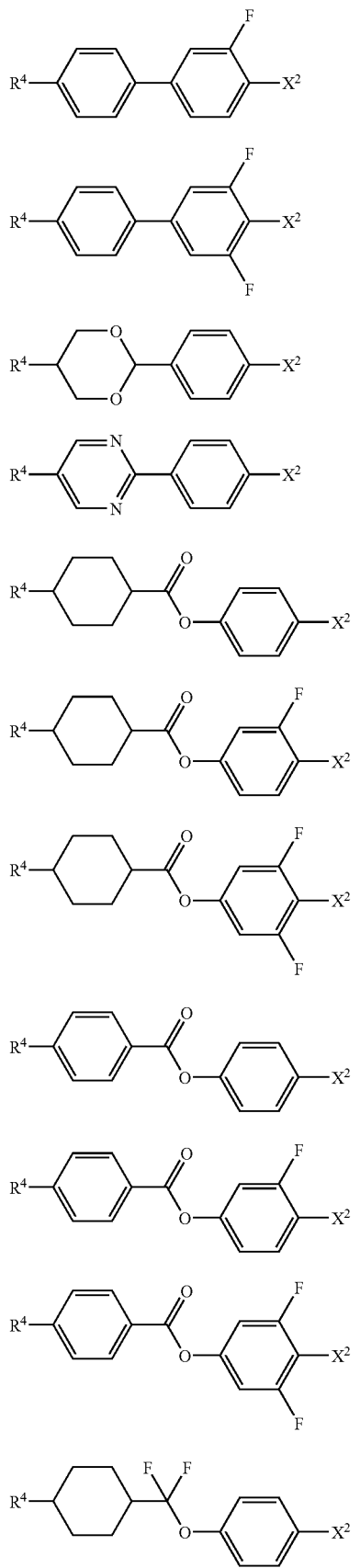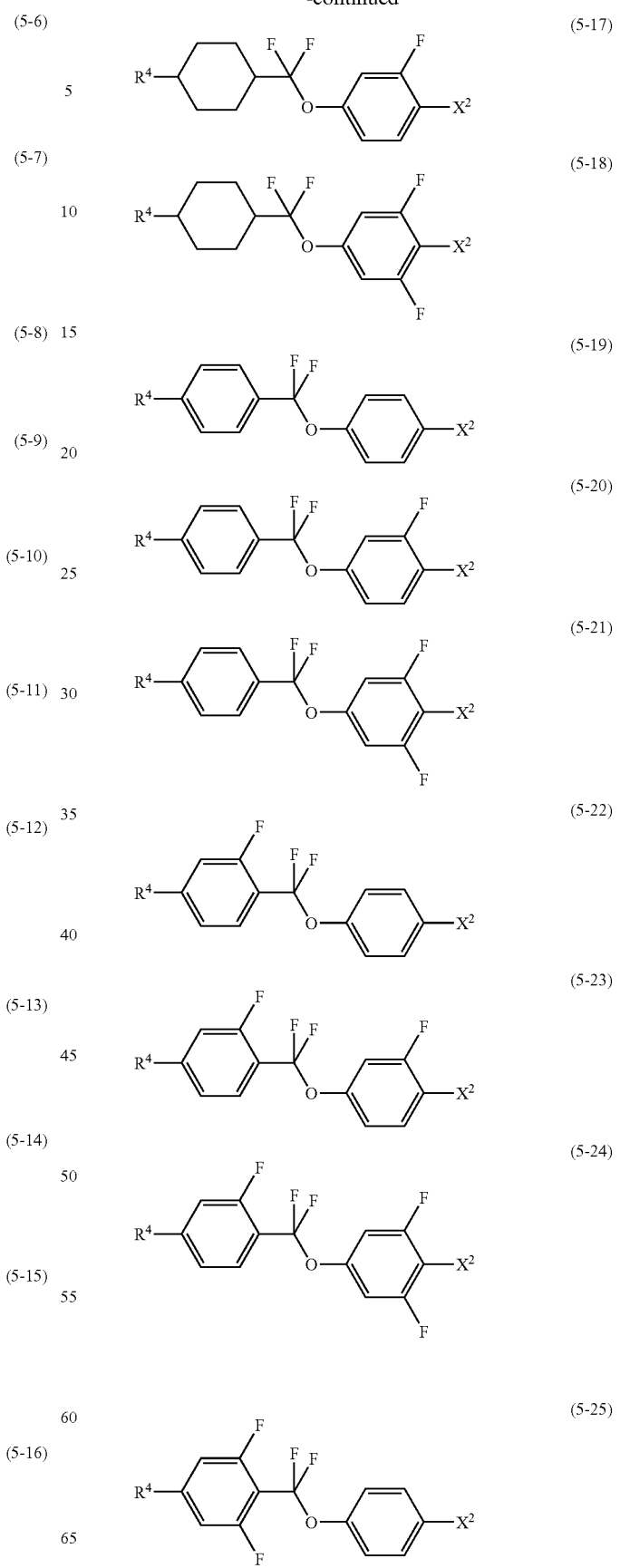

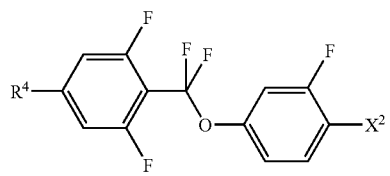
(5-26)
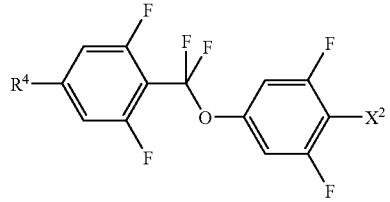
(5-27)
(5-28)
(5-29)
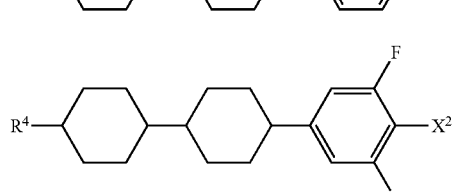
(5-30)
(5-31)
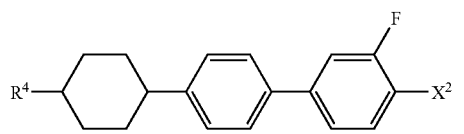
(5-32)
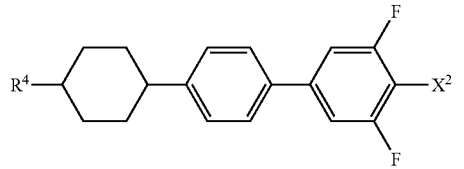
(5-33)
(5-34)
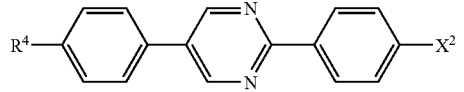
(5-35)
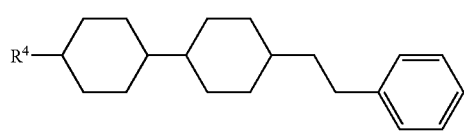
(5-36)
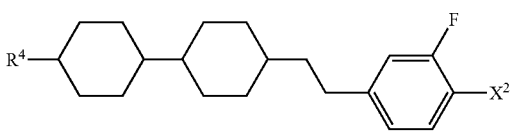
(5-37)
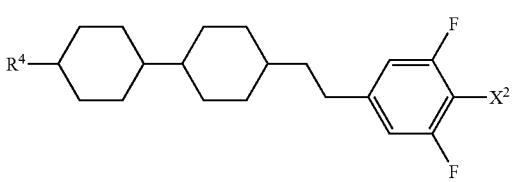
(5-38)
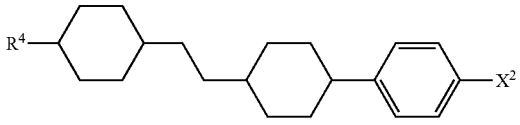
(5-39)
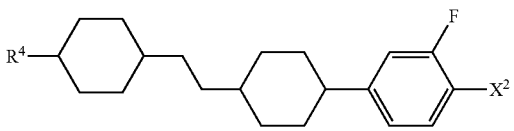
(5-40)
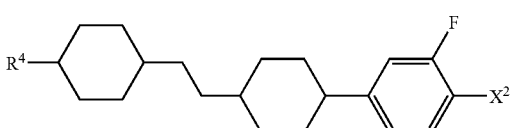
(5-41)
(5-42)
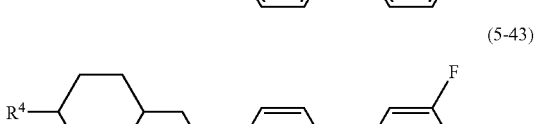
(5-43)
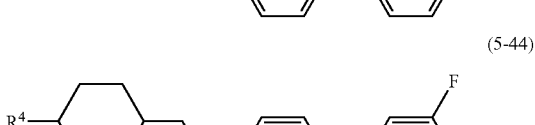
(5-44)
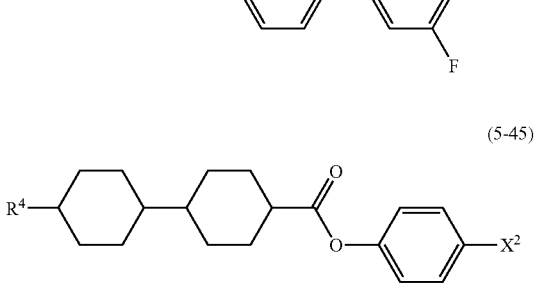
(5-45)

(5-46)
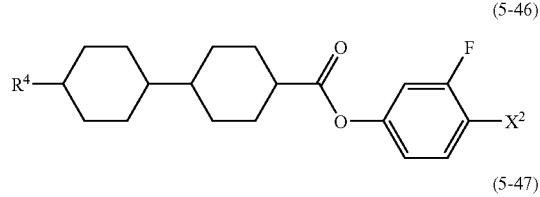
(5-47)
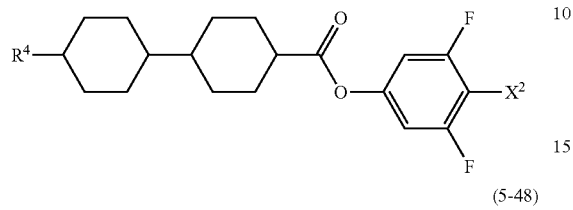
(5-48)
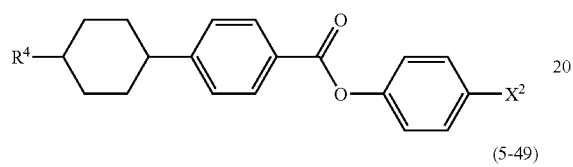
(5-49)
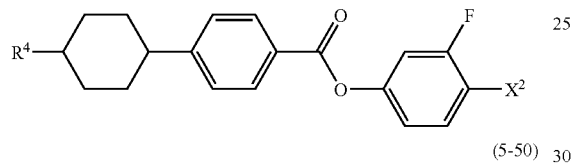
(5-50)
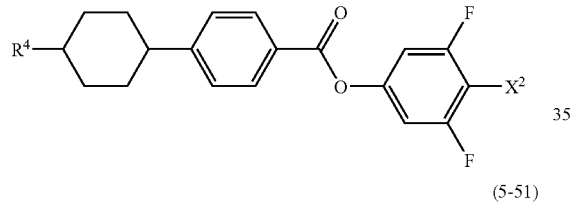
(5-51)
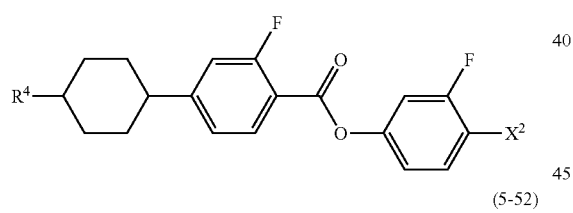
(5-52)
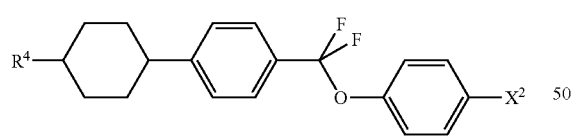
(5-53)
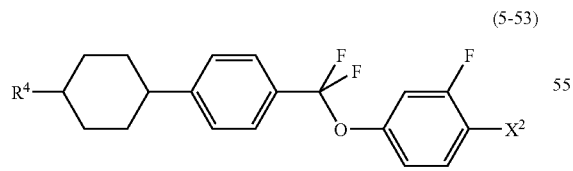
(5-54)
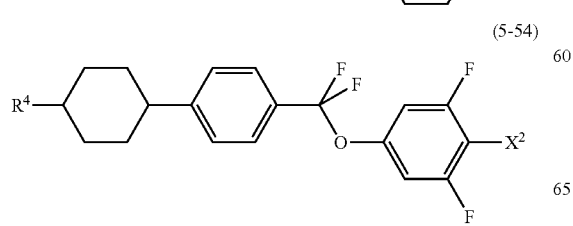
(5-55)
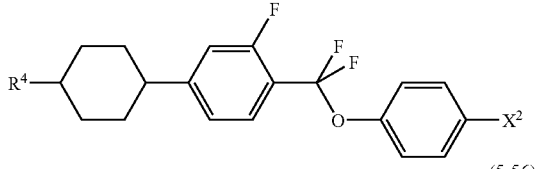
(5-56)
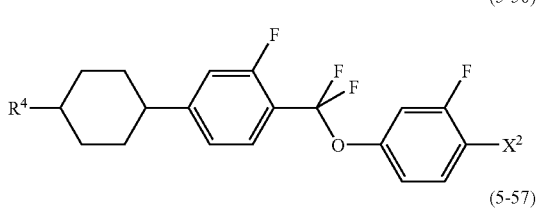
(5-57)
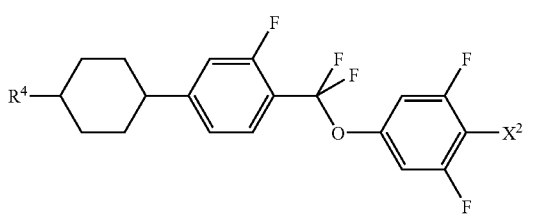
(5-58)
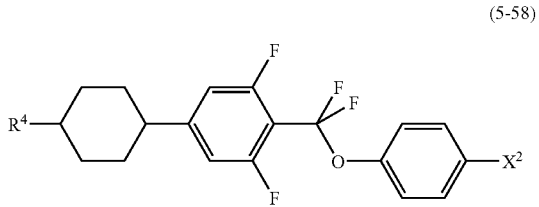
(5-59)
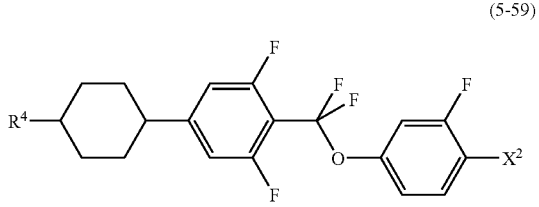
(5-60)
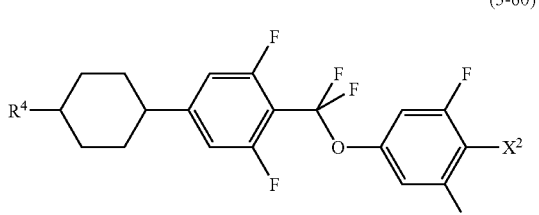
(5-61)
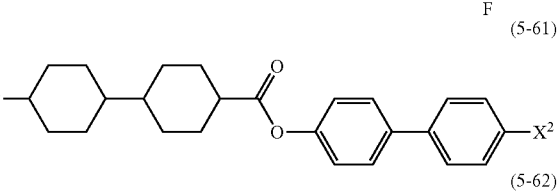
(5-62)
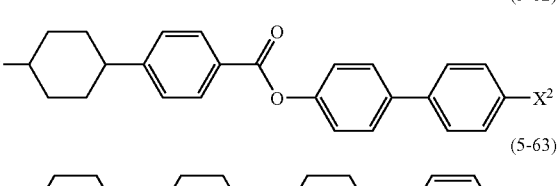
(5-63)
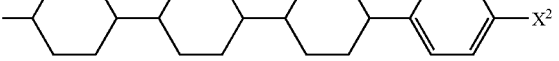

(5-64)

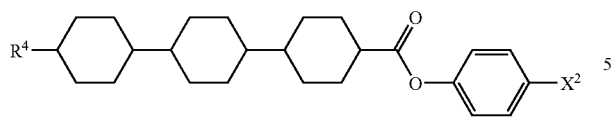

In the formulae (5-1) to (5-64), $R^4$ and $X^3$ have the same meanings as described above.

The compound represented by formula (5), i.e., the component C, has a large positive dielectric anisotropy ($\Delta\epsilon$), and thus the compound is used mainly for preparing a liquid crystal composition for an STN mode device or a TN mode device The addition of the component C decreases the threshold voltage of the composition. The addition of the component C enables control of the viscosity, control of the refractive index anisotropy ($\Delta n$) and enhancement of the temperature range of a liquid crystal phase. The component C is also used for improving steepness of the characteristics.

The content of the component C for preparing a liquid crystal composition for an STN mode device or a TN mode device is preferably approximately 0.1% to approximately 99.9% by weight, more preferably from approximately 10% to approximately 97% by weight, and further preferably from approximately 40% to approximately 95% by weight, based on the total weight of the liquid crystal composition of the invention. The threshold voltage, the temperature range of a liquid crystal phase, the refractive index anisotropy ($\Delta n$), the dielectric anisotropy ($\Delta\epsilon$), the viscosity and so forth can be controlled by adding components described later.

The component D containing at least one compound selected from the group of compounds represented by formulae (6) to (10) is preferably used for preparing the liquid crystal composition of the invention that has a negative dielectric anisotropy ($\Delta\epsilon$) for use in a vertical alignment (VA) mode.

Preferred examples of the compounds represented by formulae (6) to (10), i.e., the component D, include compounds represented by formulae (6-1) to (6-5), (7-1) to (7-11), (8-1), (9-1) to (9-3), and (10-1) to (10-11).

(6-1)

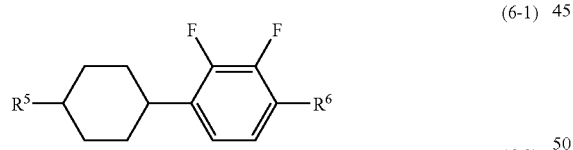

(6-2)

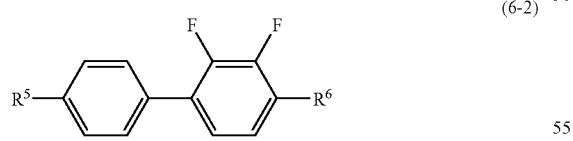

(6-3)

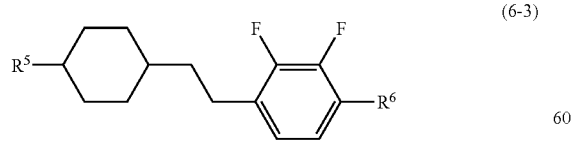

(6-4)

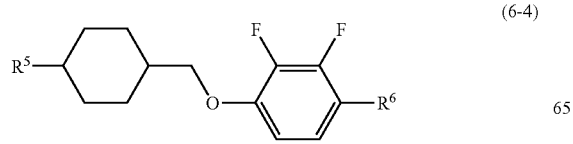

(6-5)

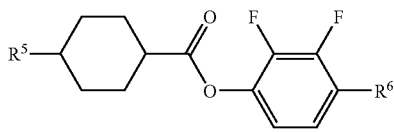

(7-1)

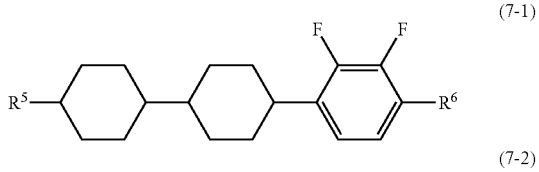

(7-2)

(7-3)

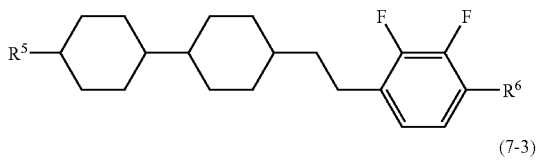

(7-4)

(7-5)

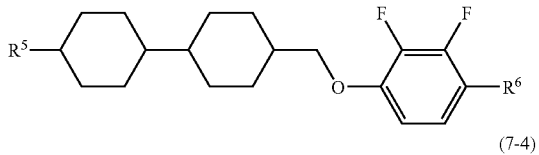

(7-6)

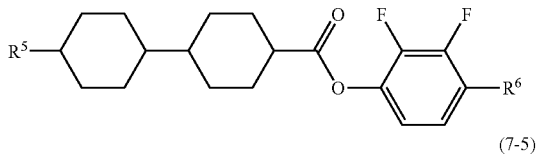

(7-7)

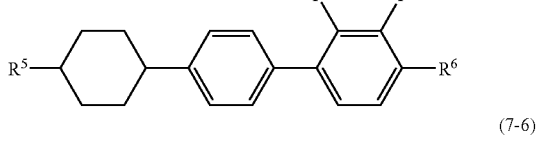

(7-8)

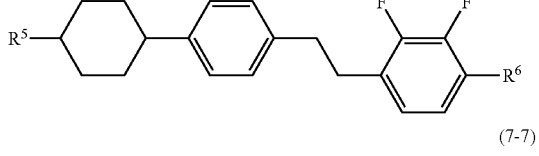

(7-9)

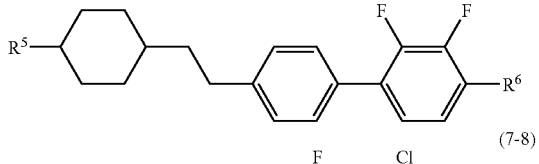

(7-10)

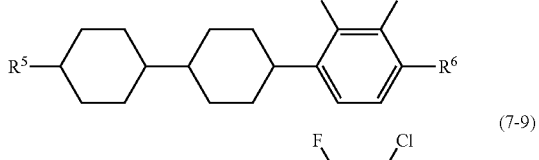

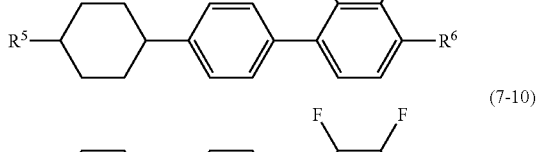

(7-11)
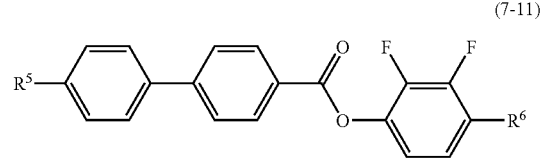

(8-1)
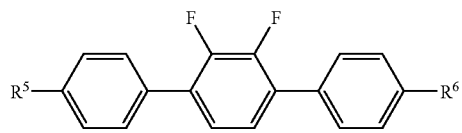

(9-1)
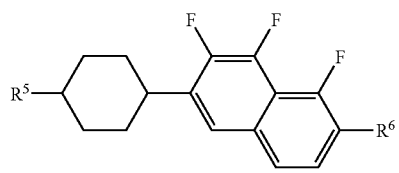

(9-2)
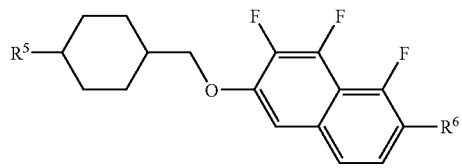

(9-3)
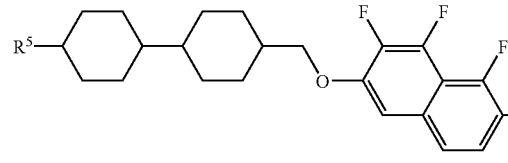

(10-1)
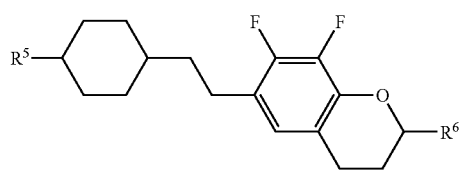

(10-2)
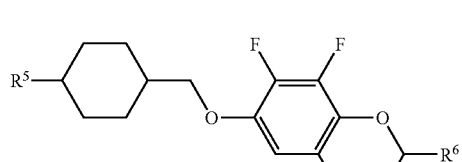

(10-3)
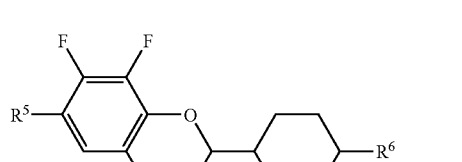

(10-4)
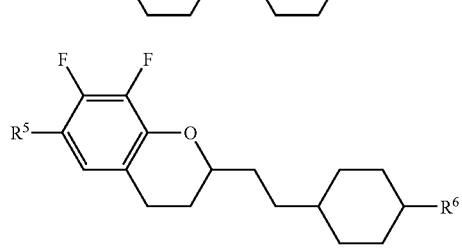

(10-5)
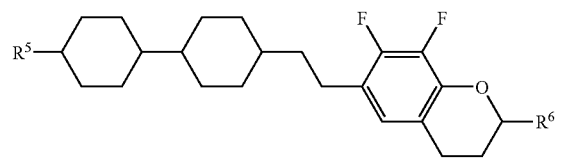

(10-6)
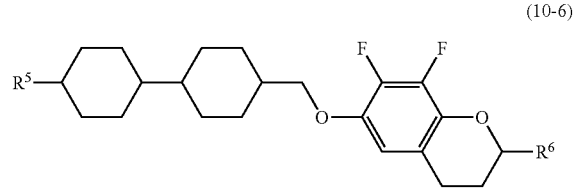

(10-7)
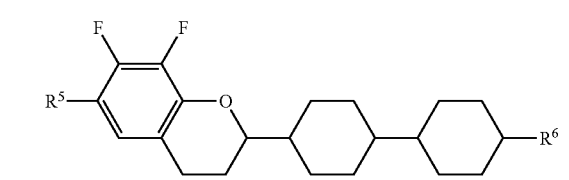

(10-8)
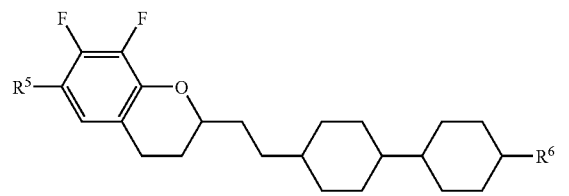

(10-9)
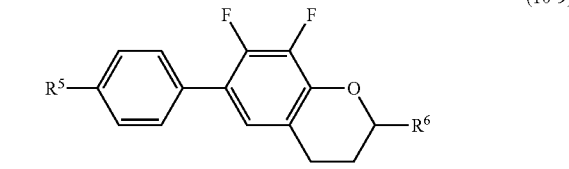

(10-10)
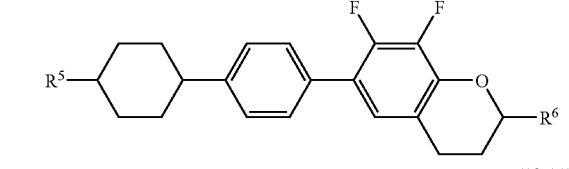

(10-11)
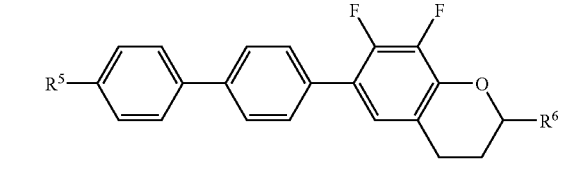

In the formulae (6-1) to (6-5), (7-1) to (7-11), (8-1), (9-1) to (9-3), and (10-1) to (10-11), $R^5$ and $R^6$ have the same meanings as described above.

The component D is used mainly in a liquid crystal composition having a negative dielectric anisotropy ($\Delta\epsilon$) for a VA mode. In the case where the content of the component D is increased, the threshold voltage of the composition is decreased, but the viscosity thereof is increased. Accordingly, the content of the component D is preferably small as far as the demanded value of the threshold value is satisfied. Since the absolute value of the dielectric anisotropy ($\Delta\epsilon$) is approximately 5, there are cases where the device cannot be driven with voltage when the content of the component is less than approximately 40% by weight.

In the component D, the compound represented by formula (6) is a bicyclic compound and thus is effective for controlling the threshold voltage, the viscosity or the refractive index anisotropy (Δn). The compound represented by formulae (7) and (8) is a tricyclic compound and thus provides effects of increasing the clear point, enhancing the temperature range of a nematic phase, decreasing the threshold voltage, increasing the refractive index anisotropy (Δn), and so forth.

The content of the component D for preparing a composition for a VA mode is preferably approximately 40% by weight or more, and more preferably from approximately 50% to approximately 95% by weight, based on the total amount of the composition. The addition of the component D enables control of the elastic constant, which relates to the stability of orientation, and control of the voltage-transmittance curve of the composition. In the case where the component D is added to the composition having a positive dielectric anisotropy (Δε), the content thereof is preferably approximately 30% by weight or less based on the total amount of the composition.

Preferred examples of the compounds represented by formulas (11), (12) and (13), i.e., the component E, include compounds represented by formulae (11-1) to (11-11), (12-1) to (12-18) and (13-1) to (13-6).

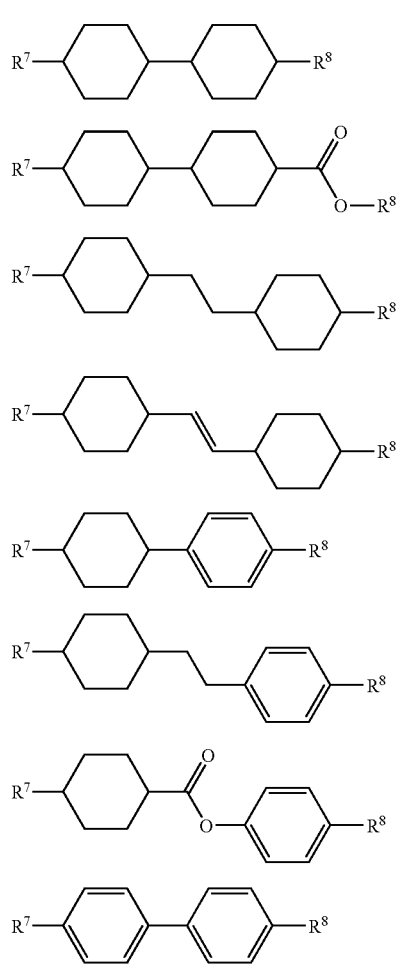

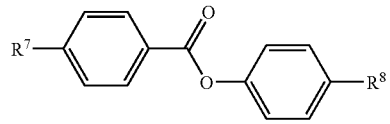

(11-9)

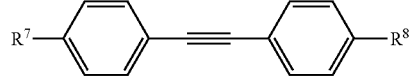

(11-10)

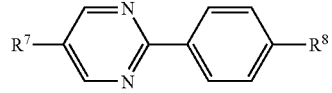

(11-11)

(12-1)

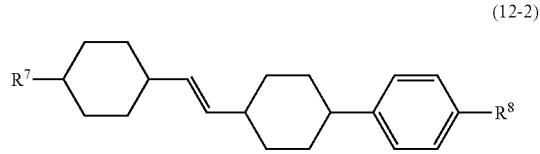

(12-2)

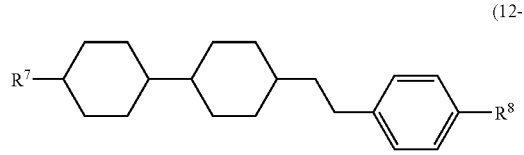

(12-3)

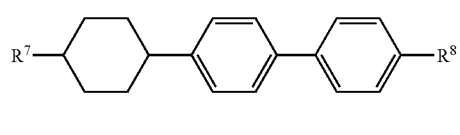

(12-4)

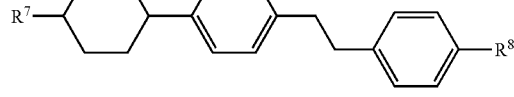

(12-5)

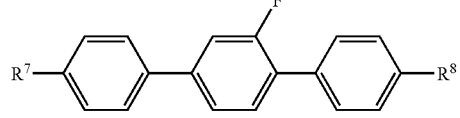

(12-6)

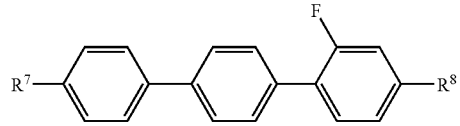

(12-7)

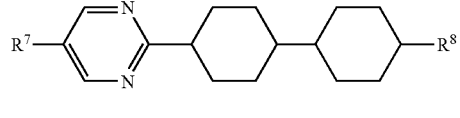

(12-8)

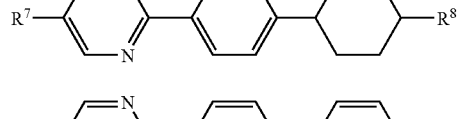

(12-9)

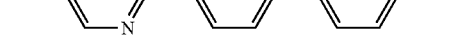

(12-10)

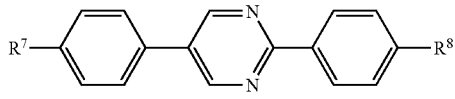
(12-11)

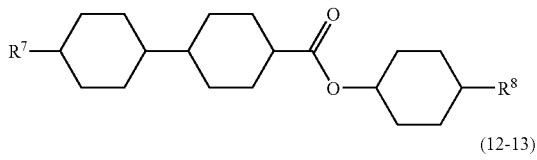
(12-12)

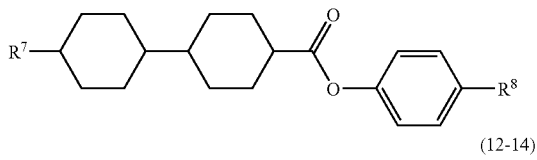
(12-13)

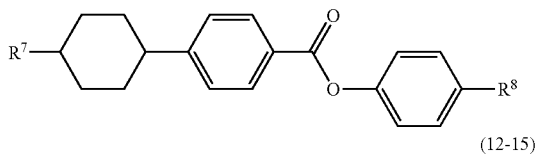
(12-14)

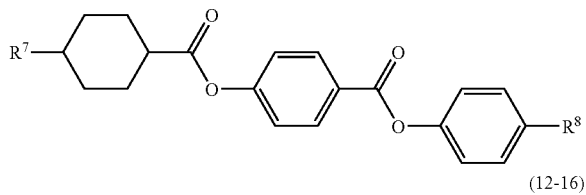
(12-15)

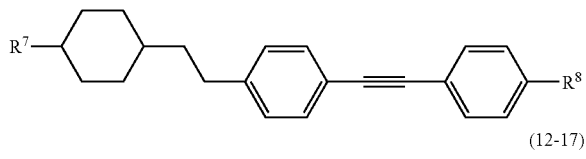
(12-16)

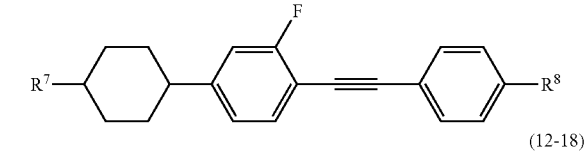
(12-17)

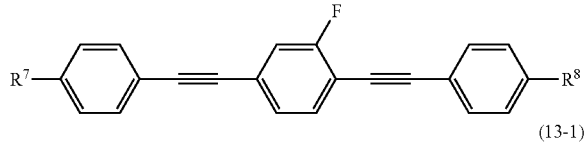
(12-18)

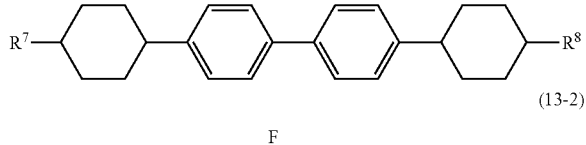
(13-1)

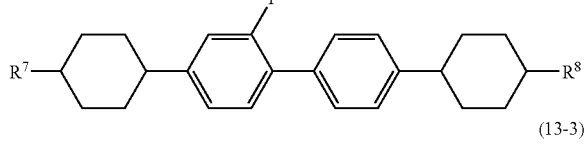
(13-2)

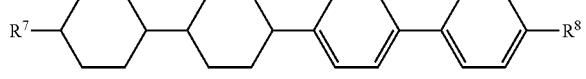
(13-3)

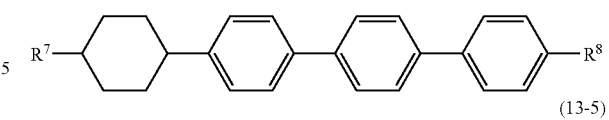
(13-4)

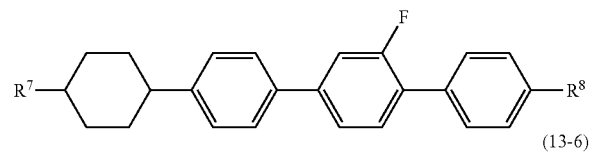
(13-5)

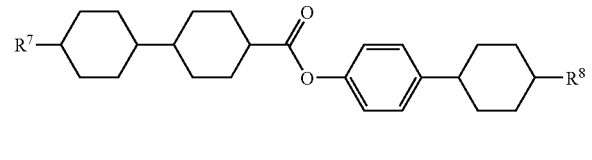
(13-6)

In the formulas (11-1) to (11-11), (12-1) to (12-18) and (13-1) to (13-6), $R^7$ and $R^8$ have the same meanings as described above.

The compound represented by formulae (11) to (13), i.e., the component E, is a compound having a small absolute value of dielectric anisotropy (Δε), i.e., a nearly neutral compound. The compound represented by formula (11) is effective mainly for controlling the viscosity and for controlling the refractive index anisotropy (Δn), and the compound represented by formulae (12) and (13) is effective mainly for enhancing the temperature range of a nematic phase, for example, increasing the clear point, and for controlling the refractive index anisotropy (Δn).

In the case where the content of the compound of the component E is increased, the liquid crystal composition is increased in threshold voltage and lowered in viscosity, and therefore the content thereof is preferably large as far as the demanded value of the threshold voltage of the liquid crystal composition is satisfied. In the case where a liquid crystal composition for a TFT mode device is prepared, the content of the component E is preferably approximately 60% by weight or less, and more preferably approximately 40% by weight or less, based on the total amount of the composition. In the case where a liquid crystal composition for an STN mode device or a TN mode device is prepared, the content of the component E is preferably approximately 70% by weight or less, and more preferably approximately 60% by weight or less, based on the total amount of the composition.

The liquid crystal composition of the invention preferably contains at least one kind of the compound represented by formula (1-1) or (1-2) of the invention in a ratio of from approximately 0.1% to approximately 99% by weight for exhibiting the excellent characteristics.

The liquid crystal composition of the invention can be generally prepared by a known method, for example, by dissolving the necessary components at an increased temperature. An additive having been known in the art may be added to the composition depending on purposes, whereby a liquid crystal composition (f) of the invention containing an optically active compound and a liquid crystal composition for a GH mode containing a dichroic dye can be prepared. The additive has been well known by a skilled person in the art and is disclosed in literatures in detail. A polymerizable compound, a polymerization initiator and so forth may be added for using in a PSA mode device.

The liquid crystal composition (f) of the invention contains at least one kind of an optically active compound.

A known chiral dopant maybe added as the optically active compound. The chiral dopant has such a function that a helical structure of the liquid crystal is induced, whereby the necessary helical angle is controlled to prevent reverse twisting. Examples of the chiral dopant include the following optically active compounds.

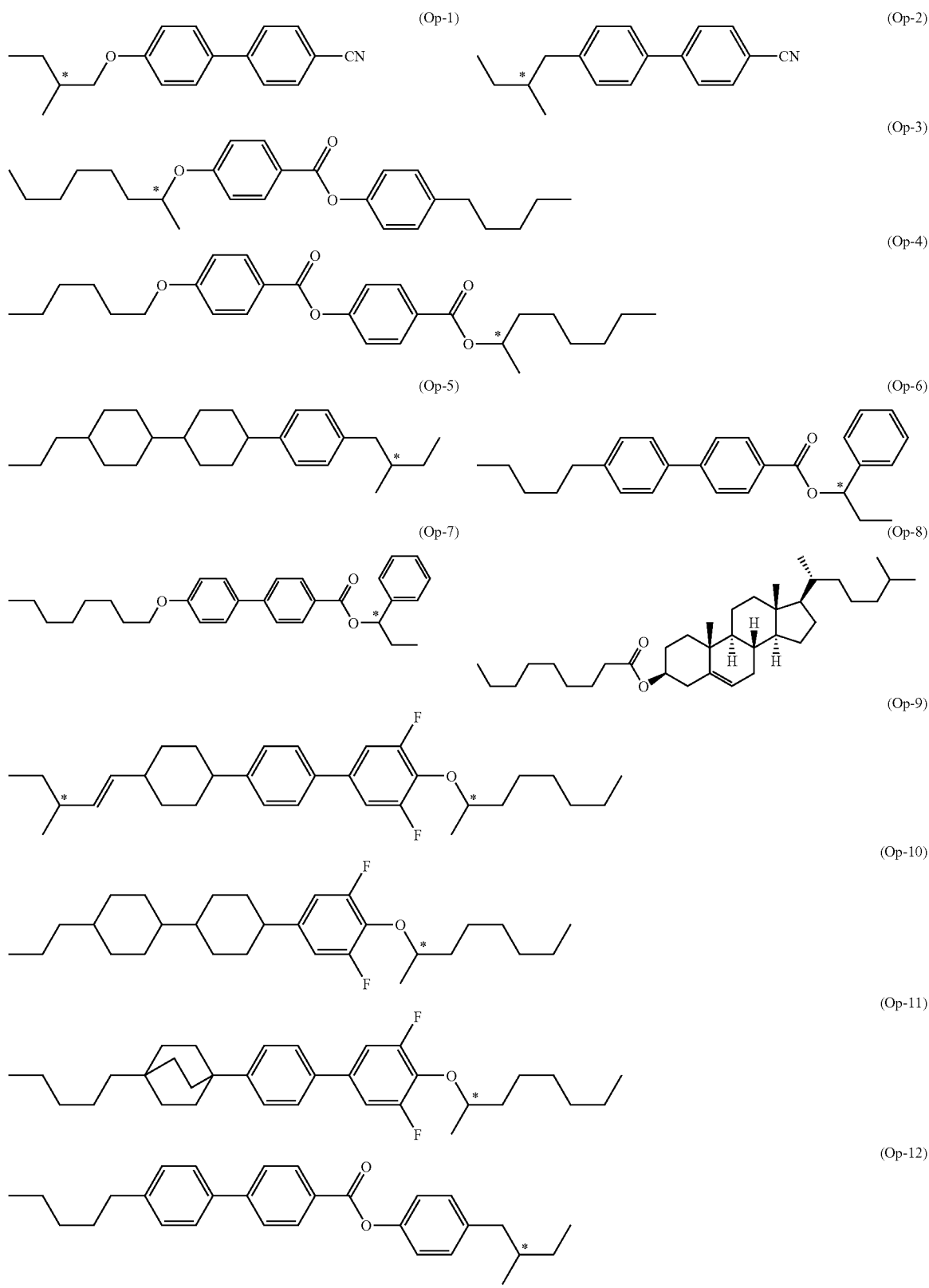

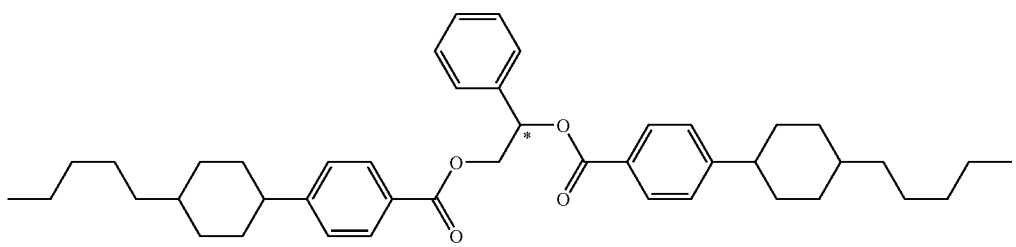
(Op-13)

The liquid crystal composition (f) of the invention is controlled in helical pitch generally by adding the optically active compound. The helical pitch is preferably controlled to a range of from approximately 40 µm to approximately 200 µm for a liquid crystal composition for a TFT mode device or a TN mode device, is preferably controlled to a range of from approximately 6 µm to approximately 20 µm for a liquid crystal composition for an STN mode device, and is preferably controlled to a range of from approximately 1.5 µm to approximately 4 µm for a liquid crystal composition for a bistable TN mode device. Two or more kinds of optically active compounds may be added for the purpose of controlling the temperature dependency of the pitch.

The liquid crystal composition of the invention can be used as a liquid crystal composition for a GH mode device by adding a dichroic dye, such as a merocyanine series, a styryl series, an azo series, an azomethine series, an azoxy series, a quinophthalone series, an anthraquinone series and a tetrazine series.

The liquid crystal composition of the invention can be applied to such purposes as a nematic curvilinear aligned phase (NCAP) device prepared by microcapsulating a nematic liquid crystal composition, a polymer-dispersed liquid crystal display device. (PDLCD) produced by forming a three-dimensional network polymer in a liquid crystal, a polymer network liquid crystal display device (PNLCD), an electrically controlled birefringence (ECB) mode liquid crystal display device and a dynamic scattering (DS) mode liquid crystal display device.

A polymerizable compound is mixed with the composition for applying the composition to a device having a PSA (polymer sustained alignment) mode. Preferred examples of the polymerizable compound include compounds having a polymerizable group, such as acrylate, methacrylate, vinyl, vinyloxy, propenyl ether, epoxy and so forth. Particularly preferred examples thereof include derivatives of acrylate or methacrylate. A desirable ratio of the polymerizable group is from approximately 0.05% by weigh or more for obtaining the advantages thereof, and is approximately 10% by weight or less for preventing display failure from occurring. A more desirable ratio is from approximately 0.1% to approximately 2% by weight. The polymerizable compound is polymerized preferably in the presence of a suitable initiator, such as a photopolymerization initiator and so forth, under radiation of ultraviolet light. Suitable conditions for polymerization and a suitable type and a suitable amount of the initiator have been known by a skilled person in the art and are disclosed in literatures. Examples of the photopolymerization initiator suitable for radical polymerization include Irgacure 651 (trade name), Irgacure 184 (trade name) and Darocure 1173 (trade name), all produced by Ciba Japan Co., Ltd. The polymerizable compound preferably contains a photopolymerization initiator in an amount of from approximately 0.1% to approximately 5% by weight, and particularly preferably contains a photopolymerization initiator in an amount of from approximately 1% to approximately 3% by weight.

EXAMPLES

The invention will be described in more detail with reference to examples below, but the invention is not construed as being limited to the examples. All occurrences of "%" are by weight unless otherwise indicated.

The resulting compounds were identified by magnetic nuclear resonance spectra obtained by $^1$H-NMR analysis, gas chromatograms obtained by gas chromatography (GC) analysis, and so forth. Accordingly, the analysis methods will be described below.

$^1$H-NMR Analysis

DRX-500 (produced by Bruker Biospin Co., Ltd.) was used for measurement. A sample produced in the examples and so forth was dissolved in a deuterated solvent capable of dissolving the sample, such as $CDCl_3$, and the measurement was carried out at room temperature and 500 MHz with an accumulated number of 24. In the description of the resulting nuclear resonance spectra, s means a singlet, d means a doublet, t means a triplet, q means a quartet, and m means a multiplet. Tetramethylsilane (TMS) was used as a standard substance indicating zero point of chemical shift δ.

GC Analysis

Gas Chromatograph Model GC-14B made by Shimadzu was used for measurement. Capillary column CBP1-M25-025 (length: 25 m, bore: 0.22 mm, film thickness: 0.25 µm, dimethylpolysiloxane as stationary phase, no polarity) produced by Shimadzu Corp. was used as a column. Helium was used as a carrier gas and adjusted to a flow rate of 1 mL/min. The temperature of a sample vaporizing chamber was 280° C., and the temperature of the detector (FID) was 300° C.

The sample was dissolved in toluene to prepare a 1% by weight solution, and 1 µL of the resulting solution was injected into the sample vaporizing chamber.

Chromatopac Model C-R6A, produced by Shimadzu Corp., or an equivalent thereof was used as a recorder. The gas chromatogram obtained showed a retention time of a peak and a peak area corresponding to the component compound.

Solvents for diluting the sample may also be chloroform, hexane, and so forth. The following capillary columns may also be used: a capillary column DB-1, produced by Agilent Technologies Inc. (length: 30 m, bore: 0.32 mm, film thickness: 0.25 µm), a capillary column HP-1, produced by Agilent Technologies Inc. (length: 30 m, bore: 0.32 mm, film thickness: 0.25 µm), a capillary column Rtx-1, produced by Restek Corporation (length: 30 m, bore: 0.32 mm, film thickness: 0.25 µm), and a capillary column BP-1, produced by SGE International Pty. Ltd. (length: 30 m, bore: 0.32 mm, film thickness: 0.25 µm).

An area ratio of each peak in the gas chromatogram corresponds to a ratio of the component compound. In general, the percentages by weight of the component compounds of the analyzed sample are not completely identical to the percentages by area of the peaks of the analyzed sample. According to the invention, however, the percentages by weight of the component compounds of the analyzed sample substantially correspond to the percentages by area of the peaks of the analyzed sample because the correction coefficient is substantially 1 when the aforementioned columns are used in the invention.

Sample of Liquid Crystal Compound for Measuring Characteristics

A sample of the liquid crystal compound for measuring characteristics includes two cases, i.e., the case where the compound itself is used as a sample, and the case where the compound is mixed with mother liquid crystals to prepare a sample.

In the later case where a sample is prepared by mixing the compound with mother liquid crystals, the measurement is carried out in the following manner. A sample was produced by mixing 15% by weight of the compound and 85% by weight of mother liquid crystals. A value of characteristics of the compound was calculated by extrapolating from a value obtained by measurement.

Extrapolated Value=(100×(measured value of sample)−(percentage by weight of mother liquid crystals)×(value measured for mother liquid crystals))/(percentage by weight of liquid crystal compound)

In the case where a smectic phase was exhibited at 25° C. or crystals were deposited at 25° C. at this ratio of the liquid crystal compound and the mother liquid crystals, the ratio of the compound and the mother liquid crystals was changed step by step in the order of (10% by weight/90% by weight), (5% by weight/95% by weight), (1% by weight/99% by weight), respectively. The value of characteristics of the sample was measured at a ratio where a smectic phase or crystals were not deposited at 25° C., and an extrapolated value was obtained by the aforementioned equation, which was designated as a value of characteristics of the liquid crystal compound.

While there are various kinds of mother liquid crystals for the aforementioned measurement, the composition of the mother liquid crystals A was as follows, for example.

Mother Liquid Crystals A

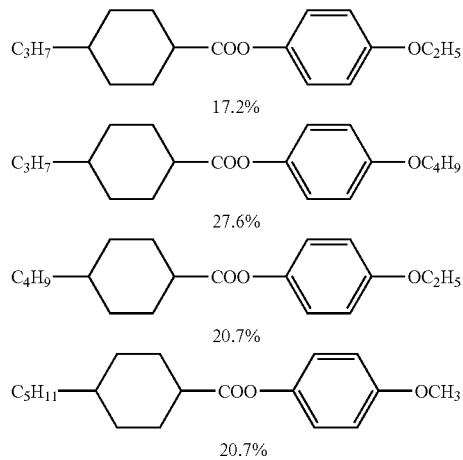

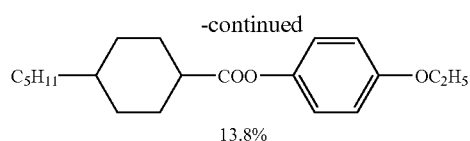

As a sample for measuring characteristics of a liquid crystal composition, the liquid crystal composition itself was used.

Measurement Method of Characteristics of Liquid Crystal Compound

Measurement of the characteristics was carried out according to the following methods. Most methods are described in the Standard of Electric Industries Association of Japan EIAJ ED-2521A or those with some modifications. A TFT was not attached to a TN device or a VA device used for measurement.

Among the measured values, the values obtained with the liquid crystal compound itself as a sample and the values obtained with the liquid crystal composition itself as a sample were described as experimental data. In the case where the values were obtained with the mixture of the compound with the mother liquid crystals, the extrapolated values were described as experimental data.

Phase Structure and Phase Transition Temperature (° C.)

The measurement was carried out in the methods (1) and (2) below.

(1) A compound was placed on a hot plate (Hot Stage Model FP-52., produced by Mettler Co., Ltd.) in a melting point apparatus equipped with a polarizing microscope, and while heating at the rate of 3° C. per minute, the state of the phase and the changes thereof were observed with the polarizing microscope to determine the kind of the phase.

(2) A sample was heated and cooled at a rate of 3° C. per minute by using a scanning calorimeter, DSC-7 System or Diamond DSC System, produced by Perkin-Elmer, Inc., whereby a starting point of an endothermic peak or an exothermic peak associated with phase change of the sample was obtained by extrapolation (on set) to determine phase transition temperature.

In the following description, a crystal is denoted by "C". In the case where a crystal is distinguished into two crystals, they are denoted by "$C_1$" and "$C_2$", respectively. A smectic phase is denoted by "S", and a nematic phase is denoted by "N." A liquid (isotropic phase) is denoted by "Iso". In the case where a smectic phase is distinguished into a smectic B phase and a smectic A phase, they are denoted by "$S_B$" and "$S_A$", respectively. The expression of the phase transition temperature, "C 50.0 N 100.0 Iso", for example, means that the transition temperature of from a crystal to a nematic phase (CN) is 50.0° C., and the transition temperature of from a nematic phase to a liquid (NI) is 100.0° C. The other expressions are applied with the same rule.

Maximum Temperature of Nematic Phase ($T_{NI}$; ° C.)

A sample (a liquid crystal composition or a mixture of a liquid crystal compound and the mother liquid crystals) was placed on a hot plate (Hot Stage Model FP-52, produced by Mettler Co., Ltd.) in a melting point apparatus equipped with a polarizing microscope, and while heating at the rate of 1° C. per minute, was observed with the polarizing microscope. A temperature where a part of the sample was changed from a nematic phase to an isotropic liquid was designated as a maximum temperature of a nematic phase. The maximum temperature of a nematic phase may be abbreviated to "a maximum temperature" in some cases.

Low Temperature Compatibility

Samples were prepared by mixing the mother liquid crystals and a liquid crystal compound to make a ratio of the liquid crystal compound of 20% by weight, 15% by weight, 10% by weight, 5% by weight, 3% by weight and 1% by weight, respectively, and then placed in glass bottles. The glass bottles were stored in a freezer at −10° C. or −20° C. for a prescribed period of time, and then were observed as to whether or not a crystal or a smectic phase was deposited. Viscosity (η; measured at 20° C.; mPa·s)

There is a general tendency that the response time is decreased when the viscosity is small.

The viscosity was measured by means of an E-type viscometer.

Rotation Viscosity (γ1; measured at 25° C.; mPa·s)

There is a general tendency that the response time is decreased when the rotation viscosity is small.

The rotation viscosity was measured according to the method disclosed in M. Imai, et al., Molecular Crystals and Liquid Crystals, vol. 259, p. 37 (1995). A sample (a liquid crystal composition or a mixture of a liquid crystal compound and the mother liquid crystals) was placed in a VA device having a cell gap between two glass plates of 20 μm. The VA device was impressed with a voltage in a range of from 30 V to 50 V stepwise by 1 V. After a period of 0.2 second with no impress of voltage, voltage impress was repeated with only one rectangular wave (rectangular pulse of 0.2 second) and application of no voltage (2 seconds). A peak current and a peak time of a transient current generated by the voltage impress were measured. The rotation viscosity was obtained from the measured values and the calculating equation (8) in the literature by M. Imai, et al., p. 40. As the dielectric anisotropy (Δε) necessary for the calculation, the value measured by the measuring method of dielectric anisotropy (Δε) described below was used.

Refractive Index Anisotropy (Δn; measured at 25° C.)

Measurement was carried out with an Abbe refractometer mounting a polarizing plate on an ocular using light having a wavelength of 589 nm at a temperature of 25° C. The surface of a main prism was rubbed in one direction, and then a sample (a liquid crystal composition or a mixture of a liquid crystal compound and the mother liquid crystals) was dropped on the main prism. A refractive index (n∥) was measured when the direction of polarized light was parallel to that of the rubbing A refractive index (n⊥) was measured when the direction of polarized light was perpendicular to that of the rubbing. A value of refractive index anisotropy (Δn) was calculated from the equation: Δn=n∥−n⊥.

Dielectric Anisotropy (Δε; measured at 25° C.)

A solution of octadecyltriethoxysilane (0.16 mL) and ethanol (20 mL) was coated on a glass substrate having been well cleaned. The glass substrate was spun with a spinner and then heated to 150° C. for 1 hour. A VA device having a distance (cell gap) of 20 μm was fabricated with two sheets of the glass substrates.

A polyimide oriented film was prepared on a glass substrate in the similar manner. The oriented film of the glass substrate was rubbed, and a TN device having a distance between two glass substrates of 9 μm and a twist angle of 80° was fabricated.

A sample (a liquid crystal composition or a mixture of a liquid crystal compound and the mother liquid crystals) was put in the VA device, which was then impressed with a voltage of 0.5 V (1 kHz, sine wave) to measure a dielectric constant (ε∥) in the major axis direction of the liquid crystal molecule. A sample (a liquid crystal composition or a mixture of a liquid crystal compound and the mother liquid crystals) was put in the TN device, which was then impressed with a voltage of 0.5 V (1 kHz, sine wave) to measure a dielectric constant (ε⊥) in the minor axis direction of the liquid crystal molecule.

The dielectric anisotropy (Δε) was calculated from the equation; (Δε)=(ε∥)−(ε⊥).

SYNTHESIS EXAMPLE OF LIQUID CRYSTAL COMPOUND

Example 1

Synthesis of 5-[4-(ethoxy-2,3-difluorophenoxy)cyclohexyl]-2-vinyltetrahydropyran (Compound No. 7)

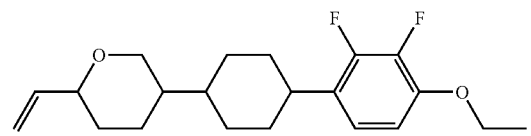 [SMILES: C=CC1CCC(C2CCC(c3ccc(OCC)c(F)c3F)CC2)CO1]

First Step

In a reactor under nitrogen atmosphere, 25 mL of THF was added to 7.7 g of methoxymethyltriphenylphosphonium chloride, and the mixture was cooled to −20° C., to which 2.5 g of t-BuOK was added, followed by stirring for 1 hour A solution containing 5.0 g of 4-(4-ethoxy-2,3-difluorophenyl) cyclohexane-carboaldehyde dissolved in 50 mL of THF was added dropwise thereto, followed by stirring for 1 hour. The temperature of the reaction mixture was increased to room temperature, and 100 mL of water was added to the reaction mixture, followed by extracting three times with 100 mL of toluene. The resulting organic layer was washed with water, dried over anhydrous magnesium sulfate, and the solvent was concentrated to about 100 mL under reduced pressure, and the concentrated solution was placed in 500 mL of toluene, followed by removing deposited solid matters. The solvent was distilled off from the resulting solution under reduced pressure, and the residue was purified by silica gel column chromatography to provide 4.9 g of 1-ethoxy-2,3-difluoro-4-[4-(2-methoxyvinyl)-cyclohexyl]benzene.

Second Step 4.9 g of 1-ethoxy-2,3-difluoro-4-[4-(2-methoxyvinyl)-cyclohexyl]benzene obtained in the first step was dissolved in 100 mL of acetone, to which 8 mL of hydrochloric acid (4M) was added, followed by stirring at room temperature for 1 hour. 100 mL of water was added to the reaction mixture, which was extracted three times with 50 mL of toluene. The mixture including the organic layer was washed with water and dried over anhydrous magnesium sulfate, and the solvent was distilled off under reduced pressure to provide 4.6 g of [4-(4-ethoxy-2,3-difluorophenyl)cyclohexyl]acetaldehyde.

Third Step 4.6 g of [4-(4-ethoxy-2,3-difluorophenyl)cyclohexyl]-acetaldehyde obtained in the second step was dissolved in 100 mL of THF, to which 1.2 g of pyrrolidine was added under cooling with ice. 2.0 g of potassium carbonate was added to the reaction solution, which was stirred at room temperature for 5 hours and then filtered, and the solvent was distilled off from the solution under reduced pressure to provide 5.5 g of 1-{2-[4-(4-ethoxy-2,3-difluorophenyl)-cyclohexyl] vinyl}pyrrolidine.

Fourth Step

In a reactor under nitrogen atmosphere, 5.5 g of 1-{2-[4-(4-ethoxy-2,3-difluorophenyl)cyclohexyl]vinyl}-pyrrolidine obtained in the third step was dissolved in 20 mL of toluene, to which 5.7 g of ethyl acrylate and 0.3 g of hydroquinone were added. The reaction solution was stirred at 80° C. for 5 hours and then cooled to room temperature, to which 50 mL of a saturated oxalic acid aqueous solution was added. The mixture was extracted three times with 30 mL of diethyl ether, and the mixture including the organic layer was washed with water and dried over anhydrous magnesium sulfate, followed by distilling off the solvent under reduced pressure. The residue was purified by silica gel column chromatography to provide 5.7 g of ethyl 4-[4-(4-ethoxy-2,3-difluorophenyl)-cyclohexyl]-5-oxopentanoate.

Fifth Step

In a reactor under nitrogen atmosphere, 20 mL of ethanol and 0.4 g of sodium cyanoborohydride were added to 5.7 g of ethyl 4-[4-(4-ethoxy-2,3-difluorophenyl)cyclohexyl]-5-oxopentanoate obtained in the fourth step, and pH of the mixture was adjusted to about 3 with hydrochloric acid (2M), followed by stirring at room temperature for 15 hours. 30 mL of water was added to the reaction solution, which was extracted three times with 20 mL of toluene. The mixture including the organic layer was washed with water and dried over anhydrous magnesium sulfate, and the solvent was distilled off under reduced pressure. The residue was placed in a flask equipped with a Dean-Stark apparatus, to which 100 mL of toluene and 0.1 g of p-toluenesulfonic acid monohydrate were added, and the mixture was refluxed for 1 hour while the solvent was distilled off with the Dean-Stark apparatus. The solution was cooled to room temperature, washed with water, and dried over anhydrous magnesium sulfate, and the solvent was distilled off under reduced pressure. The residue was purified by silica gel column chromatography to provide 4.2 g of 5-[4-(4-ethoxy-2,3-difluorophenyl)cyclohexyl]tetrahydropyran-2-one.

Sixth Step

In a reactor under nitrogen atmosphere, 20 mL of THF was added to 1.3 g of trimethylsylylacetylene, and the mixture was cooled to −70° C., to which 8.5 mL (about 1.6 mmol) of n-butyllithium was added dropwise, followed by stirring at −70° C. for 1 hour. A solution containing 4.2 g of 5-[4-(4-ethoxy-2,3-difluorophenyl)cyclohexyl]tetrahydropyran-2-one obtained in the fifth step dissolved in 50 mL of THF was added dropwise thereto at −70° C., followed by stirring for 1 hour. The temperature of the reaction mixture was increased to room temperature, to which 50 mL of a saturated ammonium chloride aqueous solution was added, and the mixture was separated. The aqueous layer was extracted three times with 30 mL of diethyl ether. The mixture including the organic layer was washed with water and dried over anhydrous magnesium sulfate, and the solvent was distilled off under reduced pressure. The residue was purified by silica gel column chromatography to provide 4.8 g of 5-[4-(4-ethoxy-2,3-difluoro-phenyl)cyclohexyl]-2-trimethylsilanylethylnyltetrahydro-pyran-2-ol.

Seventh Step

In a reactor under nitrogen atmosphere, 100 mL of dichloromethane and 20 mL of acetonitrile were added to 4.8 g of 5-[4-(4-ethoxy-2,3-difluorophenyl)cyclohexyl]-2-trimethylsilanylethylnyltetrahydro-pyran-2-ol obtained in the sixth step, and the mixture was cooled to −20° C., to which 3.5 mL of triethylsilane was added dropwise, and subsequently 18 mL of boron trifluoride diethyl ether complex was added dropwise. The temperature of the reaction solution was increased to 0° C., to which 50 mL of iced water was added, followed by extracting three times with 30 mL of diethyl ether. The mixture including the organic layer was washed with water and dried over anhydrous magnesium sulfate, and the solvent was distilled off under reduced pressure. The residue was purified by silica gel column chromatography to provide 3.7 g of (5-[4-(4-ethoxy-2,3-difluorophenyl)-cyclohexyl]tetrahydropyran-2-ylethynyl)trimethylsilane.

Eighth Step 40 mL of methanol and 30 mL of dichloromethane were added to 3.7 g of (5-[4-(4-ethoxy-2,3-difluorophenyl)cyclohexyl]-tetrahydropyran-2-ylethynyl) trimethylsilane obtained in the seventh step, and the mixture was cooled to 0° C., to which 5 mL of a sodium hydroxide aqueous solution (1M) was added. The temperature of the reaction solution was increased to room temperature, and the reaction solution was stirred for 2 hours, neutralized with hydrochloric acid, and the solvent was concentrated to about 30 mL under reduced pressure. The residue was extracted three times with 20 mL of diethyl ether, and the mixture including the organic layer was washed with water and dried over anhydrous magnesium sulfate, followed by distilling off the solvent. The residue was purified by silica gel column chromatography to provide 2.6 g of 5-[4-(4-ethoxy-2,3-difluorophenyl)cyclohexyl]-2-ethynyltetrahydropyran.

Ninth Step 100 mL of n-heptane, 100 mL of toluene, 0.5 mL of quinoline and 0.05 g of a Lindlar catalyst were added to 2.6 g of 5-[4-(4-ethoxy-2,3-difluorophenyl)cyclohexyl]-2-ethynyltetrahydropyran obtained in the eighth step. After depressurizing the reactor with a vacuum pump, hydrogen was introduced thereto under ordinary pressure, followed by stirring at ordinary temperature for 90 minutes. The catalyst was removed from the reaction solution by filtration, and the filtrate was concentrated under reduced pressure. The residue was purified by silica gel column chromatography and recrystallization to provide 1.9 g of 5-[4-ethoxy-2,3-difluorophenoxy)cyclohexyl]-2-vinyltetrahydropyran. The yield based on 4-(4-ethoxy-2,3-difluorophenyl)cyclohexane-carboaldehyde used in the first step was 29%.

The chemical shifts δ (ppm) in ¹H-NMR analysis were as follows, and thus the resulting compound was identified as 5-[4-ethoxy-2,3-difluorophenoxy)cyclohexyl]-2-vinyltetrahydropyran. The solvent for measurement was CDCl₃. Chemical shift δ (ppm): 6.82 (m, 1H), 6.65 (m, 1H), 5.86 (m, 1H), 5.24 (d, 1H), 5.10 (d, 1H), 4.09 (m, 3H), 3.73 (m, 1H), 3.24 (t, 1H), 2.72 (m, 1H), 2.0-1.7 (m, 6H), 1.5-1.1 (m, 11H)

The resulting compound No.7 had transition temperatures (° C.) of C 103.0 N 156.0 Iso.

Example 2

The following compounds Nos. 1 to 334 can be produced according to the similar methods as in Example 1.

| No. |
| --- |
| 1 |

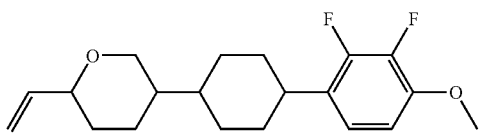 [SMILES: C=CC1CCC(C2CCC(c3ccc(OC)c(F)c3F)CC2)CO1]

-continued
| No. | |
|---|---|
| 2 | 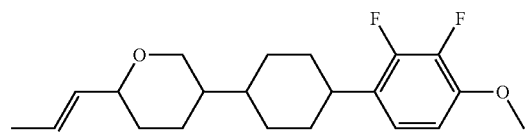 |
| 3 | 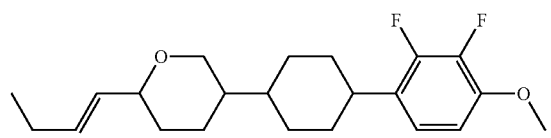 |
| 4 | 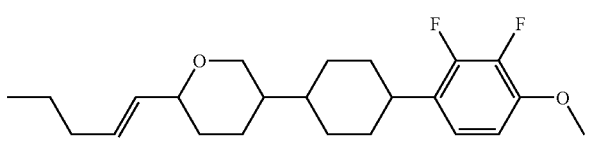 |
| 5 | 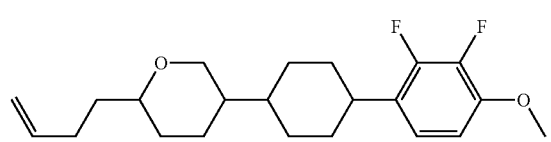 [SMILES: C=CCCC1CCC(C2CCC(c3ccc(OC)c(F)c3F)CC2)CO1] |
| 6 | 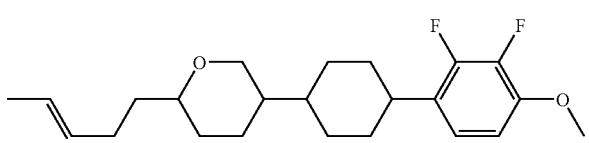 [SMILES: C/C=C/CCC1CCC(C2CCC(c3ccc(OC)c(F)c3F)CC2)CO1] |
| 7 | 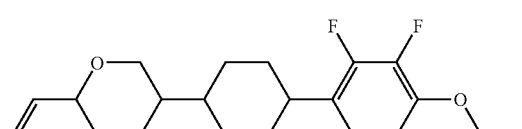 |
| 8 | 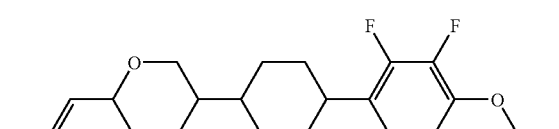 |
| 9 | 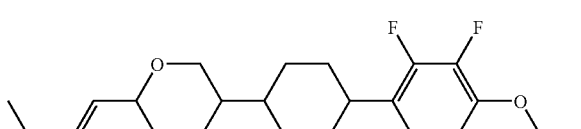 |
| 10 | 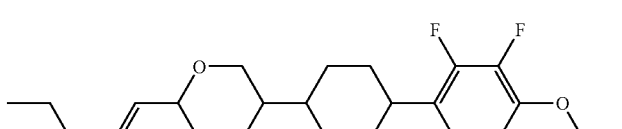 |
| 11 | 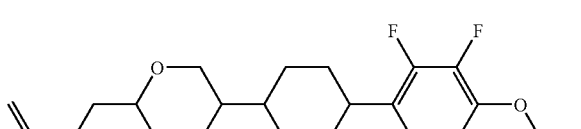 |
| 12 | 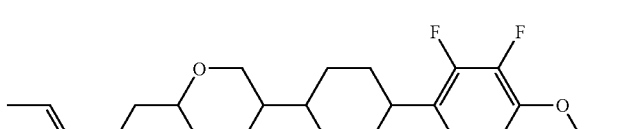 |

| No. | |
|---|---|
| 13 | 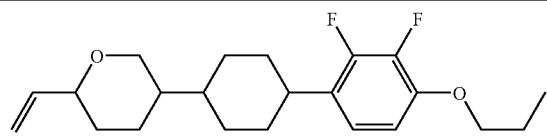 |
| 14 | 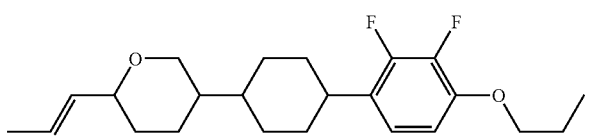 |
| 15 | 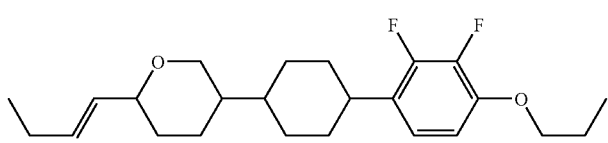 [SMILES: CC/C=C/C1CCC(C2CCC(c3ccc(OCCC)c(F)c3F)CC2)CO1] |
| 16 | 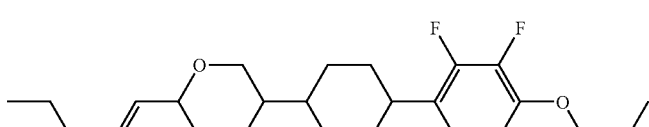 |
| 17 | 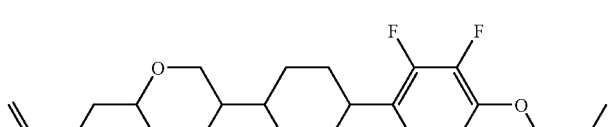 |
| 18 | 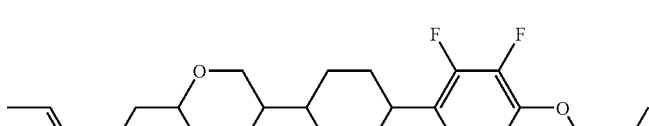 |
| 19 | 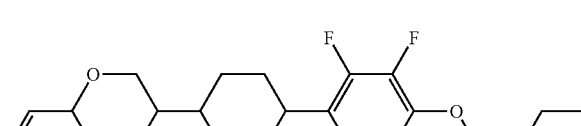 |
| 20 | 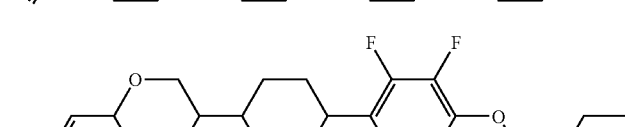 |
| 21 | 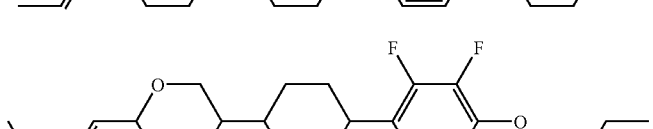 |
| 22 | 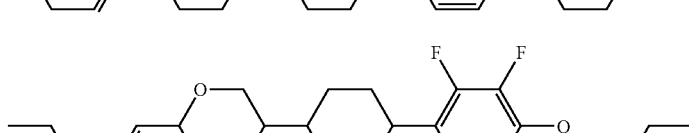 |
| 23 | 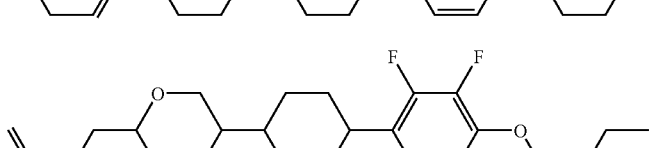 |

| No. |  |
|---|---|
| 24 | 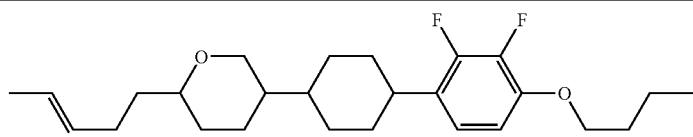 |
| 25 | 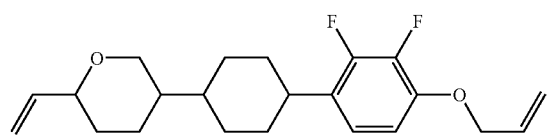 [SMILES: C=CCOc1ccc(C2CCC(C3CCC(C=C)OC3)CC2)c(F)c1F] |
| 26 | 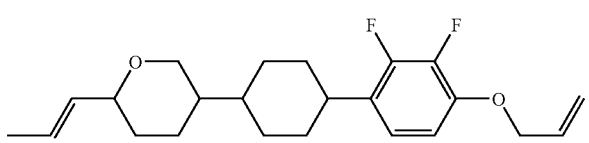 [SMILES: C=CCOc1ccc(C2CCC(C3CCC(/C=C/C)OC3)CC2)c(F)c1F] |
| 27 | 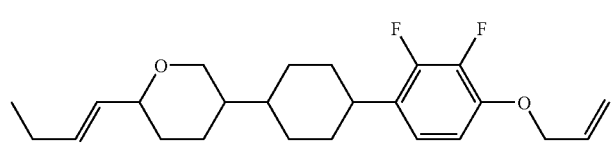 |
| 28 | 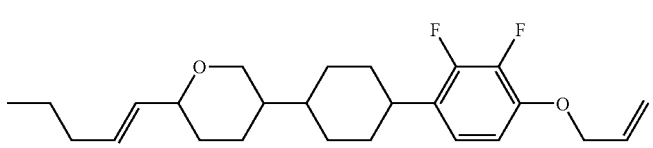 |
| 29 | 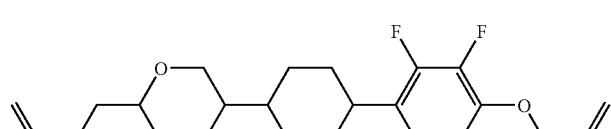 |
| 30 | 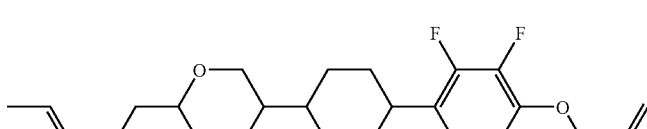 |
| 31 | 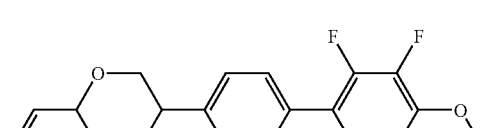 |
| 32 | 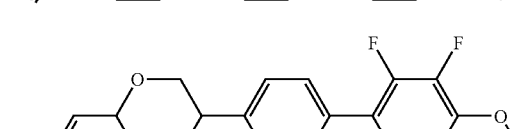 |
| 33 | 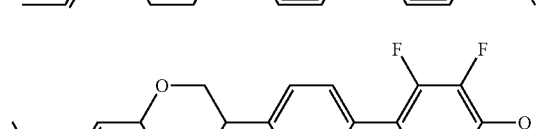 |
| 34 | 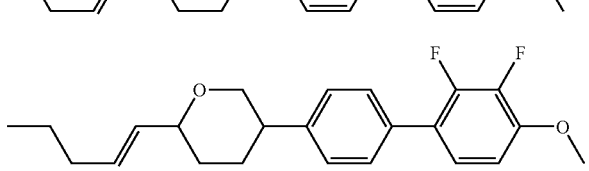 |

| No. | |
|---|---|
| 35 | 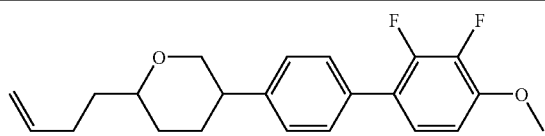 |
| 36 | 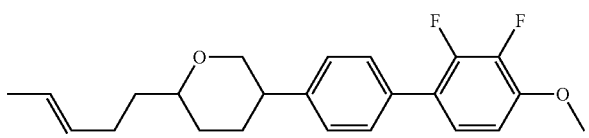 [SMILES: C/C=C/CCC1CCC(c2ccc(-c3ccc(OC)c(F)c3F)cc2)CO1] |
| 37 | 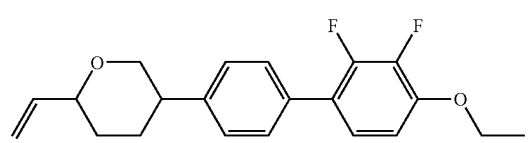 |
| 38 | 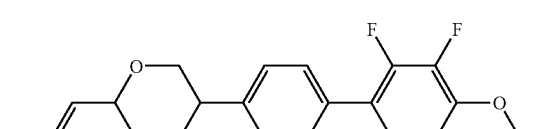 |
| 39 | 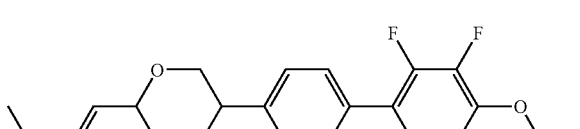 |
| 40 | 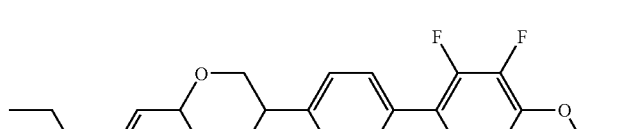 |
| 41 | 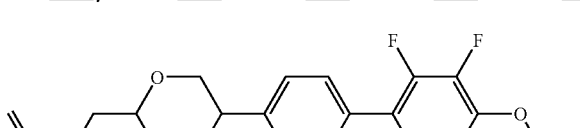 |
| 42 | 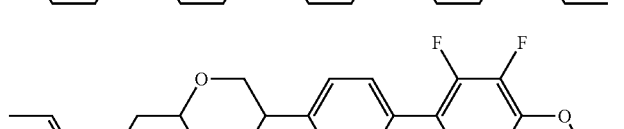 |
| 43 | 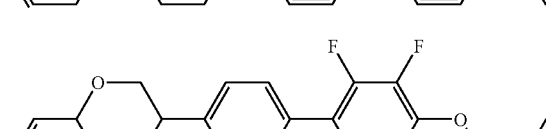 |
| 44 | 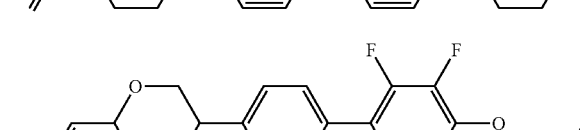 |
| 45 | 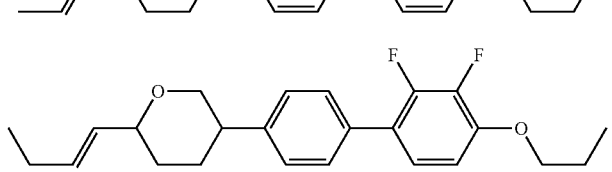 |

| No. | |
|---|---|
| 46 | 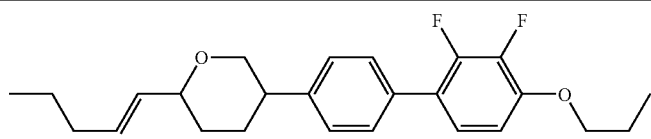 |
| 47 | 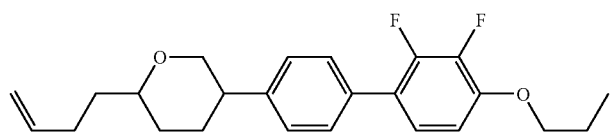 |
| 48 | 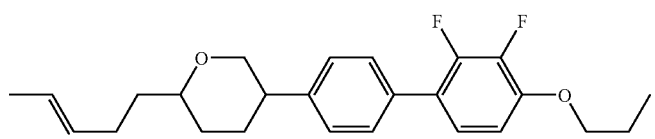 |
| 49 | 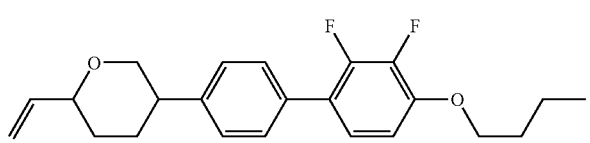 |
| 50 | 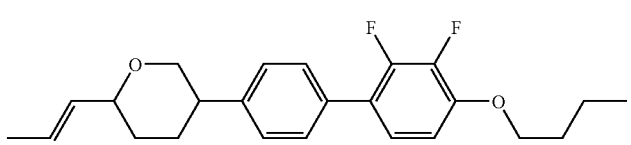 [SMILES: C/C=C/C1CCC(c2ccc(-c3ccc(OCCCC)c(F)c3F)cc2)CO1] |
| 51 | 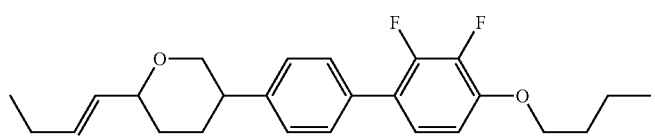 |
| 52 | 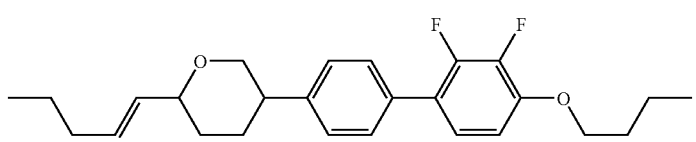 [SMILES: CCC/C=C/C1CCC(c2ccc(-c3ccc(OCCCC)c(F)c3F)cc2)CO1] |
| 53 | 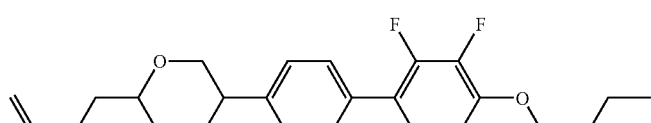 |
| 54 | 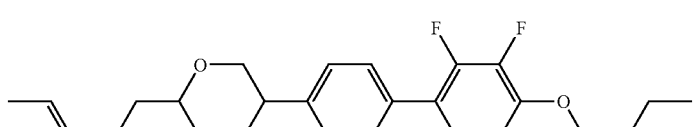 |
| 55 | 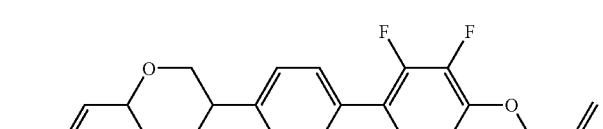 |
| 56 | 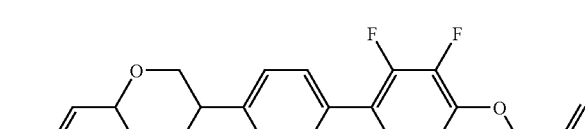 |

| No. | |
|---|---|
| 57 | 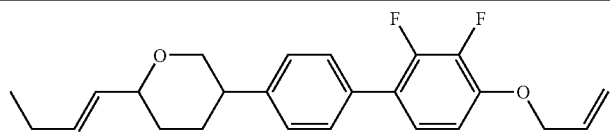 |
| 58 | 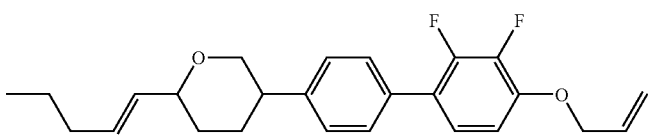 [SMILES: C=CCOc1ccc(-c2ccc(C3CCC(/C=C/CCC)OC3)cc2)c(F)c1F] |
| 59 | 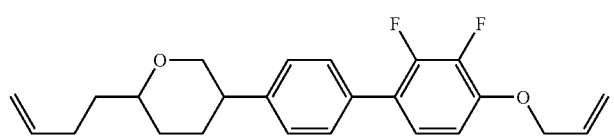 |
| 60 | 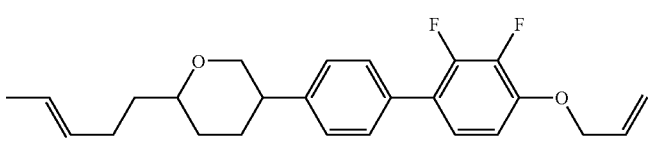 [SMILES: C=CCOc1ccc(-c2ccc(C3CCC(CC/C=C/C)OC3)cc2)c(F)c1F] |
| 61 | 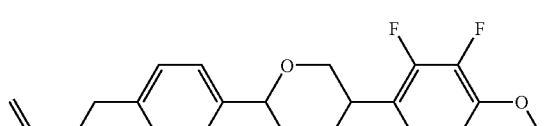 |
| 62 | 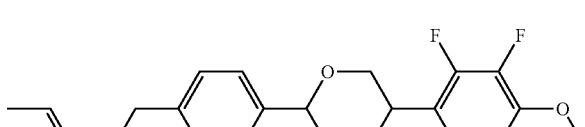 |
| 63 | 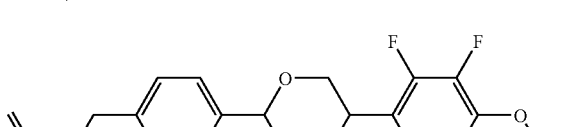 |
| 64 | 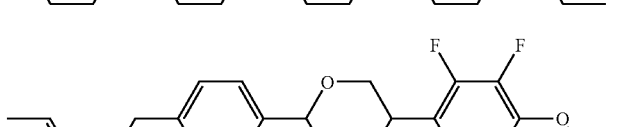 |
| 65 | 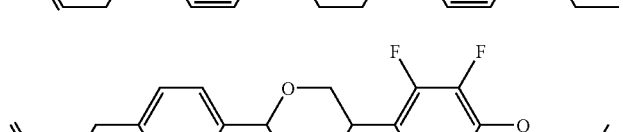 |
| 66 | 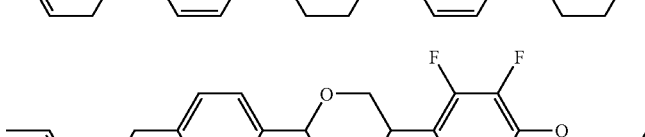 |
| 67 | 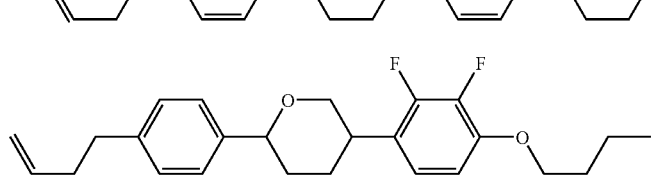 |

-continued
| No. | |
|---|---|
| 68 | 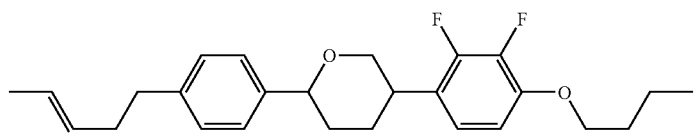 [SMILES: C/C=C/CCc1ccc(C2CCC(c3ccc(OCCCC)c(F)c3F)CO2)cc1] |
| 69 | 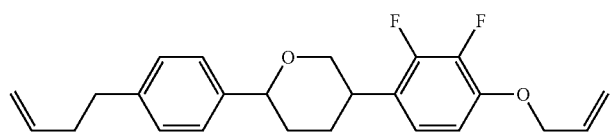 |
| 70 | 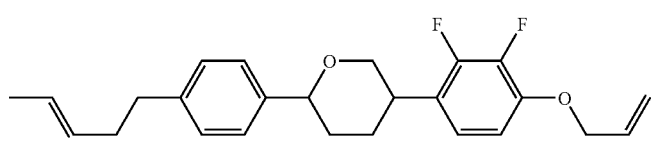 [SMILES: C=CCOc1ccc(C2CCC(c3ccc(CC/C=C/C)cc3)OC2)c(F)c1F] |
| 71 | 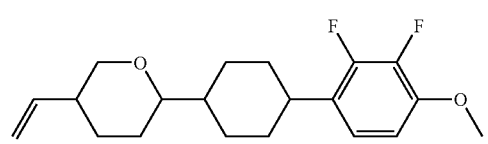 |
| 72 | 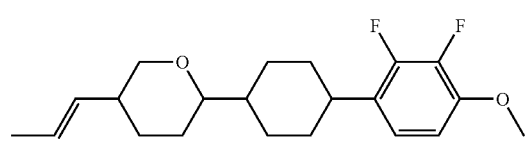 [SMILES: C/C=C/C1CCC(C2CCC(c3ccc(OC)c(F)c3F)CC2)OC1] |
| 73 | 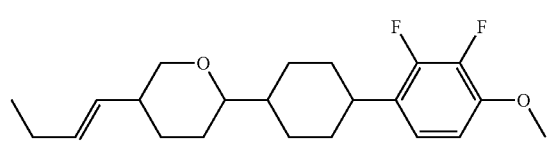 |
| 74 | 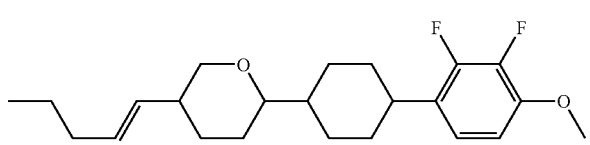 [SMILES: CCC/C=C/C1CCC(C2CCC(c3ccc(OC)c(F)c3F)CC2)OC1] |
| 75 | 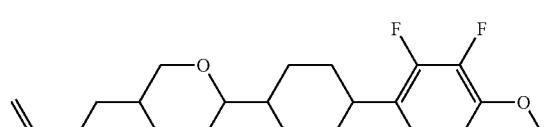 |
| 76 | 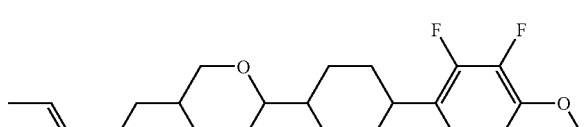 |
| 77 | 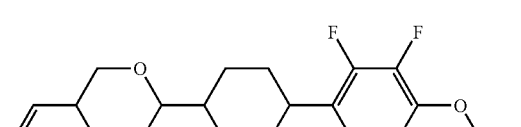 |
| 78 | 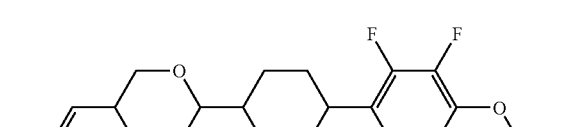 |

-continued
| No. | |
|---|---|
| 79 | 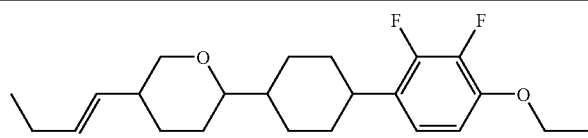 |
| 80 | 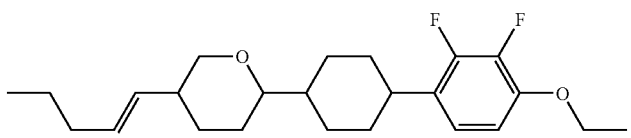 [SMILES: CCC/C=C/C1CCC(C2CCC(c3ccc(OCC)c(F)c3F)CC2)OC1] |
| 81 | 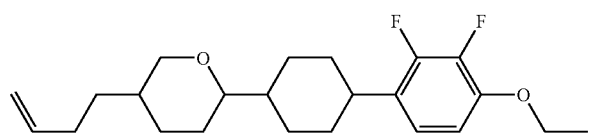 |
| 82 | 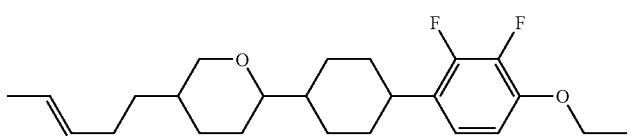 [SMILES: C/C=C/CCC1CCC(C2CCC(c3ccc(OCC)c(F)c3F)CC2)OC1] |
| 83 | 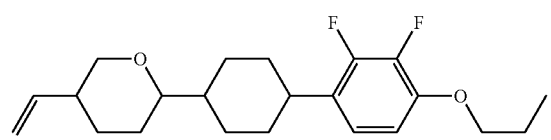 |
| 84 | 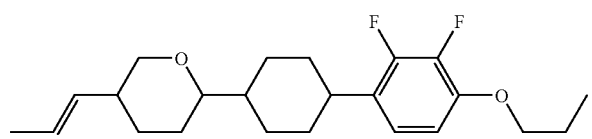 [SMILES: C/C=C/C1CCC(C2CCC(c3ccc(OCCC)c(F)c3F)CC2)OC1] |
| 85 | 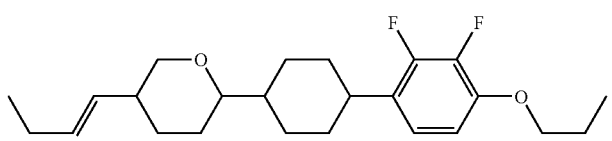 |
| 86 | 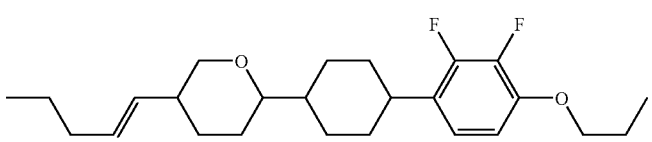 [SMILES: CCC/C=C/C1CCC(C2CCC(c3ccc(OCCC)c(F)c3F)CC2)OC1] |
| 87 | 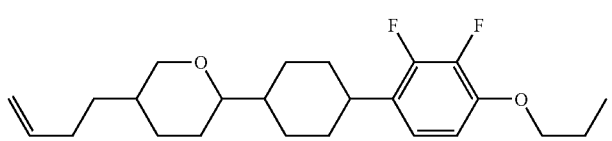 |
| 88 | 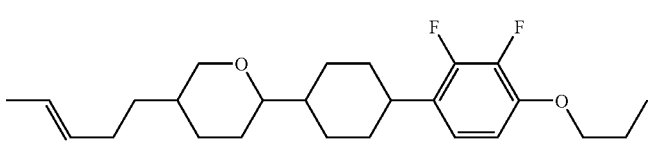 [SMILES: C/C=C/CCC1CCC(C2CCC(c3ccc(OCCC)c(F)c3F)CC2)OC1] |
| 89 | 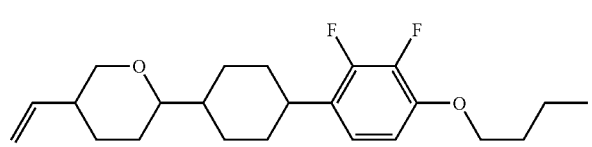 |

| No. | |
|---|---|
| 90 | 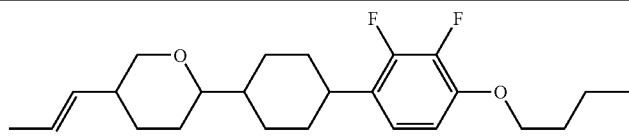 |
| 91 | 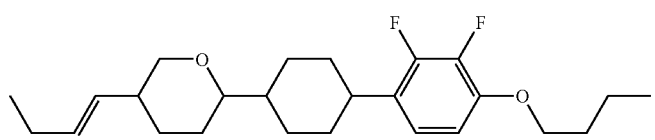 [SMILES: CC/C=C/C1CCC(C2CCC(c3ccc(OCCCC)c(F)c3F)CC2)OC1] |
| 92 | 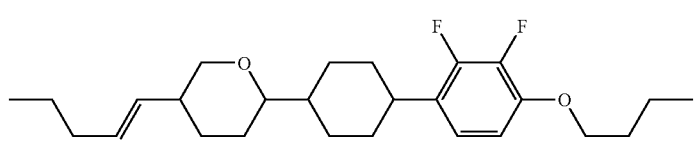 |
| 93 | 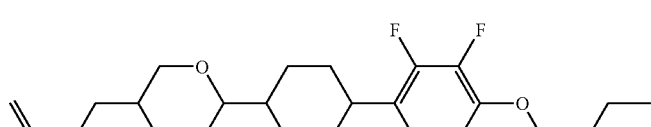 |
| 94 | 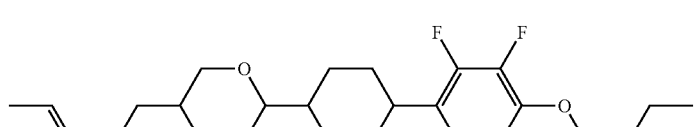 |
| 95 | 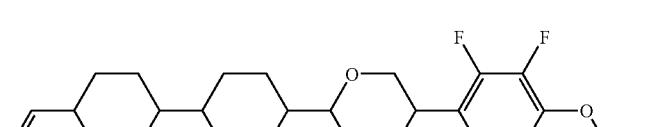 |
| 96 | 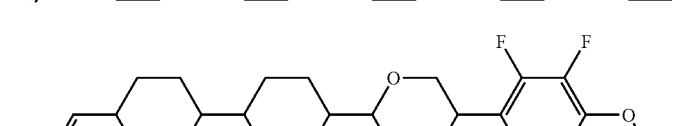 |
| 97 | 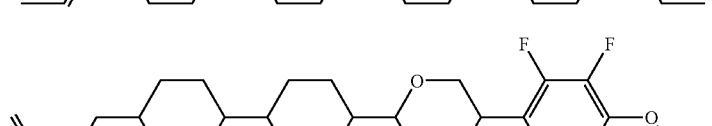 |
| 98 |  |
| 99 | 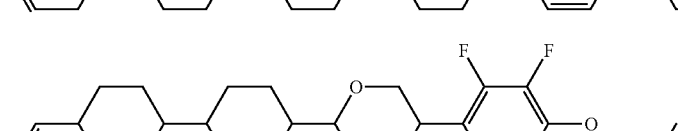 |
| 100 | 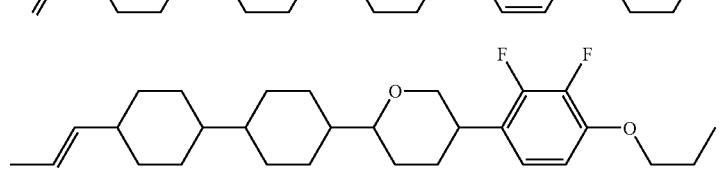 |

-continued
| No. | |
|---|---|
| 101 | 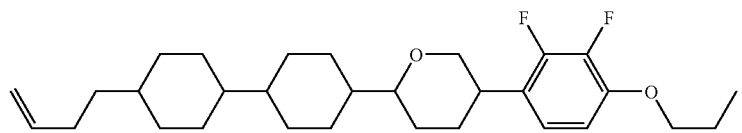 |
| 102 | 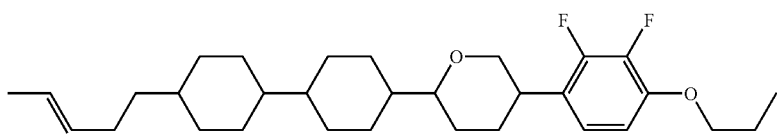 |
| 103 | 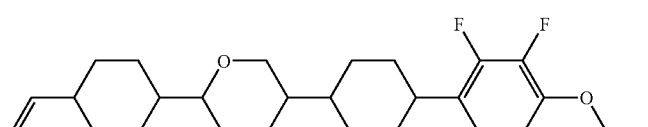 |
| 104 | 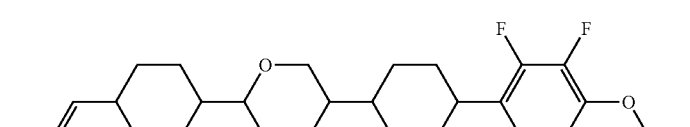 |
| 105 | 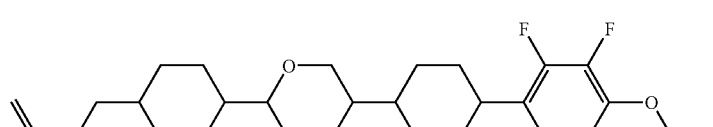 |
| 106 | 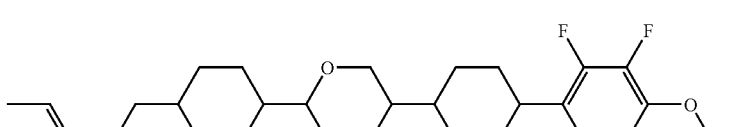 |
| 107 | 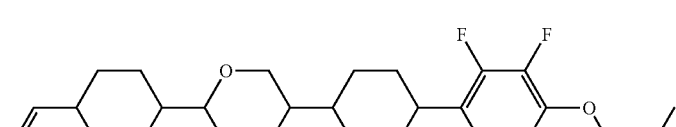 |
| 108 | 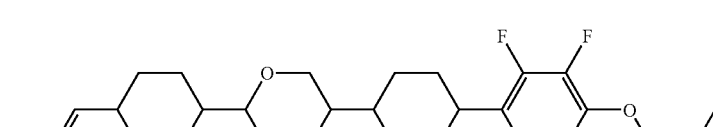 |
| 109 | 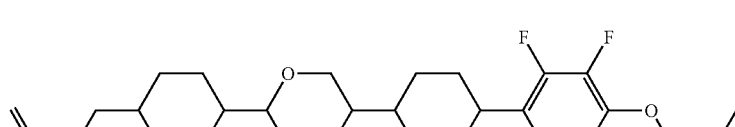 |
| 110 | 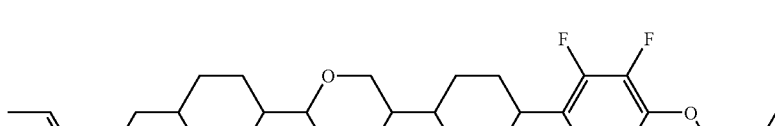 |
| 111 | 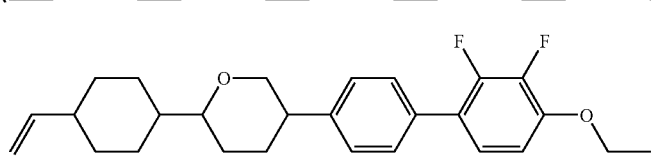 |

| No. | |
|---|---|
| 112 | 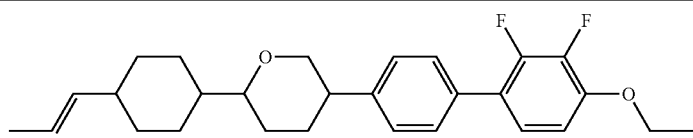 |
| 113 | 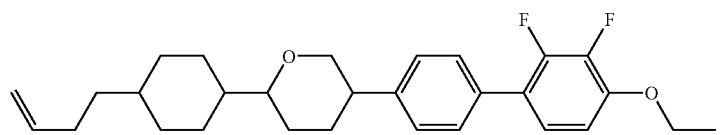 |
| 114 | 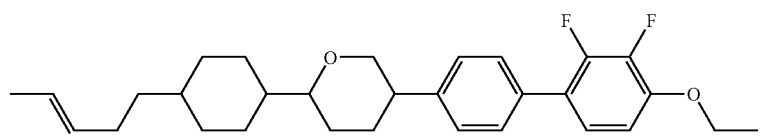 |
| 115 | 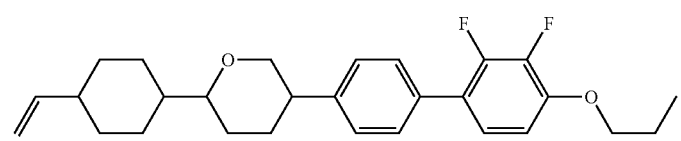 |
| 116 | 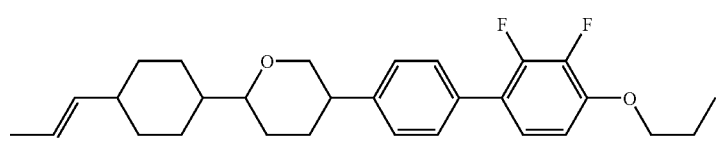 |
| 117 | 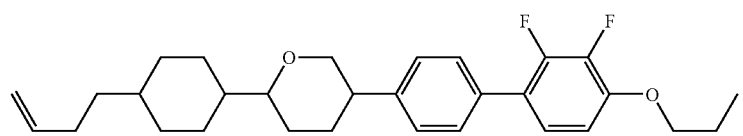 |
| 118 | 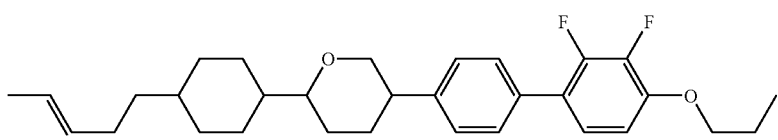 |
| 119 | 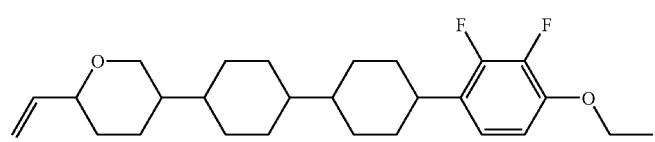 [SMILES: C=CC1CCC(C2CCC(C3CCC(c4ccc(OCC)c(F)c4F)CC3)CO2)CC1] |
| 120 | 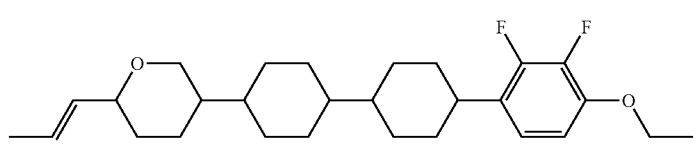 [SMILES: C/C=C/C1CCC(C2CCC(C3CCC(c4ccc(OCC)c(F)c4F)CC3)CC2)CO1] |
| 121 | 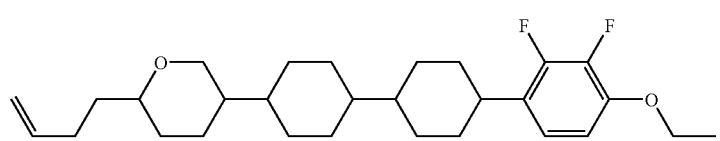 [SMILES: C=CCCC1CCC(C2CCC(C3CCC(c4ccc(OCC)c(F)c4F)CC3)CC2)CO1] |
| 122 | 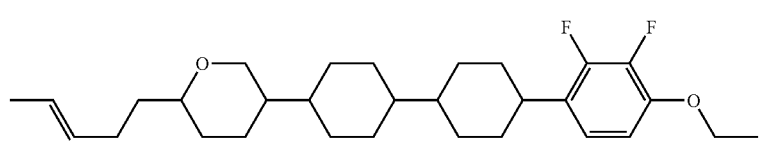 |

| No. | |
|---|---|
| 123 | 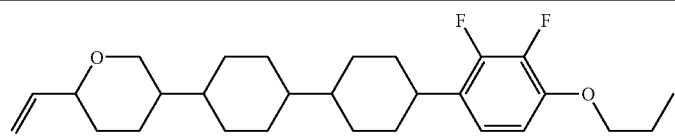 |
| 124 | 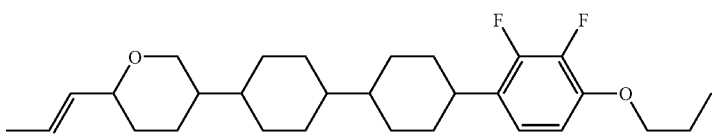 [SMILES: C/C=C/C1CCC(C2CCC(C3CCC(c4ccc(OCCC)c(F)c4F)CC3)CC2)CO1] |
| 125 | 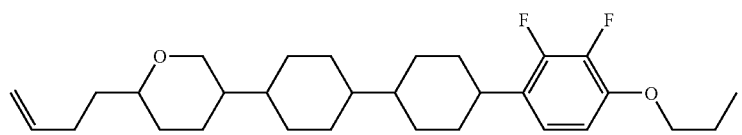 [SMILES: C=CCCC1CCC(C2CCC(C3CCC(c4ccc(OCCC)c(F)c4F)CC3)CC2)CO1] |
| 126 | 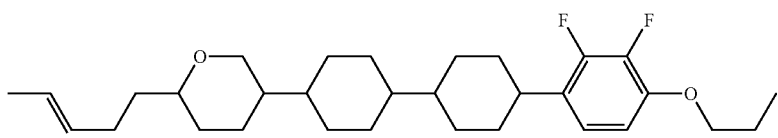 [SMILES: C/C=C/CCC1CCC(C2CCC(C3CCC(c4ccc(OCCC)c(F)c4F)CC3)CC2)CO1] |
| 127 | 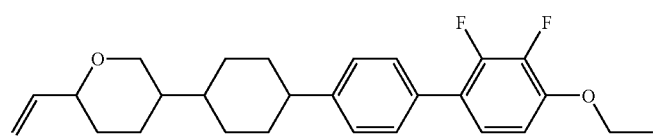 |
| 128 | 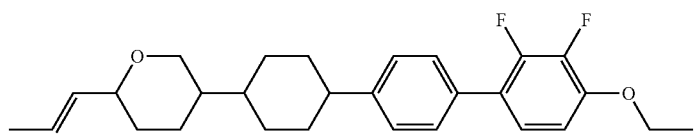 [SMILES: C/C=C/C1CCC(C2CCC(c3ccc(-c4ccc(OCC)c(F)c4F)cc3)CC2)CO1] |
| 129 | 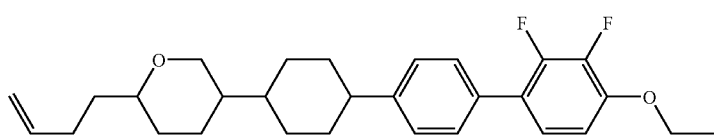 |
| 130 | 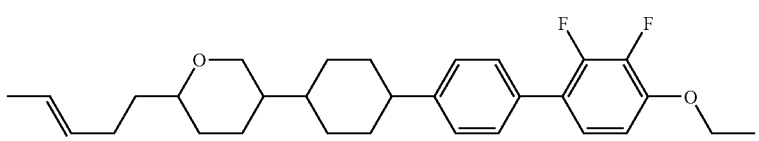 |
| 131 | 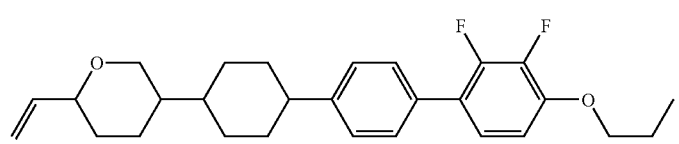 |
| 132 | 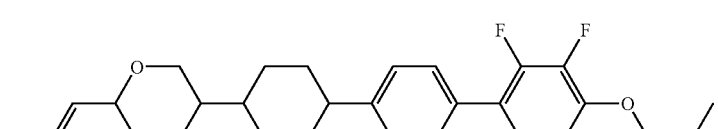 |
| 133 | 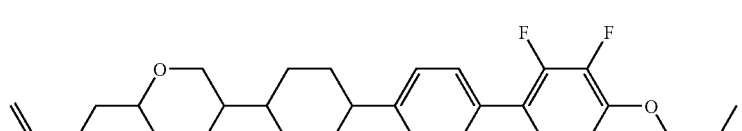 |

| No. | |
|---|---|
| 134 | 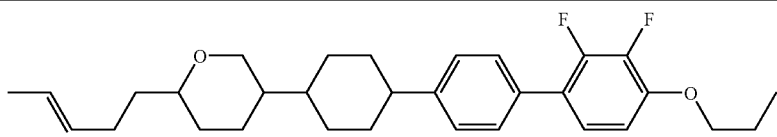 |
| 135 | 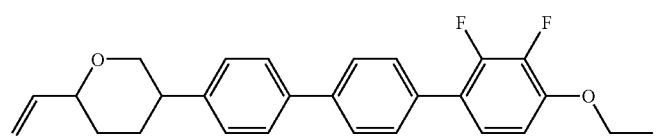 [SMILES: C=CC1CCC(c2ccc(-c3ccc(-c4ccc(OCC)c(F)c4F)cc3)cc2)CO1] |
| 136 | 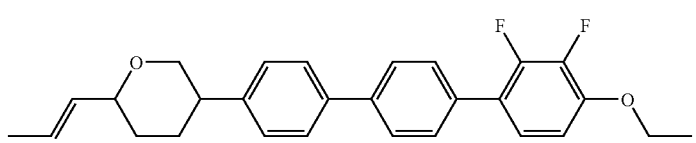 [SMILES: C/C=C/C1CCC(c2ccc(-c3ccc(-c4ccc(OCC)c(F)c4F)cc3)cc2)CO1] |
| 137 | 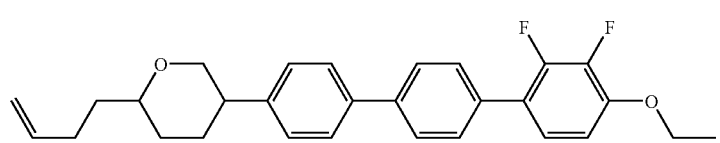 |
| 138 | 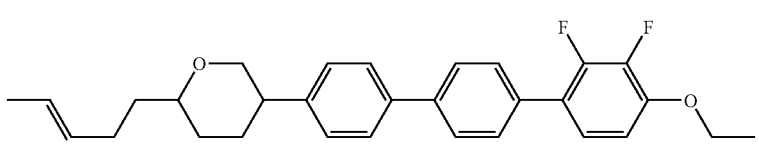 |
| 139 | 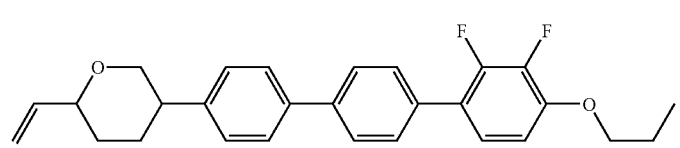 [SMILES: C=CC1CCC(c2ccc(-c3ccc(-c4ccc(OCCC)c(F)c4F)cc3)cc2)CO1] |
| 140 | 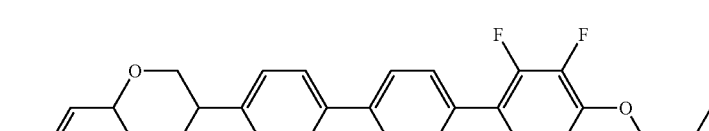 |
| 141 | 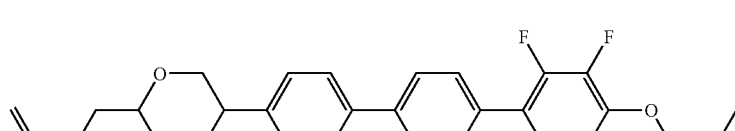 |
| 142 | 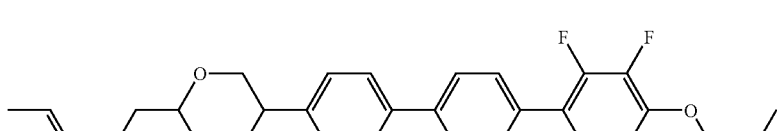 |
| 143 | 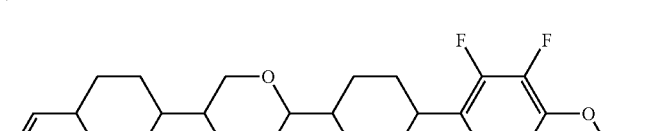 |
| 144 | 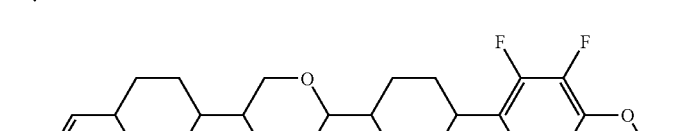 |

-continued
| No. | |
|---|---|
| 145 | 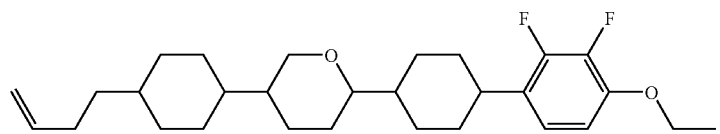 |
| 146 | 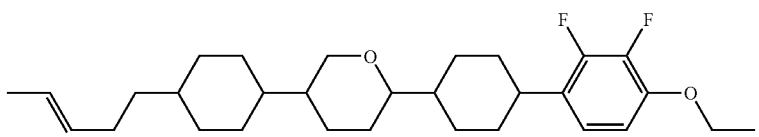 [SMILES: C/C=C/CCC1CCC(C2CCC(C3CCC(c4ccc(OCC)c(F)c4F)CC3)OC2)CC1] |
| 147 | 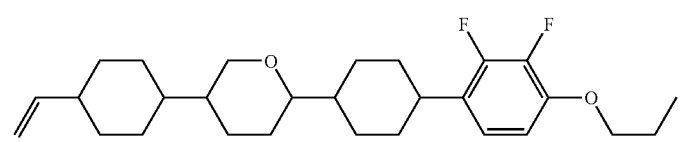 |
| 148 | 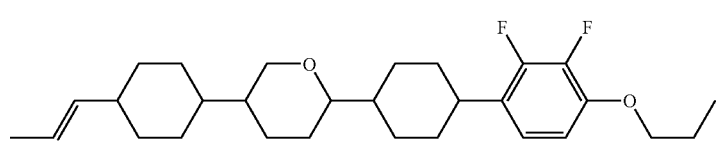 |
| 149 | 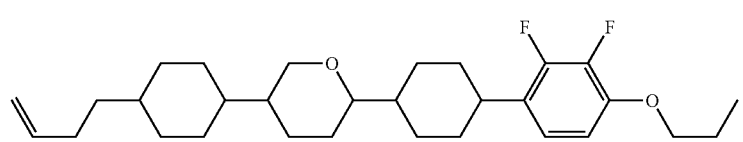 |
| 150 | 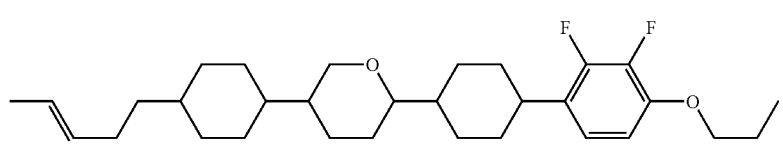 [SMILES: C/C=C/CCC1CCC(C2CCC(C3CCC(c4ccc(OCCC)c(F)c4F)CC3)OC2)CC1] |
| 151 | 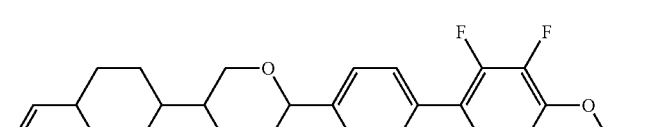 |
| 152 | 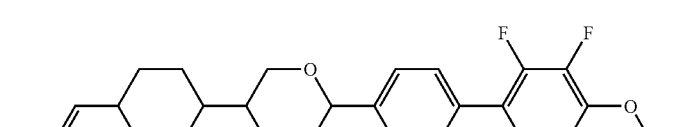 |
| 153 | 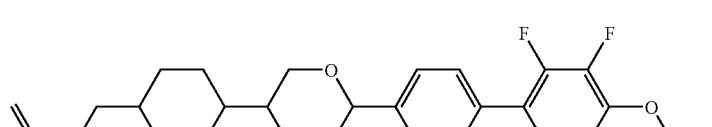 |
| 154 | 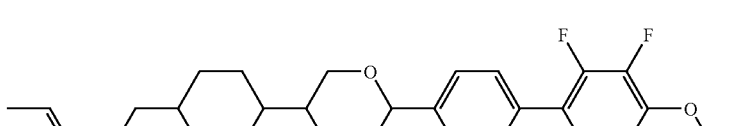 |
| 155 | 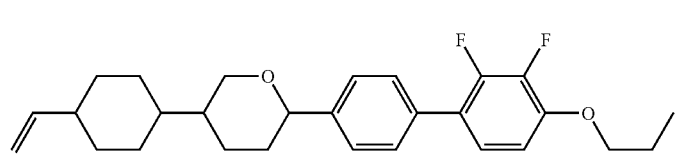 |

-continued
| No. | |
|---|---|
| 156 | 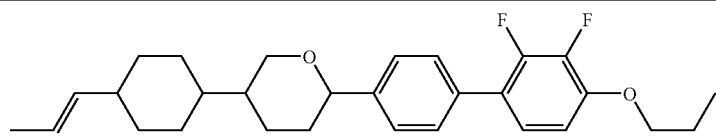 |
| 157 | 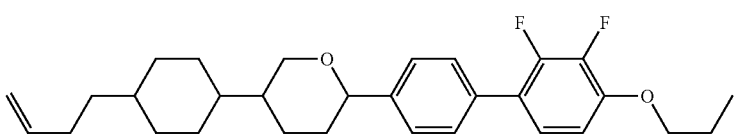 |
| 158 | 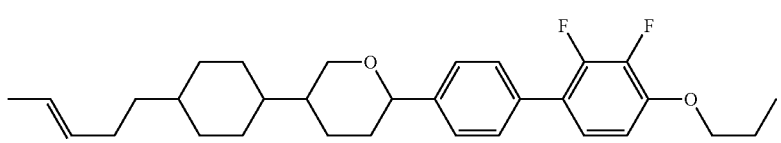 [SMILES: C/C=C/CCC1CCC(C2CCC(c3ccc(-c4ccc(OCCC)c(F)c4F)cc3)OC2)CC1] |
| 159 | 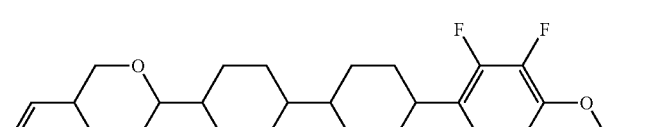 |
| 160 | 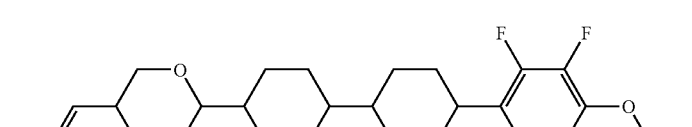 |
| 161 | 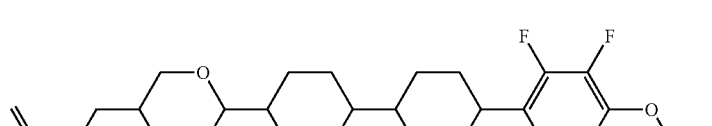 |
| 162 | 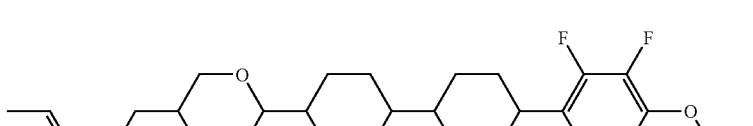 |
| 163 | 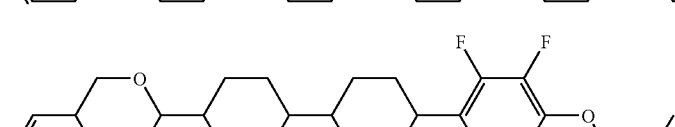 |
| 164 | 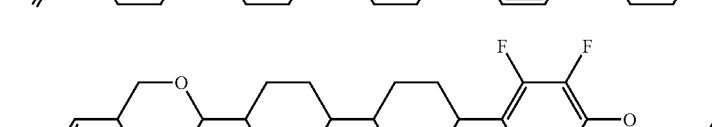 |
| 165 | 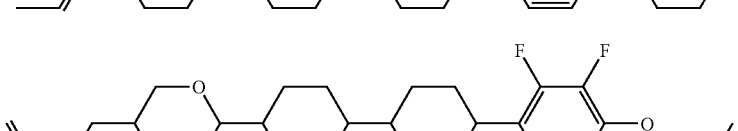 |
| 166 | 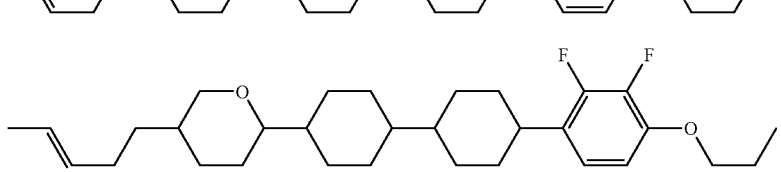 |

-continued
| No. | |
|---|---|
| 167 | 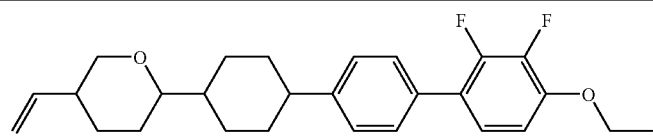 |
| 168 | 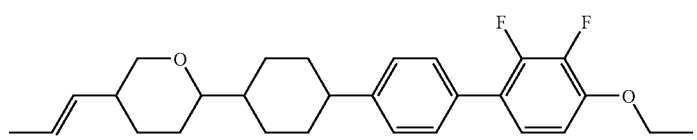 |
| 169 | 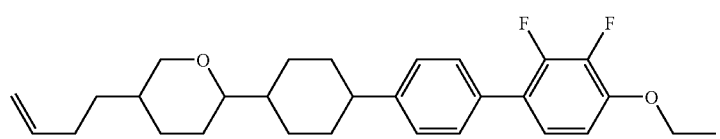 |
| 170 | 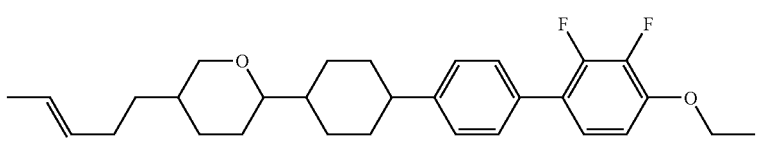 |
| 171 | 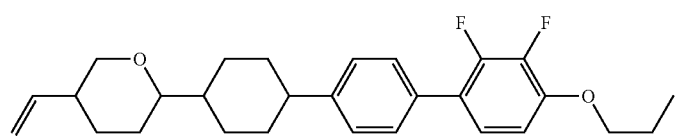 |
| 172 | 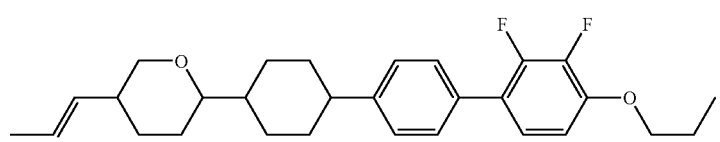 |
| 173 | 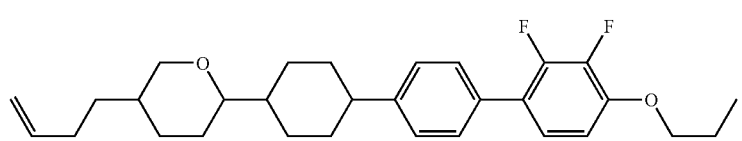 |
| 174 | 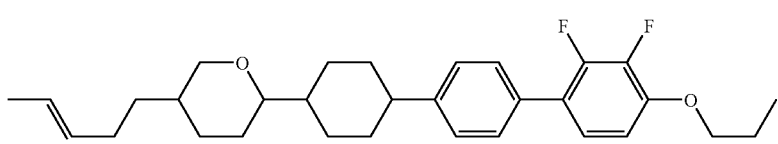 [SMILES: C/C=C/CCC1CCC(C2CCC(c3ccc(-c4ccc(OCCC)c(F)c4F)cc3)CC2)OC1] |
| 175 | 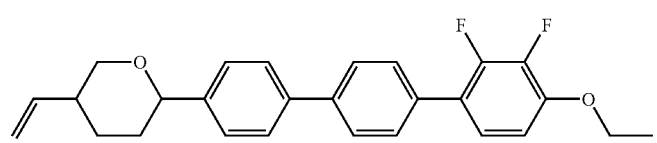 |
| 176 | 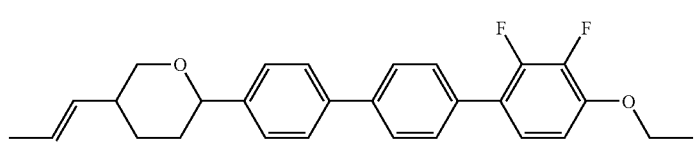 |
| 177 | 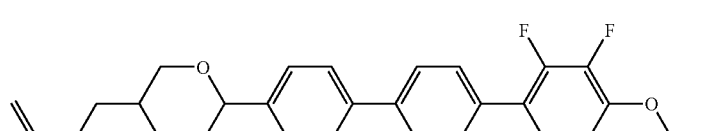 |

| No. | |
|---|---|
| 178 | 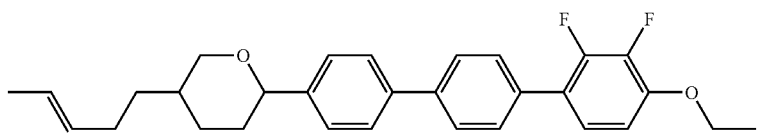 [SMILES: C/C=C/CCC1CCC(c2ccc(-c3ccc(-c4ccc(OCC)c(F)c4F)cc3)cc2)OC1] |
| 179 | 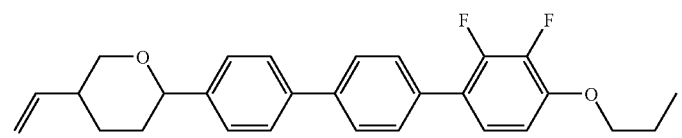 |
| 180 | 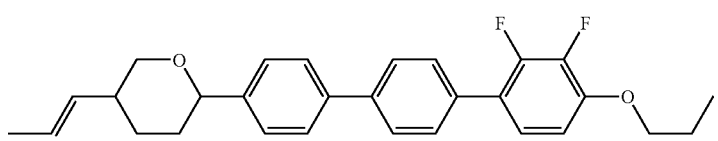 |
| 181 | 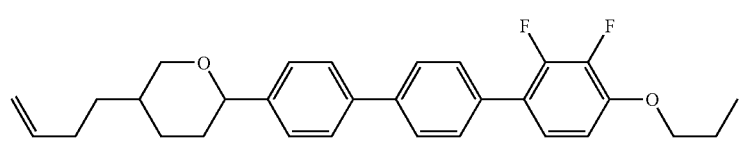 [SMILES: C=CCCC1CCC(c2ccc(-c3ccc(-c4ccc(OCCC)c(F)c4F)cc3)cc2)OC1] |
| 182 | 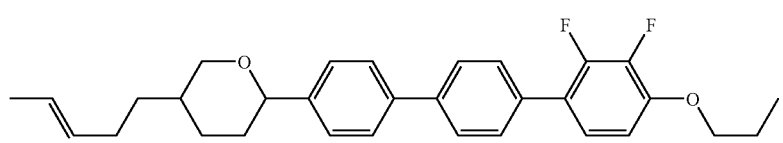 [SMILES: C/C=C/CCC1CCC(c2ccc(-c3ccc(-c4ccc(OCCC)c(F)c4F)cc3)cc2)OC1] |
| 183 | 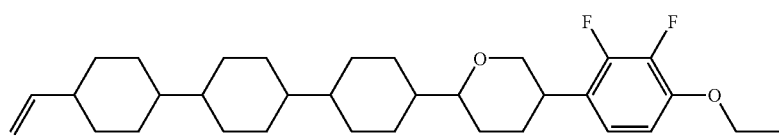 |
| 184 | 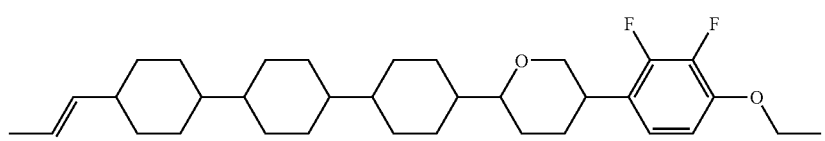 |
| 185 | 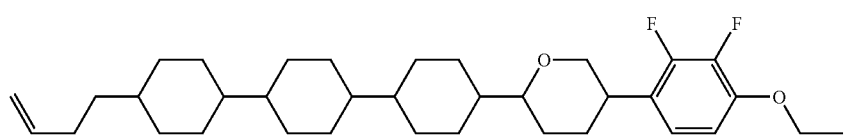 |
| 186 | 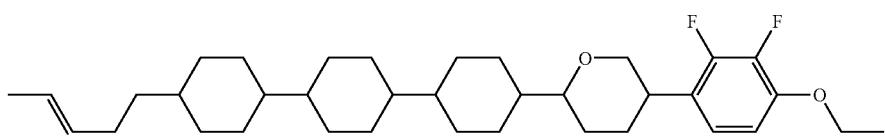 |
| 187 | 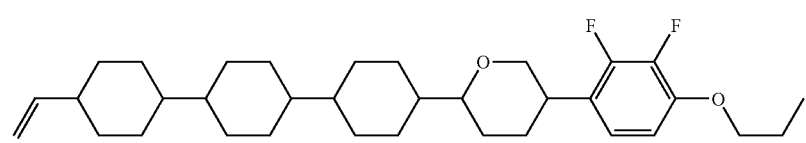 |
| 188 | 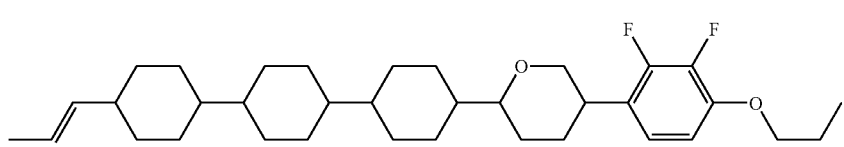 [SMILES: C/C=C/C1CCC(C2CCC(C3CCC(C4CCC(c5ccc(OCCC)c(F)c5F)CO4)CC3)CC2)CC1] |

US 8,372,306 B2
-continued
| No. | |
|---|---|
| 189 | 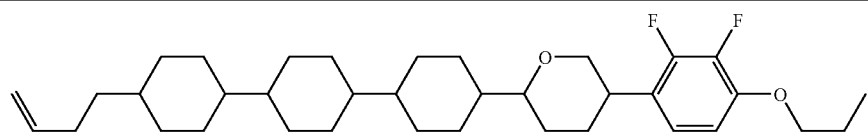 |
| 190 | 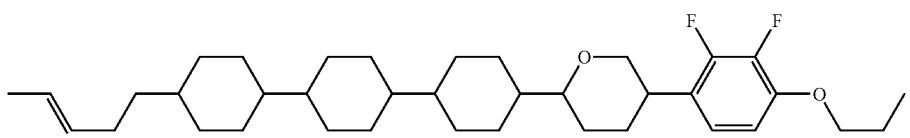 |
| 191 | 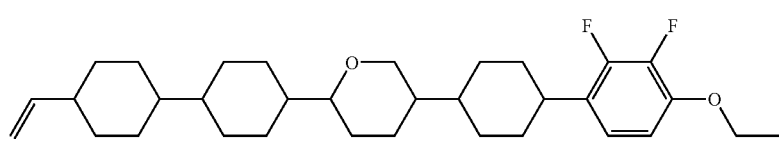 |
| 192 | 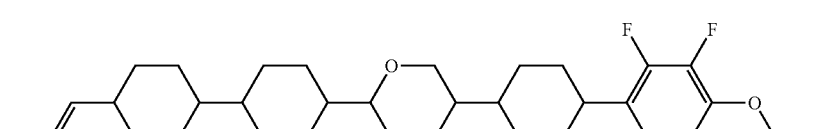 |
| 193 | 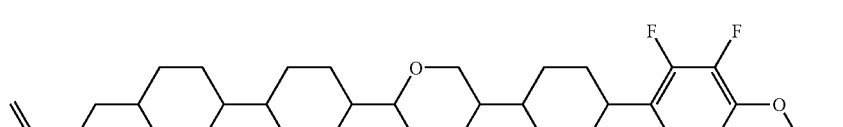 |
| 194 | 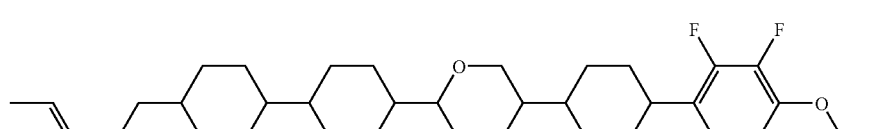 |
| 195 | 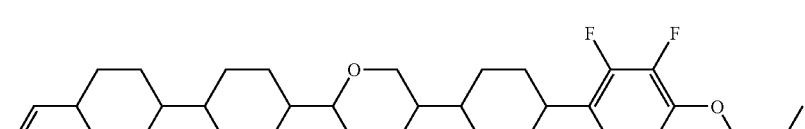 |
| 196 | 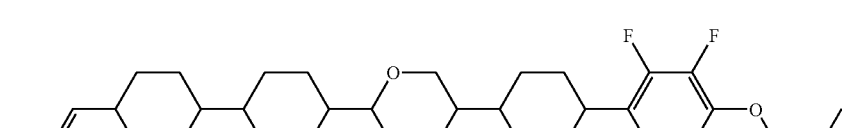 |
| 197 | 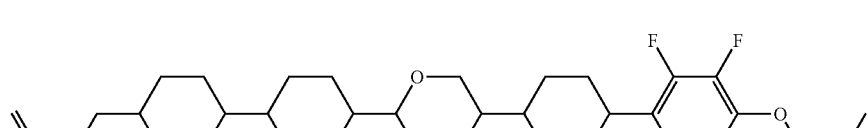 |
| 198 | 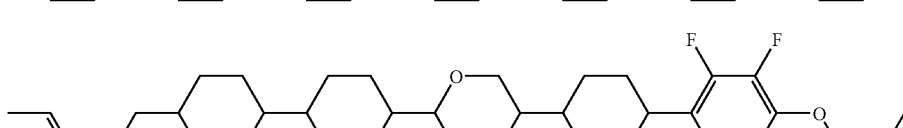 |
| 199 | 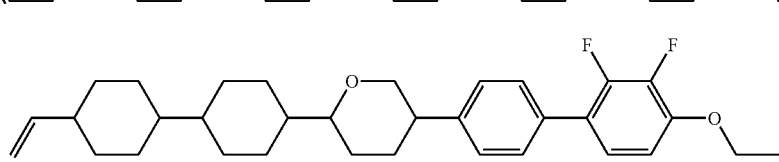 |

-continued
| No. |
|---|
| 200 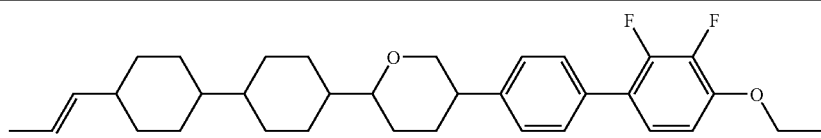 |
| 201 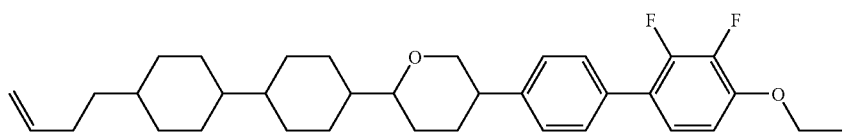 |
| 202 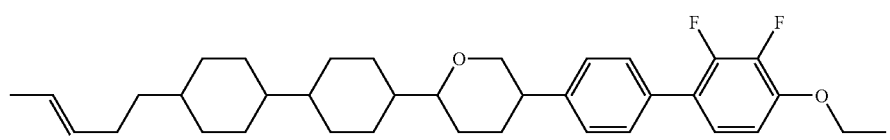 |
| 203 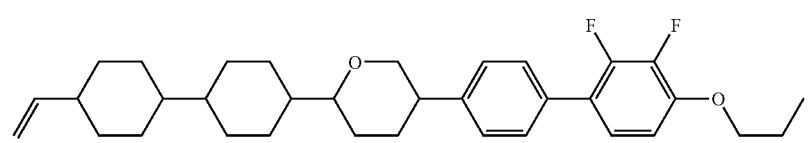 |
| 204 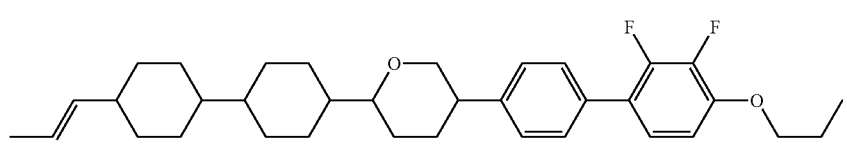 |
| 205 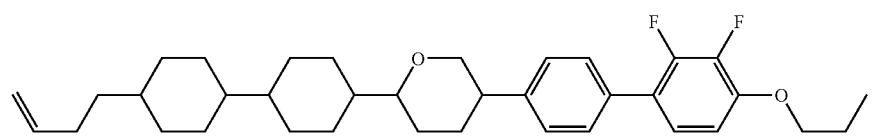 |
| 206 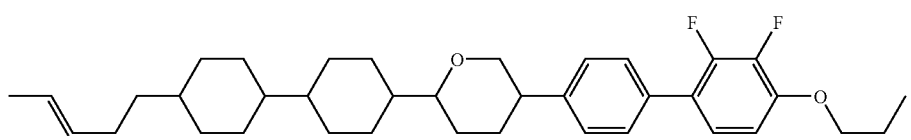 |
| 207 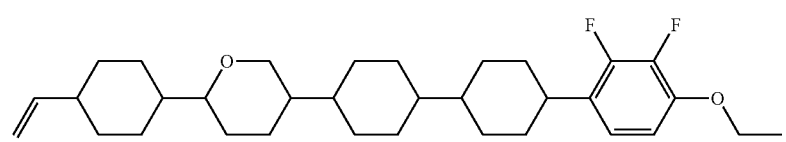 |
| 208 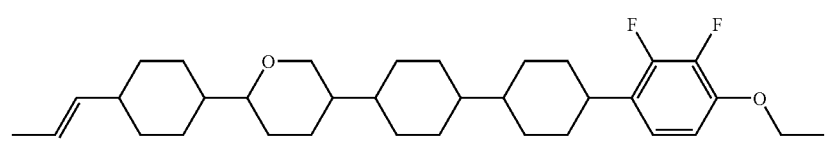 [SMILES: C/C=C/C1CCC(C2CCC(C3CCC(C4CCC(c5ccc(OCC)c(F)c5F)CC4)CO3)CC2)CC1] |
| 209 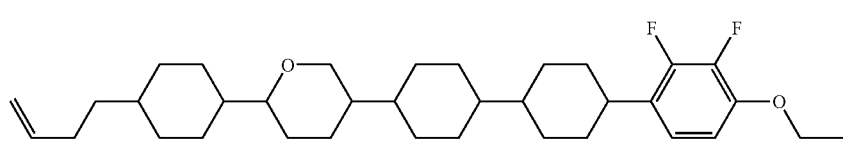 |
| 210 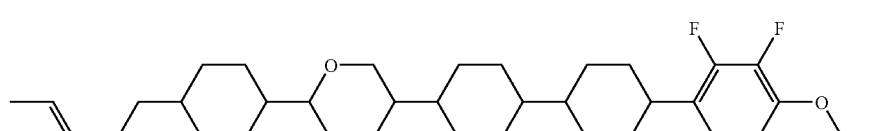 |

| No. |
|---|
| 211 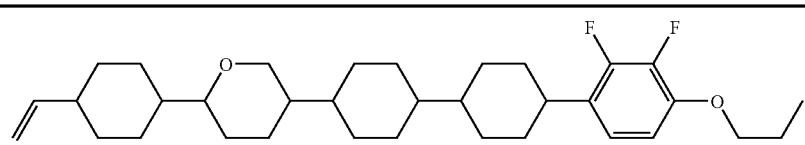 |
| 212 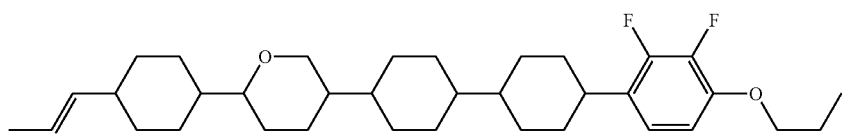 |
| 213 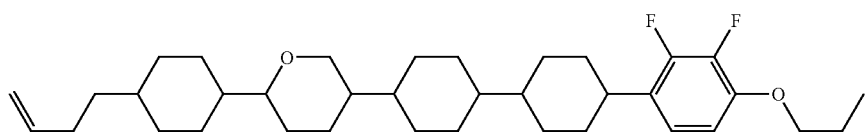 |
| 214 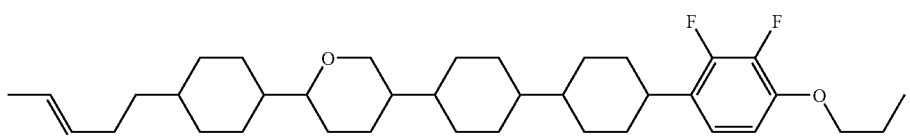 |
| 215 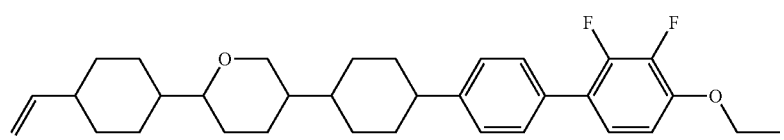 |
| 216 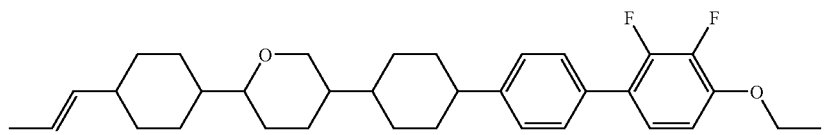 [SMILES: C/C=C/C1CCC(C2CCC(C3CCC(c4ccc(-c5ccc(OCC)c(F)c5F)cc4)CO3)CC2)CC1] |
| 217 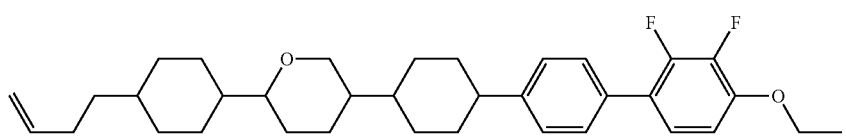 |
| 218 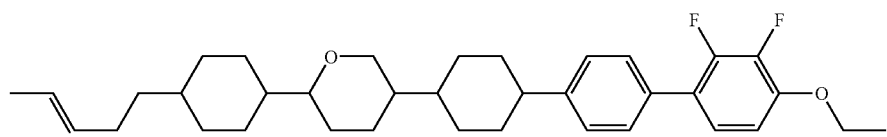 |
| 219 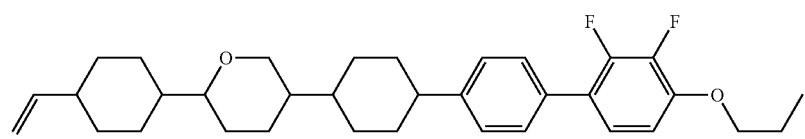 |
| 220 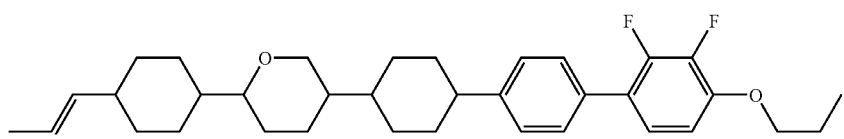 |
| 221 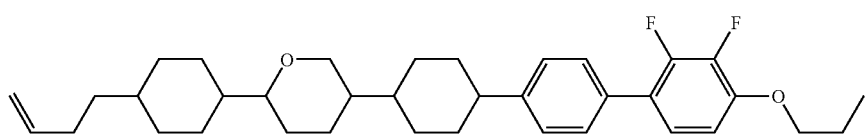 |

| No. |
|---|
| 222 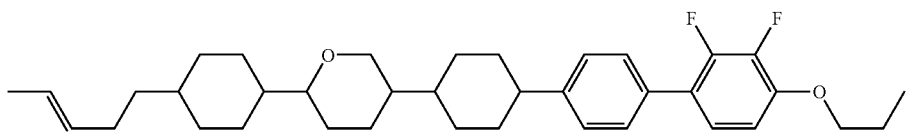 |
| 223 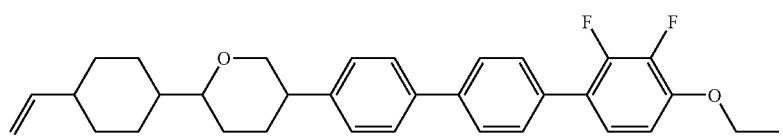 |
| 224 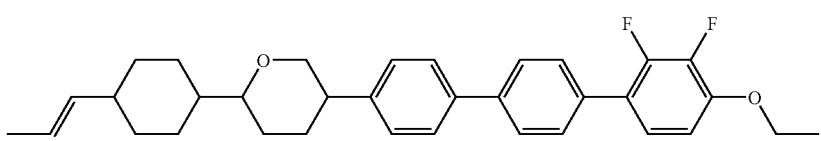 |
| 225 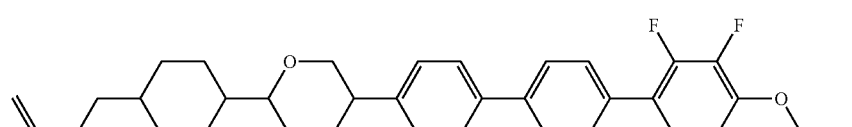 |
| 226 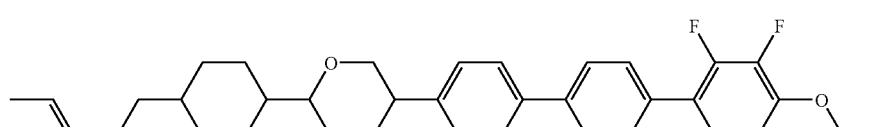 |
| 227 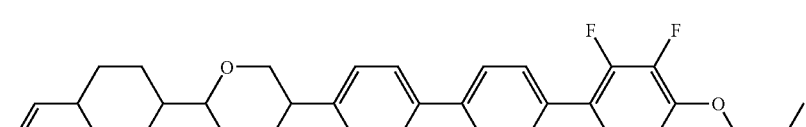 |
| 228 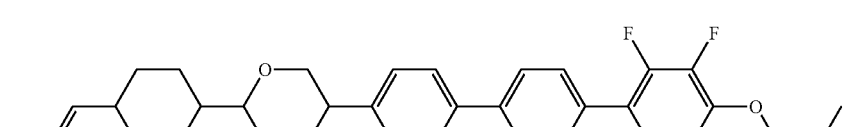 |
| 229 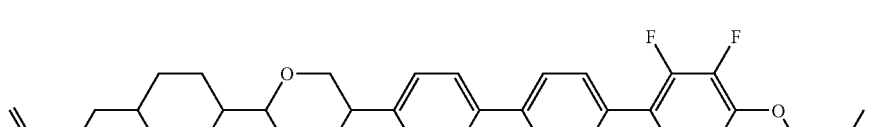 |
| 230 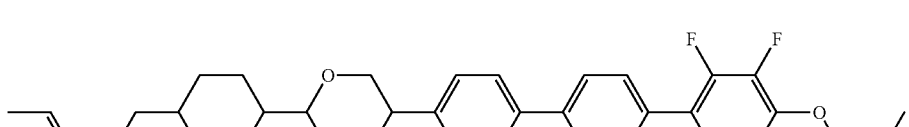 |
| 231 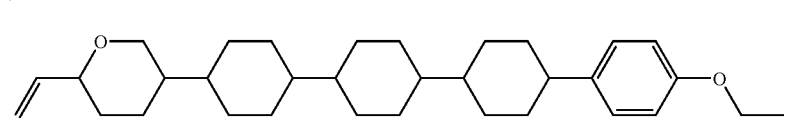 |
| 232 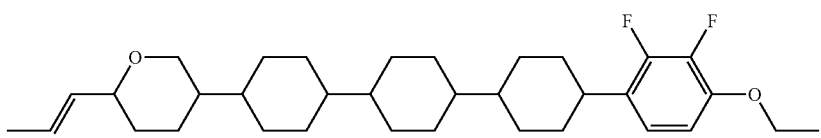 |

| No. | |
|---|---|
| 233 | 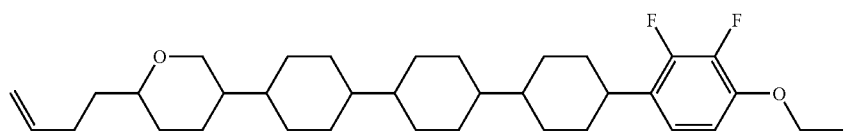 [SMILES: C=CCCC1CCC(C2CCC(C3CCC(C4CCC(c5ccc(OCC)c(F)c5F)CC4)CC3)CO2)CC1] |
| 234 | 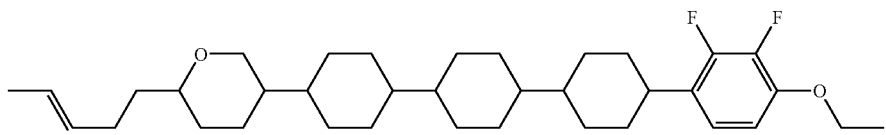 |
| 235 | 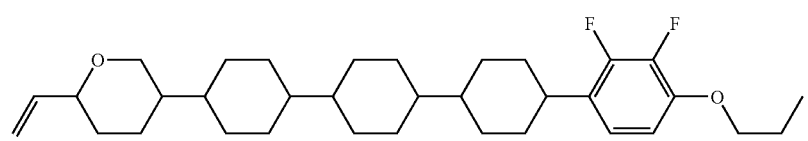 |
| 236 | 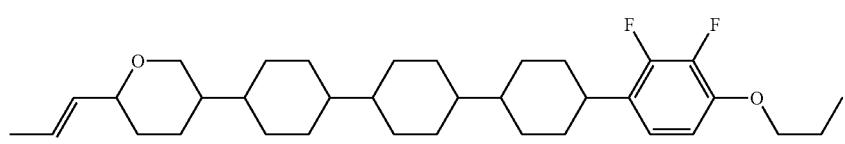 |
| 237 | 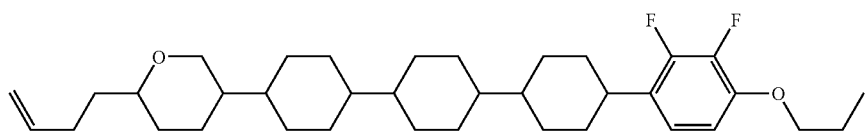 [SMILES: C=CCCC1CCC(C2CCC(C3CCC(C4CCC(c5ccc(OCCC)c(F)c5F)CC4)CC3)CO2)CC1] |
| 238 | 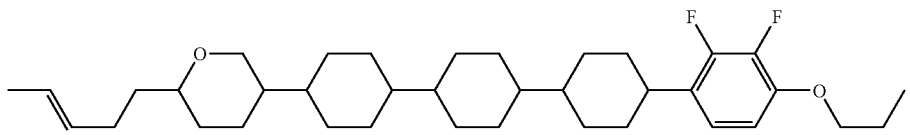 |
| 239 | 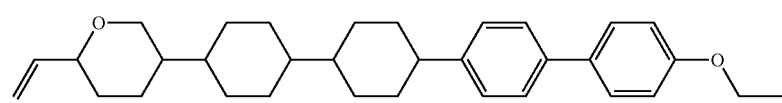 |
| 240 | 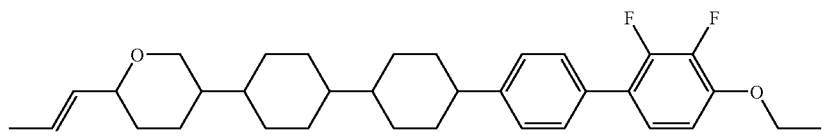 |
| 241 | 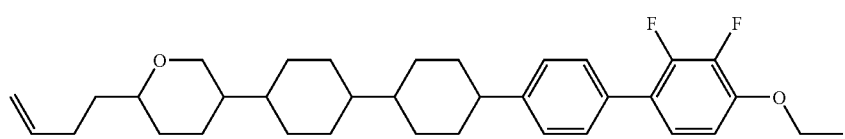 |
| 242 | 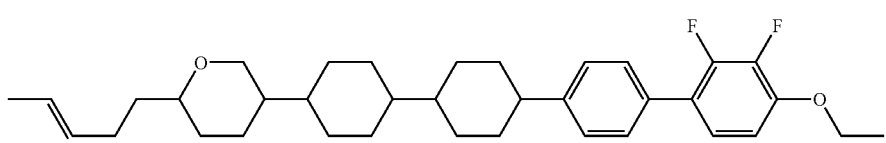 |
| 243 | 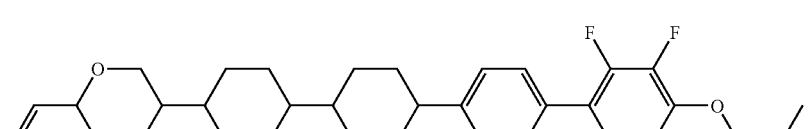 |

| No. |
|---|
| 244 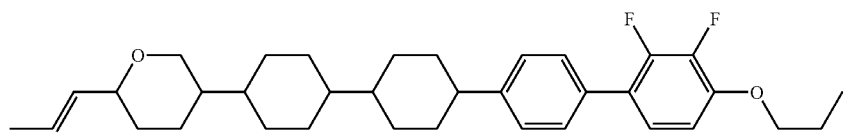 |
| 245 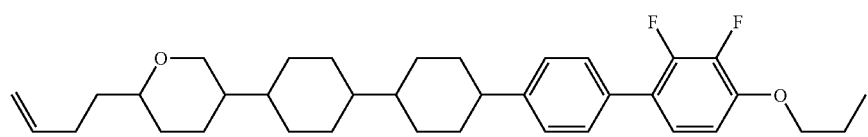 |
| 246 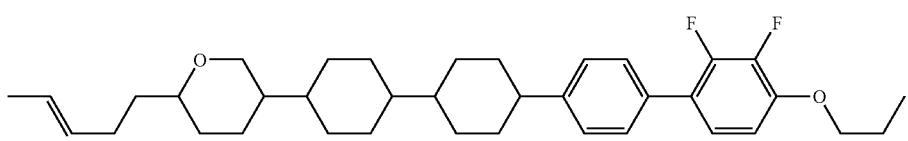 |
| 247 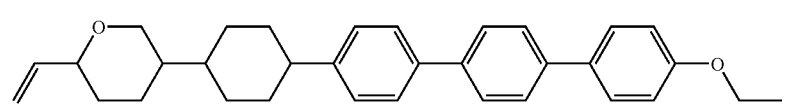 |
| 248 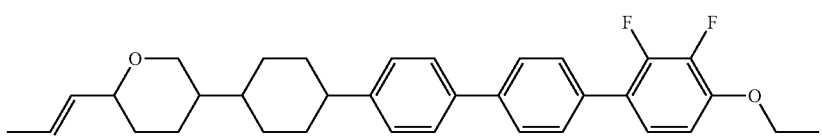 [SMILES: C/C=C/C1CCC(C2CCC(c3ccc(-c4ccc(-c5ccc(OCC)c(F)c5F)cc4)cc3)CC2)CO1] |
| 249 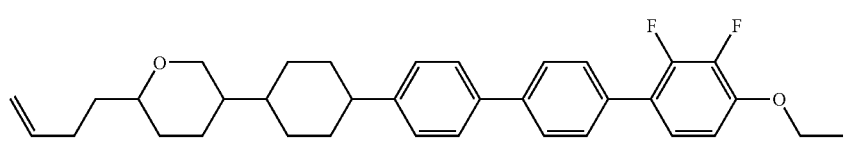 [SMILES: C=CCCC1CCC(C2CCC(c3ccc(-c4ccc(-c5ccc(OCC)c(F)c5F)cc4)cc3)CC2)CO1] |
| 250 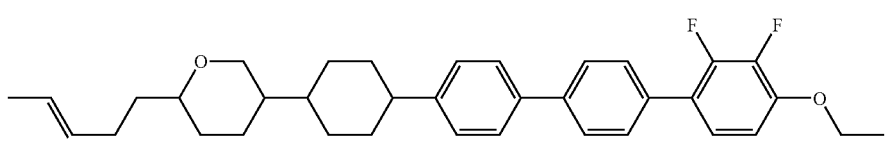 |
| 251 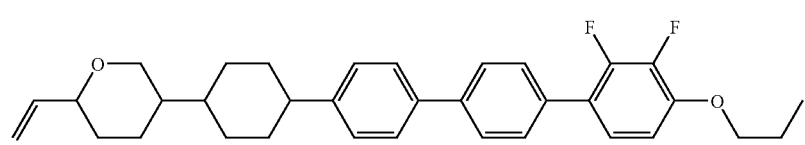 |
| 252 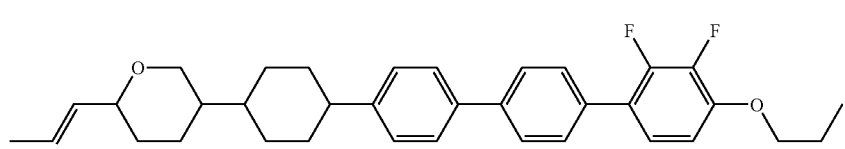 |
| 253 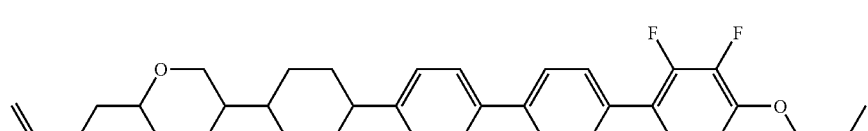 |
| 254 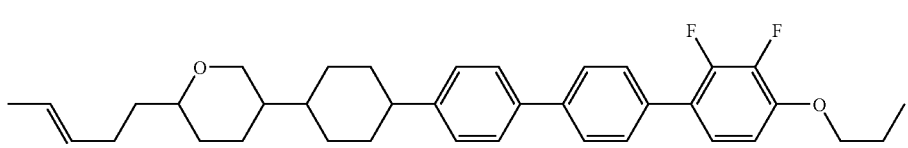 |

| No. | |
|---|---|
| 255 | 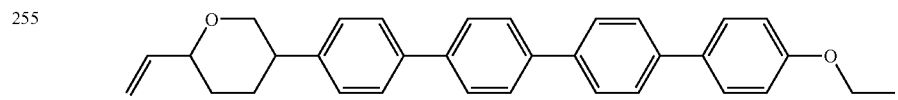 |
| 256 | 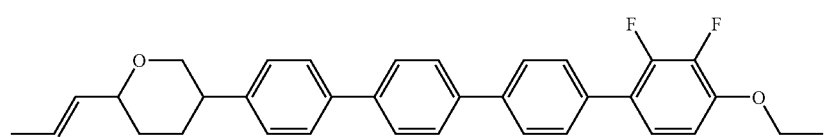 |
| 257 | 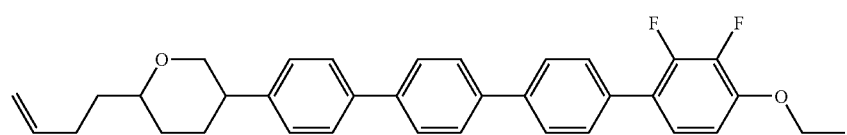 [SMILES: C=CCCC1CCC(c2ccc(-c3ccc(-c4ccc(-c5ccc(OCC)c(F)c5F)cc4)cc3)cc2)CO1] |
| 258 | 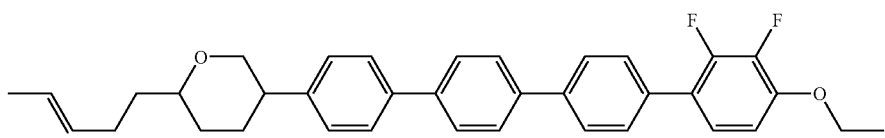 |
| 259 | 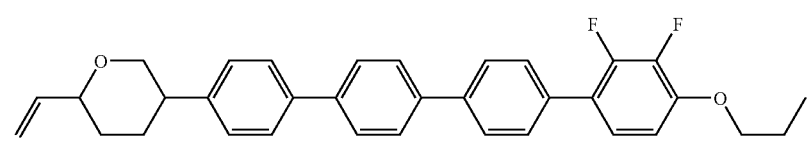 [SMILES: C=CC1CCC(c2ccc(-c3ccc(-c4ccc(-c5ccc(OCCC)c(F)c5F)cc4)cc3)cc2)CO1] |
| 260 | 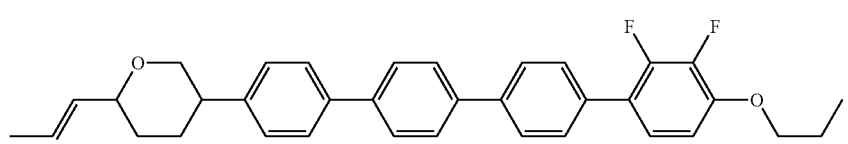 |
| 261 | 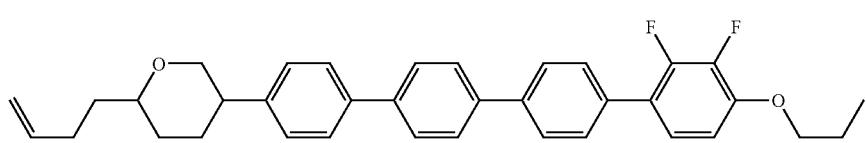 [SMILES: C=CCCC1CCC(c2ccc(-c3ccc(-c4ccc(-c5ccc(OCCC)c(F)c5F)cc4)cc3)cc2)CO1] |
| 262 | 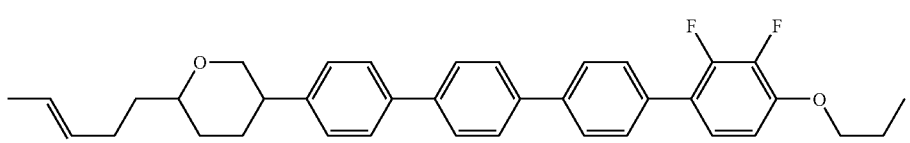 |
| 263 | 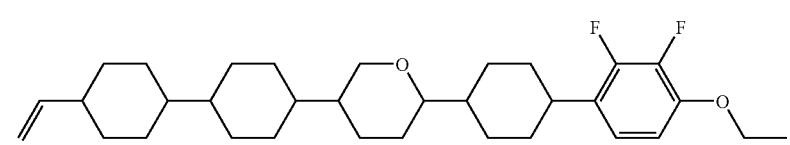 |
| 264 | 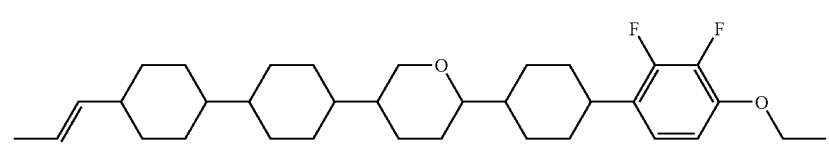 |
| 265 | 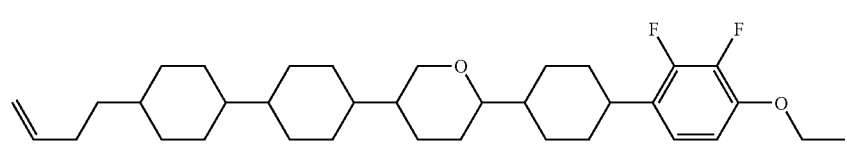 |

| No. | |
|---|---|
| 266 | 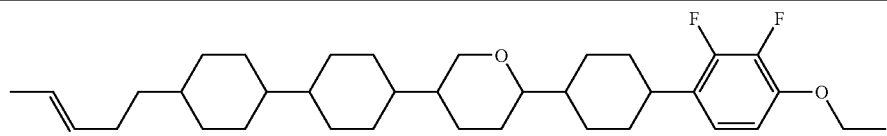 |
| 267 | 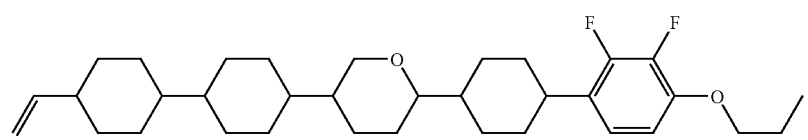 [SMILES: C=CC1CCC(C2CCC(C3CCC(C4CCC(c5ccc(OCCC)c(F)c5F)CC4)CC3)OC2)CC1] |
| 268 | 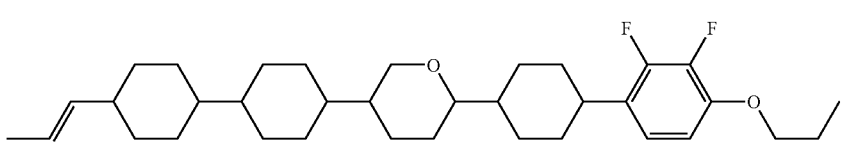 |
| 269 | 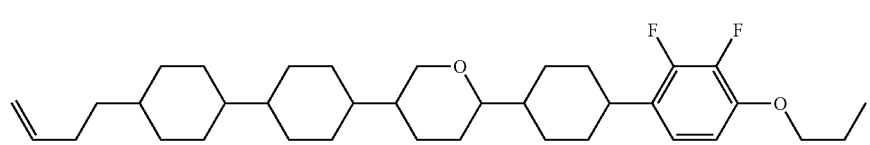 |
| 270 | 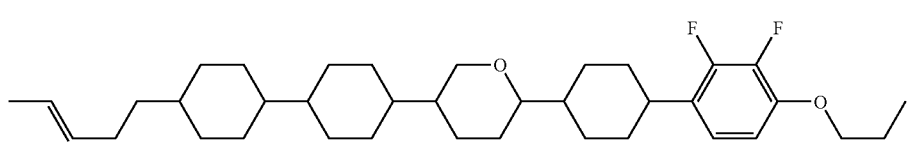 |
| 271 | 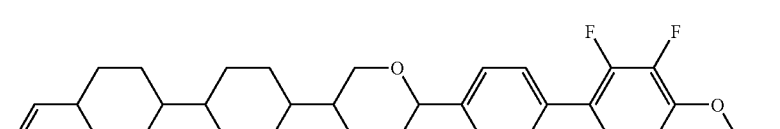 |
| 272 | 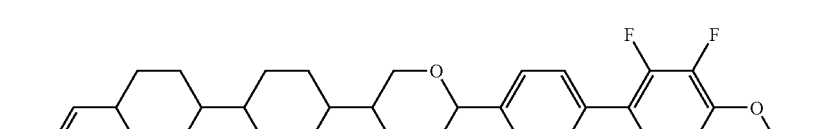 |
| 273 | 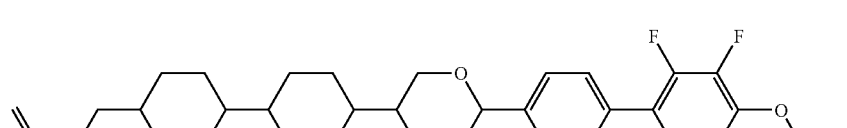 |
| 274 | 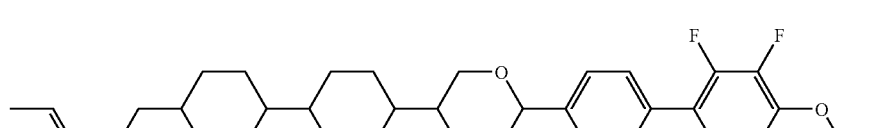 |
| 275 | 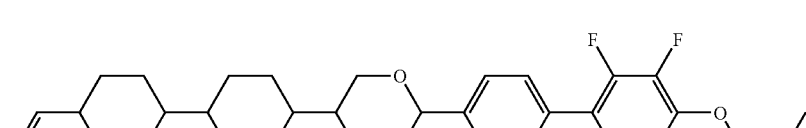 |
| 276 | 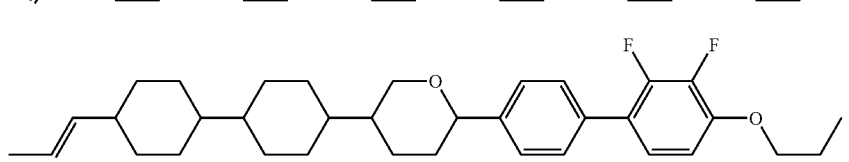 |

-continued
| No. | |
|---|---|
| 277 | 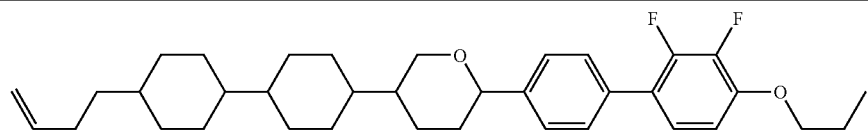 |
| 278 | 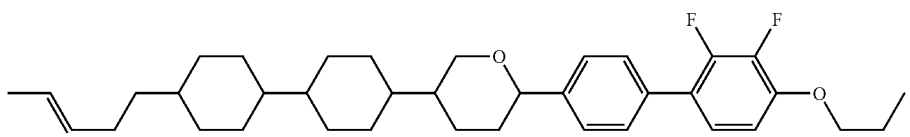 |
| 279 | 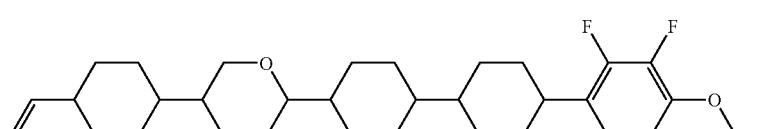 |
| 280 | 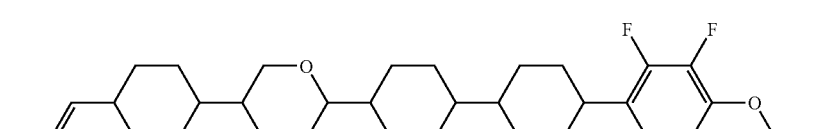 |
| 281 | 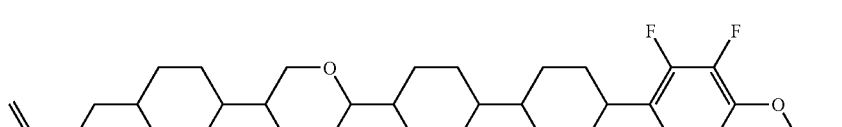 |
| 282 | 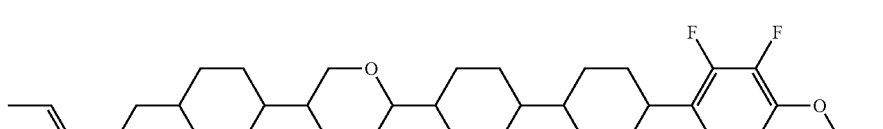 |
| 283 | 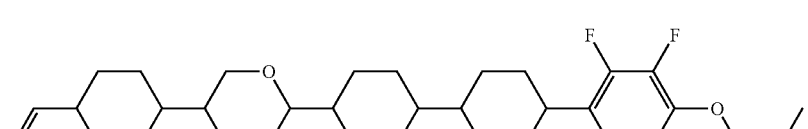 |
| 284 | 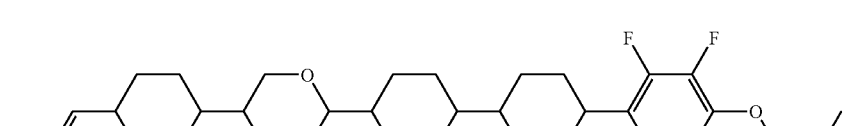 |
| 285 | 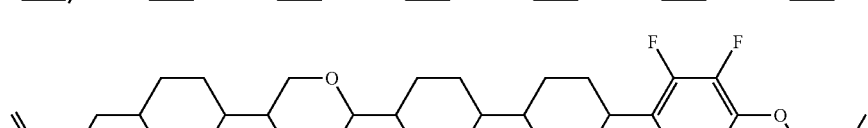 |
| 286 | 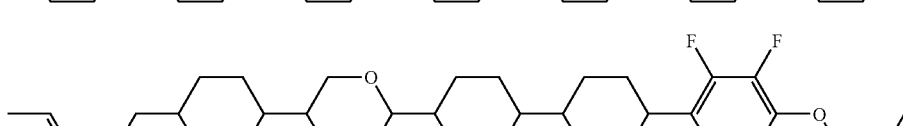 |
| 287 | 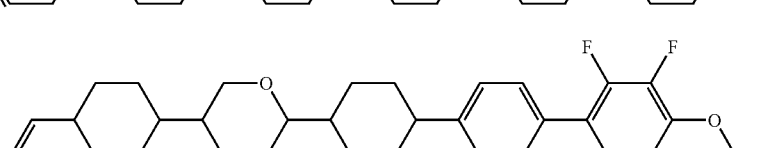 |

-continued
| No. | |
|---|---|
| 288 | 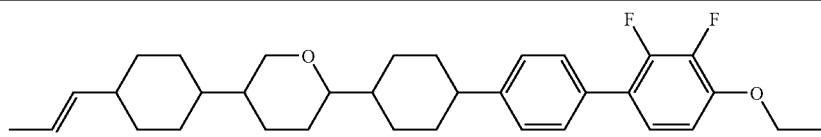 |
| 289 | 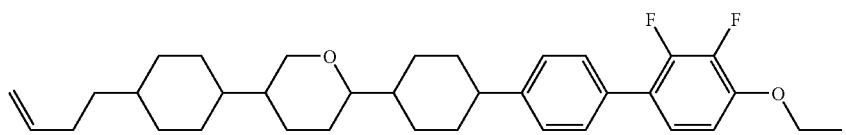 [SMILES: C=CCCC1CCC(C2CCC(C3CCC(c4ccc(-c5ccc(OCC)c(F)c5F)cc4)CC3)OC2)CC1] |
| 290 | 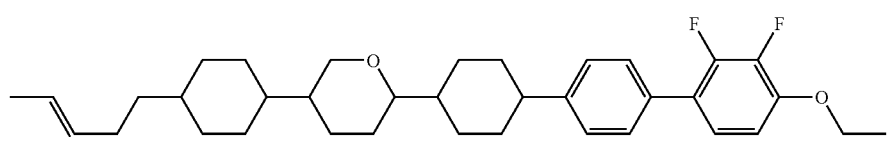 |
| 291 | 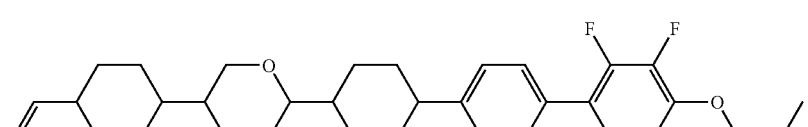 |
| 292 | 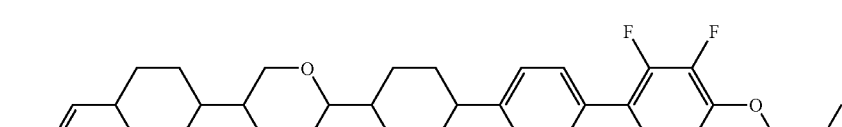 |
| 293 | 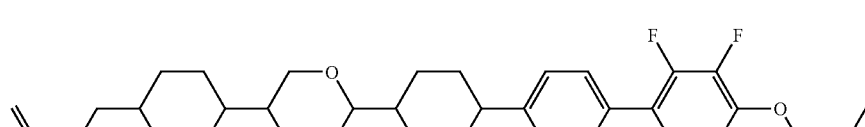 |
| 294 | 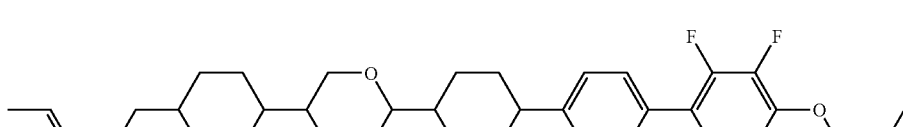 |
| 295 | 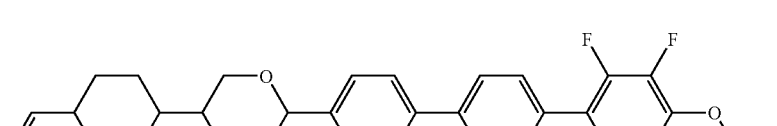 |
| 296 | 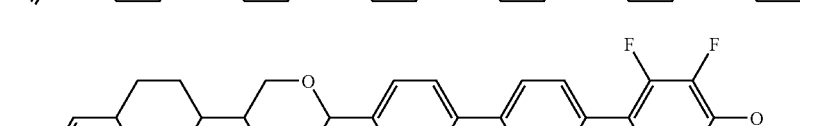 |
| 297 | 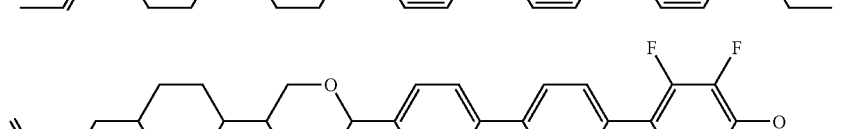 |
| 298 | 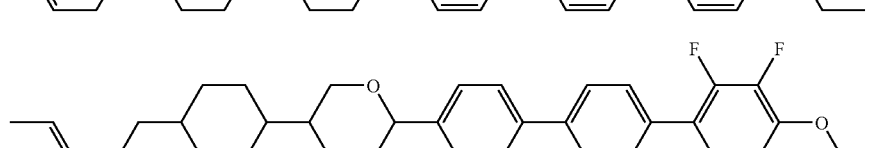 |

-continued
| No. |
|---|
| 299 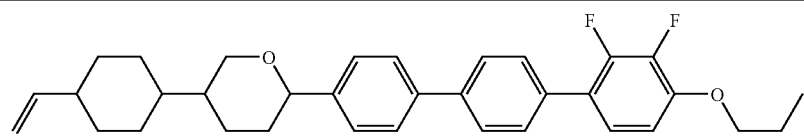 |
| 300 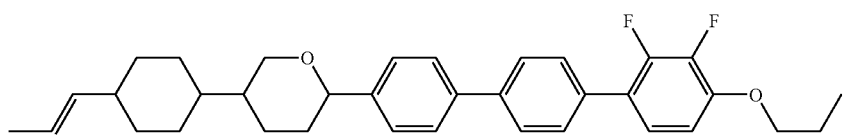 |
| 301 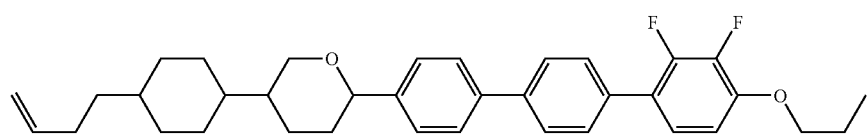 [SMILES: C=CCCC1CCC(C2CCC(c3ccc(-c4ccc(-c5ccc(OCCC)c(F)c5F)cc4)cc3)OC2)CC1] |
| 302 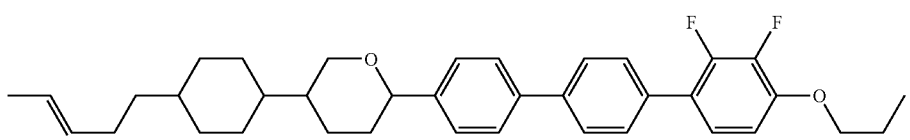 [SMILES: C/C=C/CCC1CCC(C2CCC(c3ccc(-c4ccc(-c5ccc(OCCC)c(F)c5F)cc4)cc3)OC2)CC1] |
| 303 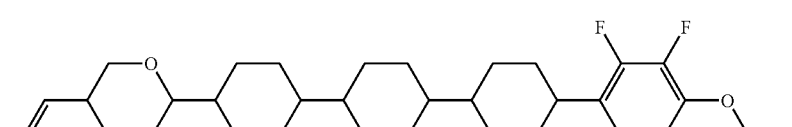 |
| 304 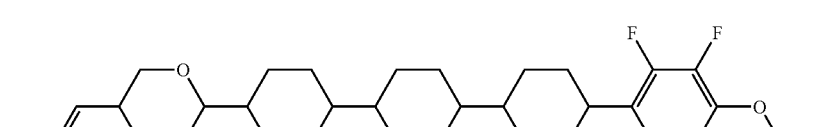 |
| 305 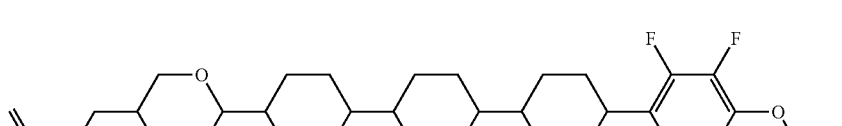 |
| 306 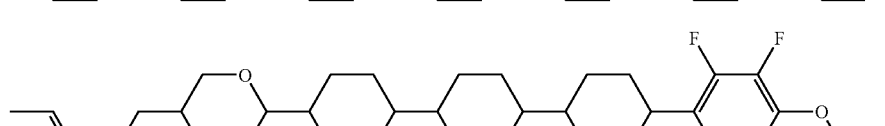 |
| 307 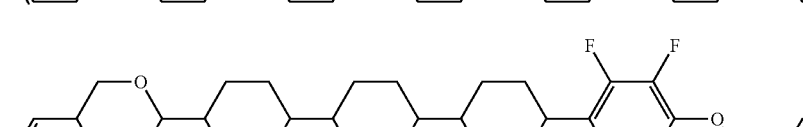 |
| 308 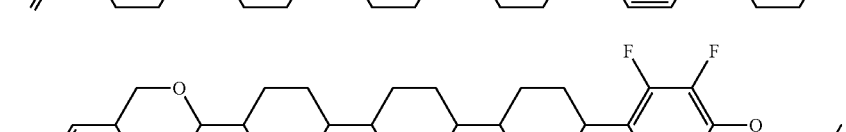 |
| 309 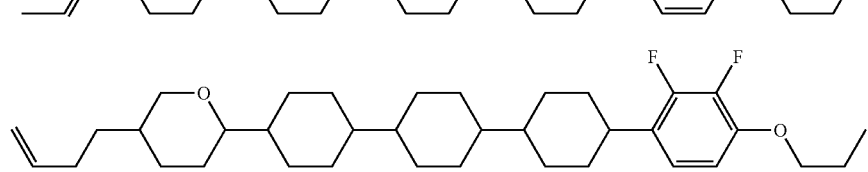 |

-continued
| No. | |
|---|---|
| 310 | 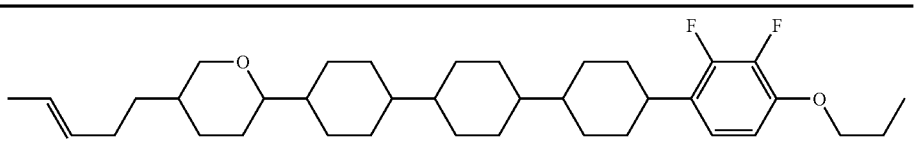 |
| 311 | 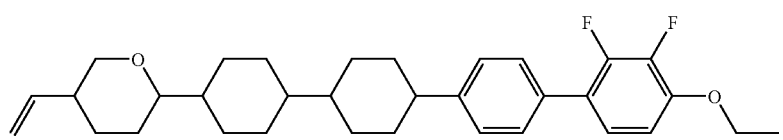 |
| 312 | 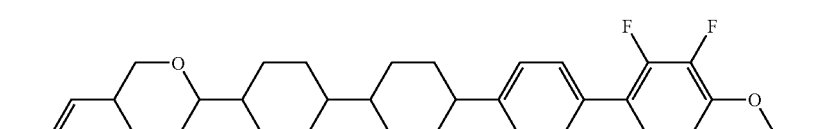 |
| 313 | 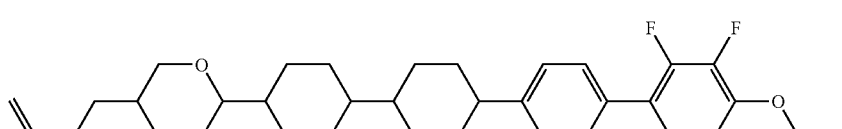 |
| 314 | 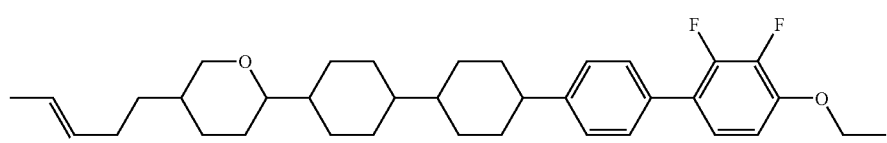 |
| 315 | 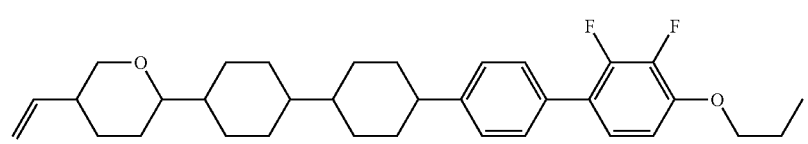 |
| 316 | 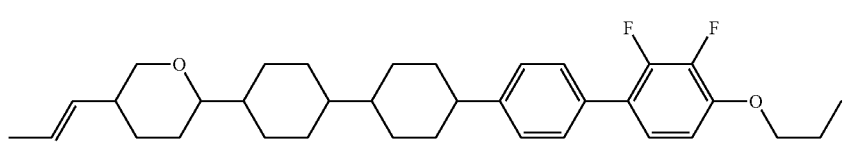 |
| 317 | 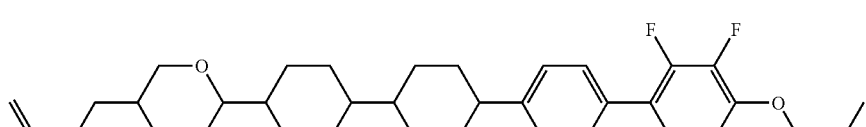 |
| 318 | 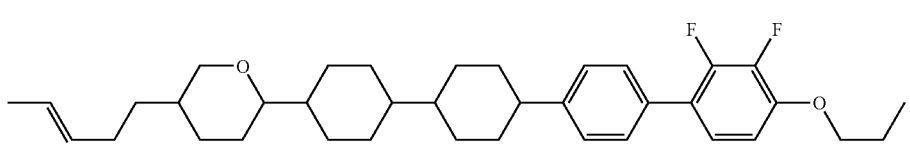 [SMILES: C/C=C/CCC1CCC(C2CCC(C3CCC(C4CCC(c5ccc(OCCC)c(F)c5F)CC4)CC3)CC2)OC1] |
| 319 | 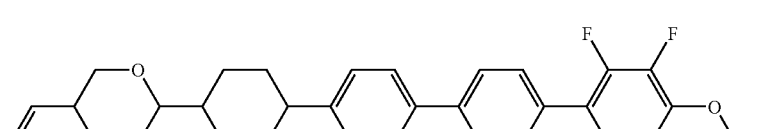 |
| 320 | 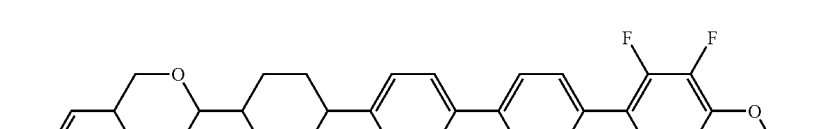 |

-continued
| No. | |
|---|---|
| 321 | 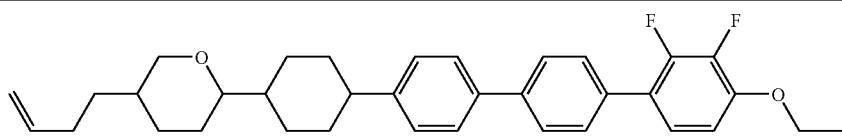 |
| 322 | 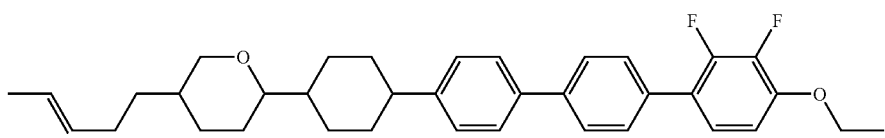 |
| 323 | 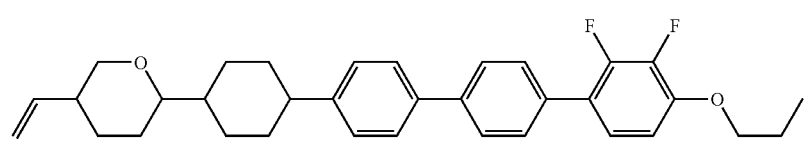 [SMILES: C=CC1CCC(C2CCC(c3ccc(-c4ccc(-c5ccc(OCCC)c(F)c5F)cc4)cc3)CC2)OC1] |
| 324 | 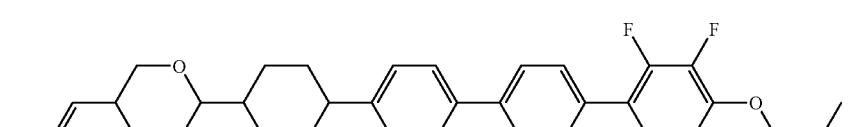 |
| 325 | 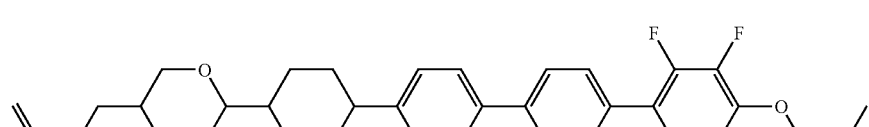 |
| 326 | 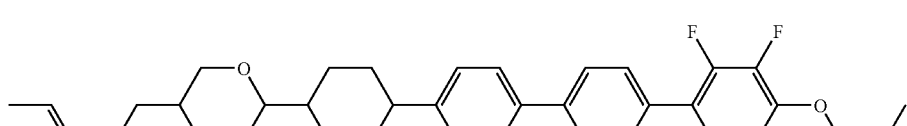 |
| 327 | 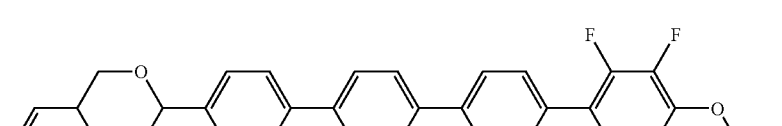 |
| 328 | 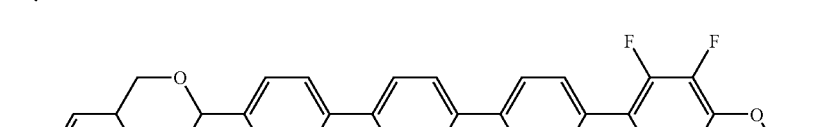 |
| 329 | 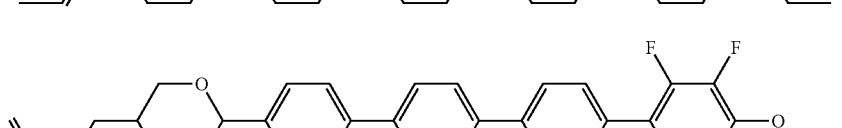 |
| 330 | 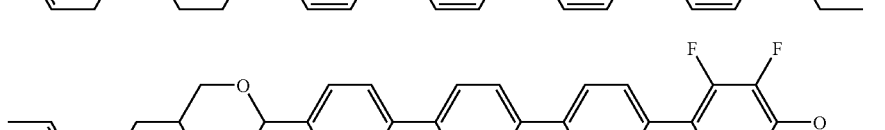 |
| 331 | 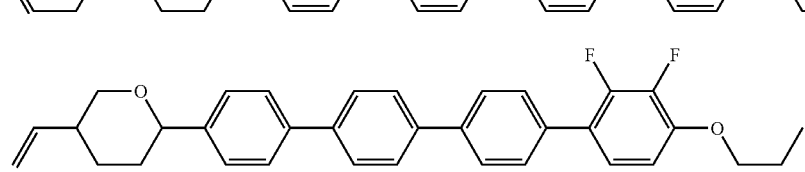 |

-continued

| No. | |
|---|---|
| 332 | 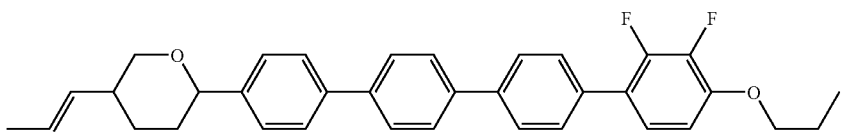 |
| 333 | 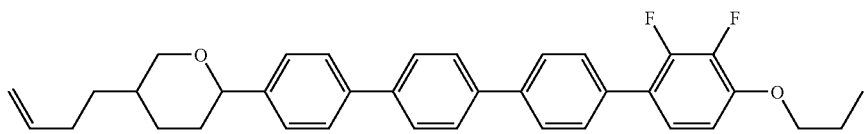 |
| 334 | 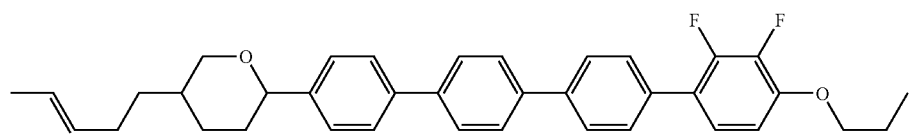 |

Comparative Example 1

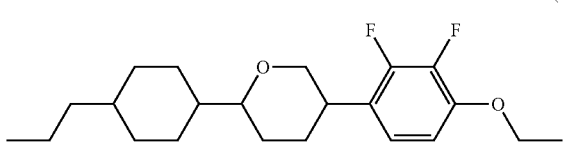
(b)

A compound (b) was synthesized according to the synthesis method disclosed in JP 2000-8040 A by Chisso Corporation.

The chemical shifts δ (ppm) in $^1$H-NMR analysis of the compound (b) were as follow. The solvent for measurement was $CDCl_3$.

Chemical shift δ (ppm): 6.80 (m, 1H), 6.67 (m, 1H), 4.09 (q, 2H), 4.00 (m, 1H), 3.37 (t, 1H), 3.1-3.0 (m, 2H), 2.1-0.8 (m, 24H)

The resulting compound (b) had phase transition temperatures (° C.) of C 65.2-65.5 N 140.0 Iso.

A liquid crystal composition B containing 15% by weight of the compound (b) and 85% by weight of the mother liquid crystals A was prepared. The resulting liquid crystal composition B was measured for characteristics, and the characteristics of the compound (b) were calculated by extrapolation with the measured values. The extrapolated values were as follows.

Maximum temperature (NI)=121.3° C.
Dielectric anisotropy (Δε)=−7.3
Refractive index anisotropy (Δn)=0.107
Viscosity (η)=61.4 mPa·s Example 3

A liquid crystal composition C containing 15% by weight of the compound No. 7 and 85% by weight of the mother liquid crystals A was prepared. The resulting liquid crystal composition C was measured for characteristics, and the characteristics of the compound No. 7 were calculated by extrapolation with the measured values. The extrapolated values were as follows.

Maximum temperature (NI)=131.6° C.
Dielectric anisotropy (Δε)=−7.6
Refractive index anisotropy (Δn)=0.112
Viscosity (η)=61.6 mPa·s It is understood from the comparison between the compound (b) in Comparative Example 1 and the compound No. 7 in Example 1 that the compound No. 7 according to the invention is superior since it has a high maximum temperature and a negatively large dielectric anisotropy (Δε).

Examples of Liquid Crystal Composition

Representative examples of the liquid crystal composition of the invention are shown in Examples 4 to 12. First, the compounds as the components of the compositions and the amounts thereof (% by weight) are shown. The compounds are expressed by the symbols for the left terminal group, the boding group, the ring structure and the right terminal group according to the definition in Table 1.

TABLE 1

| Method of Description of Compound using Symbols R—(A$_1$)—Z$_1$—...—Z$_n$—(A$_n$)—R' | |
|---|---|
| | Symbol |
| (1) Left Terminal Group R— | |
| $C_nH_{2n+1}$— | n- |
| $C_nH_{2n+1}O$— | nO— |
| $C_mH_{2m+1}OC_nH_{2n}$— | mOn- |
| $CH_2=CH$— | V- |
| $C_nH_{2n+1}$—CH=CH— | nV- |
| $CH_2=CH$—$C_nH_{2n}$— | Vn- |
| $C_mH_{2m+1}$—CH=CH—$C_nH_{2n}$— | mVn- |
| $CF_2=CH$— | VFF- |
| $CF_2=CH$—$C_nH_{2n}$— | VFFn- |
| (2) Right Terminal Group R'— | |
| —$C_nH_{2n+1}$ | -n |
| —$OC_nH_{2n+1}$ | —On |
| —CH=$CH_2$ | —V |
| —CH=CH—$C_nH_{2n+1}$ | -Vn |
| —$C_nH_{2n}$—CH=$CH_2$ | -nV |
| —CH=$CF_2$ | -VFF |
| —$COOCH_3$ | -EMe |

TABLE 1-continued

Method of Description of Compound using Symbols
R—(A₁)—Z₁— ... —Zₙ—(Aₙ)—R'

| | Symbol |
|---|---|
| (3) Bonding Group —$Z_n$— | |
| —$C_nH_{2n}$— | n |
| —COO— | E |
| —CH=CH— | V |
| —CH₂O— | 1O |
| —OCH₂— | O1 |
| —SiH₂— | Si |
| —CF₂O— | X |
| (4) Ring Structure —$A_n$— | |
| tetrahydropyran (2,5-linked) | Dh |
| tetrahydropyran (2,5-linked, alt.) | dh |
| cyclohexane | H |
| cyclohexene | Ch |
| benzene | B |
| 2-fluorobenzene | B(2F) |
| 3-fluorobenzene | B(3F) |
| 3,5-difluorobenzene | B(3F,5F) |
| 2,3-difluorobenzene | B(2F,3F) |
| 2-fluoro-3-chlorobenzene | B(2F,3Cl) |

(5) Example of Description

Example 1 V-DhHB(2F,3F)-O2

Example 2 3-BB(3F)B-4

Example 3 5-HBB(3F)B-3

Example 4 3-HBB(2F,3F)-O2

Example 4

| | | |
|---|---|---|
| V-DhHB(2F,3F)-O2 | (Compound No. 7) | 12% |
| 2-BB(3F)B-3 | (12-6) | 9% |
| V2-BB(3F)B-1 | (12-6) | 8% |
| 3-H2B(2F,3F)-O2 | (6-3) | 18% |
| 5-H2B(2F,3F)-O2 | (6-3) | 18% |
| 5-HHB(2F,3F)-O2 | (7-1) | 12% |
| 3-HBB(2F,3Cl)-O2 | (7-9) | 7% |
| 2-HBB(2F,3F)-O2 | (7-5) | 8% |
| 5-HBB(2F,3F)-O2 | (7-5) | 8% |

NI = 95.4° C.;
Tc = ≦−20° C.;
Δn = 0.140;
η = 35.8 mPa·s

Example 5

| | | |
|---|---|---|
| V-DhHB(2F,3F)-O2 | (Compound No. 7) | 10% |
| 2-BB(3F)B-3 | (12-6) | 8% |
| V2-BB(3F)B-1 | (12-6) | 7% |
| 3-HB-O2 | (11-5) | 3% |
| 3-HB(2F,3F)-O4 | (6-1) | 3% |
| 3-H2B(2F,3F)-O2 | (6-3) | 17% |
| 5-H2B(2F,3F)-O2 | (6-3) | 20% |
| 3-HBB(2F,3Cl)-O2 | (7-9) | 10% |

-continued

| | | |
|---|---|---|
| 5-HBB(2F,3Cl)-O2 | (7-9) | 2% |
| 3-HBB(2F,3F)-O2 | (7-5) | 10% |
| 5-HBB(2F,3F)-O2 | (7-5) | 10% |

NI = 88.2° C.;
Δn = 0.140;
η = 35.3 mPa·s

Example 6

| | | |
|---|---|---|
| V-DhHB(2F,3F)-O2 | (Compound No. 7) | 12% |
| V2-BB(3F)B-1 | (12-6) | 5% |
| 3-HBB(3F)B-3 | (13-5) | 3% |
| V2-BB-1 | (11-8) | 5% |
| 1V-HBB-2 | (12-4) | 4% |
| V-HB(2F,3F)-O2 | (6-1) | 7% |
| 3-H2B(2F,3F)-O2 | (6-3) | 20% |
| 5-H2B(2F,3F)-O2 | (6-3) | 8% |
| 3-HBB(2F,3Cl)-O2 | (7-9) | 10% |
| 3-HBB(2F,3F)-O2 | (7-5) | 10% |
| 5-HBB(2F,3F)-O2 | (7-5) | 5% |
| V-HBB(2F,3F)-O2 | (7-5) | 11% |

NI = 93.0° C.;
Δn = 0.141;
η = 36.0 mPa·s

Example 7

| | | |
|---|---|---|
| V-DhHB(2F,3F)-O2 | (Compound No. 7) | 7% |
| 2-BB(3F)B-3 | (12-6) | 3% |
| V2-BB(3F)B-1 | (12-6) | 5% |
| V2-BB-1 | (11-8) | 5% |
| 3-HB(3F)BH-3 | (13-2) | 5% |
| 3-H2B(2F,3F)-O2 | (6-3) | 18% |
| 5-H2B(2F,3F)-O2 | (6-3) | 18% |
| 2-HHB(2F,3Cl)-O2 | (7-8) | 3% |
| V-HHB(2F,3F)-O2 | (7-1) | 3% |
| 3-HBB(2F,3F)-O2 | (7-5) | 10% |
| 4-HBB(2F,3F)-O2 | (7-5) | 10% |
| V-HBB(2F,3F)-O2 | (7-5) | 8% |
| 2-BB(2F,3F)B-3 | (8-1) | 5% |

NI = 90.5° C.;
Δn = 0.140;
η = 36.8 mPa·s

Example 8

| | | |
|---|---|---|
| V-DhHB(2F,3F)-O2 | (Compound No. 7) | 10% |
| 2-BB(3F)B-3 | (12-6) | 5% |
| V2-BB-1 | (11-8) | 11% |
| V-HHB-1 | (12-1) | 3% |
| 3-H2B(2F,3F)-O2 | (6-3) | 15% |
| 5-H2B(2F,3F)-O2 | (6-3) | 15% |
| V2-HBB(2F,3Cl)-O2 | (7-9) | 3% |
| 2-HBB(2F,3F)-O2 | (7-5) | 10% |
| 3-HBB(2F,3F)-O2 | (7-5) | 10% |
| 5-HBB(2F,3F)-O2 | (7-5) | 5% |
| V-HBB(2F,3F)-O2 | (7-5) | 10% |
| 1O1-HBBH-4 | (13-1) | 3% |

NI = 90.6° C.;
Δn = 0.140;
η = 32.0 mPa·s

Example 9

| | | |
|---|---|---|
| V-DhHB(2F,3F)-O2 | (Compound No. 7) | 9% |
| 2-BB(3F)B-3 | (12-6) | 10% |
| 3-HB-O2 | (11-5) | 3% |
| V2-BB-1 | (11-8) | 7% |
| 3-HHEH-4 | (12-12) | 3% |
| 3-H2B(2F,3F)-O2 | (6-3) | 15% |
| 5-H2B(2F,3F)-O2 | (6-3) | 15% |
| 2-HBB(2F,3F)-O2 | (7-5) | 10% |
| 3-HBB(2F,3F)-O2 | (7-5) | 10% |
| 4-HBB(2F,3F)-O2 | (7-5) | 10% |
| V-HBB(2F,3F)-O2 | (7-5) | 5% |
| 3-HBBH-3 | (13-1) | 3% |

NI = 92.1° C.;
Δn = 0.141;
η = 34.1 mPa·s

When 0.25 part of the optically active compound (Op-5) was added to 100 parts of the composition, the pitch was 61.0 µm.

Example 10

| | | |
|---|---|---|
| V-DhHB(2F,3F)-O2 | (Compound No. 7) | 7% |
| 2-BB(3F)B-3 | (12-6) | 7% |
| 3-HB-O2 | (11-5) | 3% |
| V2-BB-1 | (11-8) | 14% |
| 3-HHB-1 | (12-1) | 3% |
| 3-HHEBH-4 | (13-6) | 3% |
| 3-H2B(2F,3F)-O2 | (6-3) | 10% |
| 5-H2B(2F,3F)-O2 | (6-3) | 10% |
| V2-HBB(2F,3Cl)-O2 | (7-9) | 8% |
| 2-HBB(2F,3F)-O2 | (7-5) | 10% |
| 3-HBB(2F,3F)-O2 | (7-5) | 5% |
| 4-HBB(2F,3F)-O2 | (7-5) | 10% |
| 5-HBB(2F,3F)-O2 | (7-5) | 10% |

NI = 98.3° C.;
Δn = 0.147;
η = 30.9 mPa·s

Example 11

| | | |
|---|---|---|
| V-DhHB(2F,3F)-O2 | (Compound No. 7) | 8% |
| 2-BB(3F)B-3 | (12-6) | 7% |
| V2-BB(3F)B-1 | (12-6) | 5% |
| 3-HB-O2 | (11-5) | 12% |
| 3-HHB-O1 | (12-1) | 3% |
| 3-H2B(2F,3F)-O2 | (6-3) | 18% |
| 2-HHB(2F,3F)-1 | (7-1) | 12% |
| 2-HBB(2F,3F)-O2 | (7-5) | 10% |
| 3-HBB(2F,3F)-O2 | (7-5) | 10% |
| 4-HBB(2F,3F)-O2 | (7-5) | 5% |
| 5-HBB(2F,3F)-O2 | (7-5) | 10% |

NI = 98.9° C.;
Δn = 0.141;
η = 34.5 mPa·s

Example 12

| | | |
|---|---|---|
| V-dhHB(2F,3F)-O2 | (Compound No. 77) | 5% |
| V-DhHB(2F,3F)-O2 | (Compound No. 7) | 5% |
| 2-BB(3F)B-3 | (12-6) | 5% |
| V2-BB-1 | (11-8) | 11% |
| V-HHB-1 | (12-1) | 3% |
| 3-H2B(2F,3F)-O2 | (6-3) | 15% |
| 5-H2B(2F,3F)-O2 | (6-3) | 15% |
| V2-HBB(2F,3Cl)-O2 | (7-9) | 3% |
| 2-HBB(2F,3F)-O2 | (7-5) | 10% |
| 3-HBB(2F,3F)-O2 | (7-5) | 10% |
| 5-HBB(2F,3F)-O2 | (7-5) | 5% |
| V-HBB(2F,3F)-O2 | (7-5) | 10% |
| 1O1-HBBH-4 | (13-1) | 3% |

The invention provides a liquid crystal compound that is excellent in compatibility with other liquid crystal materials and has a negatively large dielectric anisotropy (Δε).

The invention also provides a novel liquid crystal composition that contains the liquid crystal compound as a component and has desired characteristics by appropriately selecting the rings, the groups and so forth constituting the compound, and further provides a liquid crystal display device that is constituted by using the liquid crystal composition.

What is claimed is:

1. A compound represented by formula (1-1):

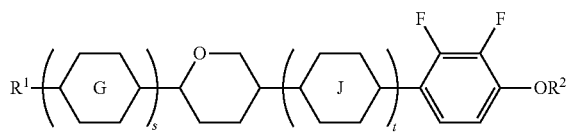
(1-1)

wherein
$R^1$ is alkenyl having 2 to 10 carbons, in the alkenyl arbitrary —$CH_2$— may be replaced by —O—, —S—, —CO— or —$SiH_2$—, provided that plural —$CH_2$— adjacent to each other are not replaced simultaneously;
$R^2$ is alkyl having 1 to 10 carbons, in the alkyl having 2 to 10 carbons arbitrary —$CH_2$— may be replaced by —O—, —S—, —CO— or —$SiH_2$—, provided that plural —$CH_2$— adjacent to each other are not replaced simultaneously, and arbitrary —$(CH_2)_2$— may be replaced by —CH=CH— or —C≡C—;
ring G and ring J are each independently 1,4-cyclohexylene or 1,4-phenylene, in the 1,4-cyclohexylene arbitrary —$CH_2$— may be replaced by —O—, —S—, —CO— or —$SiH_2$—, and arbitrary —$(CH_2)_2$— may be replaced by —CH=CH—, and in the 1,4-phenylene arbitrary —CH= may be replaced by —N=; and
s and t are each independently 0, 1, 2 or 3, provided that the sum of s and t is 1, 2 or 3,
provided that
in formula (1-1), when s=1 and t=0, ring G is 1,4-phenylene, in which arbitrary —CH= may be replaced by —N=.

2. The compound according to claim 1, wherein in formula (1-1), $R^1$ is alkenyl having 2 to 10 carbons; $R^2$ is alkyl having 1 to 10 carbons; and ring G and ring J are each independently 1,4-cyclohexylene or 1,4-phenylene.

3. The compound according to claim 1, wherein in formula (1-1), the sum of s and t is 1.

4. A compound represented by formula (1-1-1):

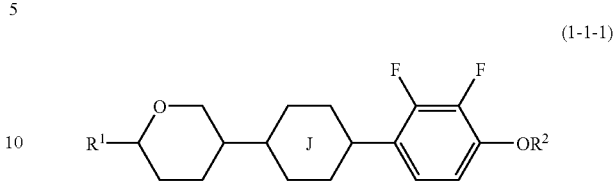
(1-1-1)

wherein $R^1$ is alkenyl having 2 to 10 carbons; $R^2$ is alkyl having 1 to 10 carbons; and ring J is 1,4-cyclohexylene or 1,4-phenylene.

5. A liquid crystal composition comprising, as a component A, at least one of the compound according to claim 1.

6. The liquid crystal composition according to claim 5, wherein the liquid crystal composition further comprises, as a component B, at least one compound selected from the group consisting of compounds represented by formulae (2), (3) and (4):

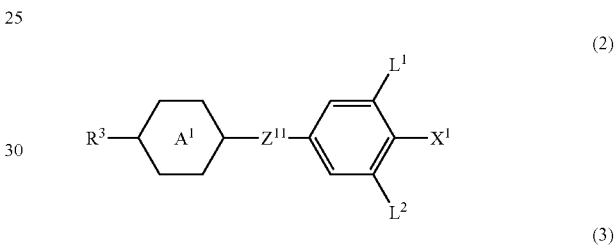
(2)

(3)

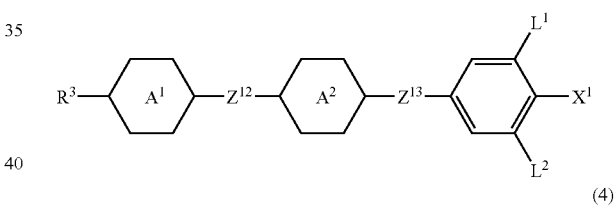
(4)

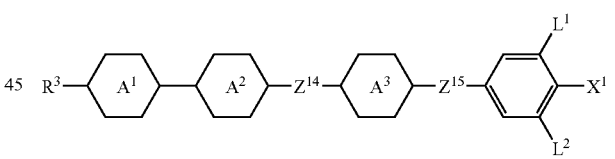

wherein
$R^3$ is alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;
$X^1$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $A^1$, ring $A^2$ and ring $A^3$ are each independently 1,4-cyclohexylene, 1,3-dioxan-2,5-diyl, pyrimidin-2,5-diyl, 1-tetrahydropyran-2,5-diyl or 1,4-phenylene, in which arbitrary hydrogen may be replaced by fluorine;
$Z^{11}$, $Z^{12}$, $Z^{13}$, $Z^{14}$ and $Z^{15}$ are each independently —$(CH_2)_2$—, —$(CH_2)_4$—, —COO—, —$CF_2O$—, —$OCF_2$—, —CH=CH—, —C≡C—, —$CH_2O$— or a single bond; and
$L^1$ and $L^2$ are each independently hydrogen or fluorine.

7. The liquid crystal composition according to claim 5, wherein the liquid crystal composition further comprises, as a component C, at least one compound selected from the group consisting of compounds represented by formula (5):

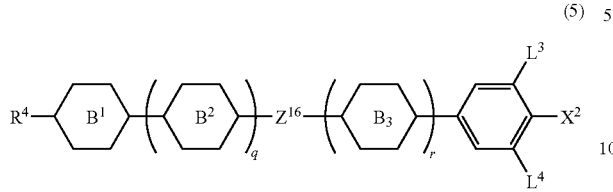
(5)

wherein
$R^4$ is alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;
$X^2$ is —C≡N or —C≡C—CN;
ring $B^1$, ring $B^2$ and ring $B^3$ are each independently 1,4-cyclohexylene, 1,4-phenylene, in which arbitrary hydrogen may be replaced by fluorine, 1,3-dioxan-2,5-diyl, 1-tetrahydropyran-2,5-diyl or pyrimidin-2,5-diyl;
$Z^{16}$ is —$(CH_2)_2$—, —COO—, —$CF_2O$—, —$OCF_2$—, —C≡C—, —$CH_2O$— or a single bond;
$L^3$ and $L^4$ are each independently hydrogen or fluorine;
q is 0, 1 or 2; and
r is 0 or 1.

8. The liquid crystal composition according to claim 5, wherein the liquid crystal composition further comprises, as a component D, at least one compound selected from the group consisting of compounds represented by formulae (6), (7), (8), (9) and (10):

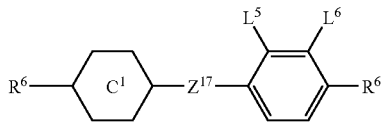
(6)

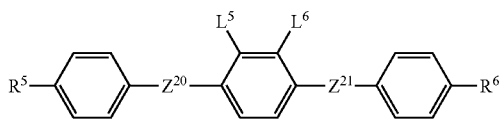
(7)

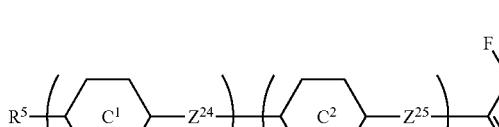
(8)

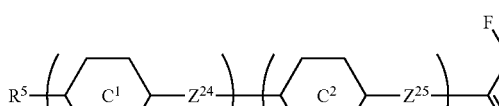
(9)

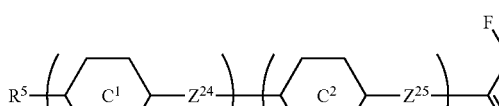
(10)

wherein
$R^5$ and $R^6$ are each independently alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;
ring $C^1$, ring $C^2$, ring $C^3$ and ring $C^4$ are each independently 1,4-cyclohexylene, 1,4-cyclohexenylene, 1,4-phenylene, in which arbitrary hydrogen may be replaced by fluorine, 6-tetrahydropyran-2,5-diyl or decahydro-2,6-naphthalene;

$Z^{17}$, $Z^{18}$, $Z^{19}$, $Z^{20}$, $Z^{21}$, $Z^{22}$, $Z^{23}$, $Z^{24}$, $Z^{25}$, $Z^{26}$ and $Z^{27}$ are each independently —$(CH_2)_2$—, —COO—, —$CH_2O$—, —$OCF_2$—, —$OCF_2(CH_2)_2$— or a single bond;
$L^5$ and $L^6$ are each independently chlorine or fluorine; and
j, k, l, m and n are each independently 0 or 1, provided that the sum of k, l, m and n is 1 or 2.

9. The liquid crystal composition according to claim 5, wherein the liquid crystal composition further comprises, as a component E, at least one compound selected from the group consisting of compounds represented by formulae (11), (12) and (13):

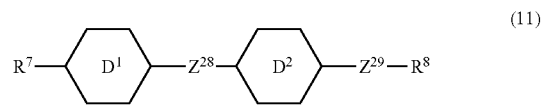
(11)

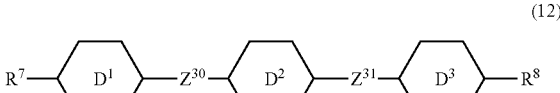
(12)

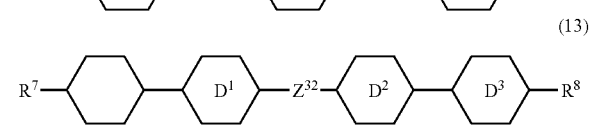
(13)

wherein
$R^7$ and $R^8$ are each independently alkyl having 1 to 10 carbons or alkenyl having 2 to 10 carbons, provided that in the alkyl having 2 to 10 carbons and the alkenyl, arbitrary hydrogen may be replaced by fluorine, and arbitrary —$CH_2$— may be replaced by —O—;
ring $D^1$, ring $D^2$ and ring $D^3$ are each independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and
$Z^{28}$, $Z^{29}$, $Z^{30}$, $Z^{31}$ and $Z^{32}$ are each independently —C≡C—, —COO—, —$(CH_2)_2$—, —CH=CH— or a single bond.

10. The liquid crystal composition according to claim 6, wherein the liquid crystal composition further comprises at least one compound selected from the group consisting of compounds represented by formula (5):

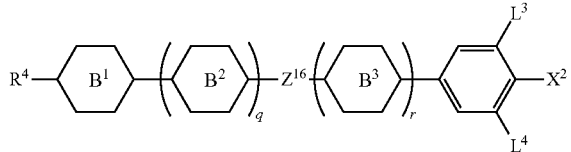

(5)

wherein
$R^4$ is alkyl having 1 to 10 carbons or alkenyl having 2 to 10 carbons, provided that in the alkyl and the alkenyl, arbitrary hydrogen may be replaced by fluorine, and arbitrary —$CH_2$— may be replaced by —O—;
$X^2$ is —C≡N or —C≡C—CN;
ring $B^1$, ring $B^2$ and ring $B^3$ are each independently 1,4-cyclohexylene, 1,4-phenylene, in which arbitrary hydrogen may be replaced by fluorine, 1,3-dioxan-2,5-diyl, 1-tetrahydropyran-2,5-diyl or pyrimidin-2,5-diyl;
$Z^{16}$ is —$(CH_2)_2$—, —COO—, —$CF_2O$—, —$OCF_2$—, —C≡C—, —$CH_2O$— or a single bond;
$L^3$ and $L^4$ are each independently hydrogen or fluorine;
q is 0, 1 or 2; and
r is 0 or 1.

11. The liquid crystal composition according to claim 6, wherein the liquid crystal composition further comprises at least one compound selected from the group consisting of compounds represented by formulae (11), (12) and (13):

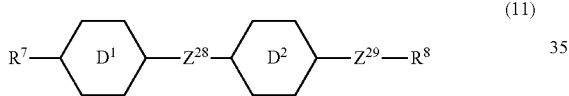

(11)

wherein
$R^7$ and $R^8$ are each independently alkyl having 1 to 10 carbons or alkenyl having 2 to 10 carbons, provided that in the alkyl having 2 to 10 carbons and the alkenyl, arbitrary hydrogen may be replaced by fluorine, and arbitrary —$CH_2$— may be replaced by —O—;
ring $D^1$, ring $D^2$ and ring $D^3$ are each independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and
$Z^{28}$, $Z^{29}$, $Z^{30}$, $Z^{31}$ and $Z^{32}$ are each independently —C≡C—, —COO—, —$(CH_2)_2$—, —CH═CH— or a single bond.

12. The liquid crystal composition according to claim 7, wherein the liquid crystal composition further comprises at least one compound selected from the group consisting of compounds represented by formulae (11), (12) and (13):

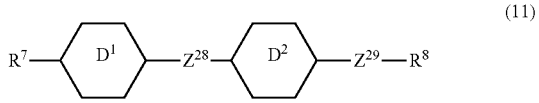

(11)

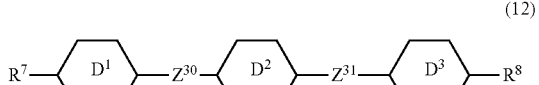

(12)

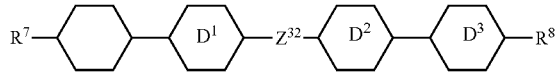

(13)

wherein
$R^7$ and $R^8$ are each independently alkyl having 1 to 10 carbons or alkenyl having 2 to 10 carbons, provided that in the alkyl having 2 to 10 carbons and the alkenyl, arbitrary hydrogen may be replaced by fluorine, and arbitrary —$CH_2$— may be replaced by —O—;
ring $D^1$, ring $D^2$ and ring $D^3$ are each independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and
$Z^{28}$, $Z^{29}$, $Z^{30}$, $Z^{31}$ and $Z^{32}$ are each independently —C≡C—, —COO—, —$(CH_2)_2$—, —CH═CH— or a single bond.

13. The liquid crystal composition according to claim 8, wherein the liquid crystal composition further comprises at least one compound selected from the group consisting of compounds represented by formulae (11), (12) and (13):

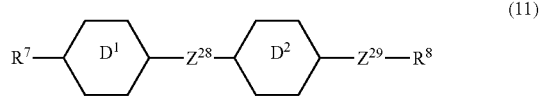

(11)

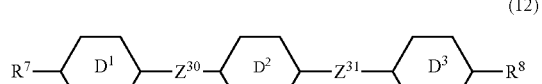

(12)

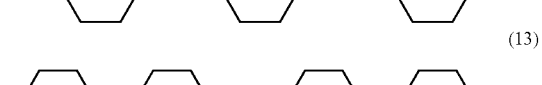

(13)

wherein
$R^7$ and $R^8$ are each independently alkyl having 1 to 10 carbons or alkenyl having 2 to 10 carbons, provided that in the alkyl having 2 to 10 carbons and the alkenyl, arbitrary hydrogen may be replaced by fluorine, and arbitrary —$CH_2$— may be replaced by —O—;
ring $D^1$, ring $D^2$ and ring $D^3$ are each independently 1,4-cyclohexylene, pyrimidin-2,5-diyl, 1,4-phenylene, 2-fluoro-1,4-phenylene, 3-fluoro-1,4-phenylene or 2,5-difluoro-1,4-phenylene; and
$Z^{28}$, $Z^{29}$, $Z^{30}$, $Z^{31}$ and $Z^{32}$ are each independently —C≡C—, —COO—, —$(CH_2)_2$—, —CH═CH— or a single bond.

14. The liquid crystal composition according to claim 5, wherein the liquid crystal composition further comprises at least one optically active compound.

15. The liquid crystal composition according to claim 5, wherein the liquid crystal composition further comprises at least one compound selected from an antioxidant and an ultraviolet absorbent.

16. A liquid crystal display device comprising at least one of the liquid crystal composition according to claim 5.

* * * * *